US010744157B2

(12) United States Patent
Sentman et al.

(10) Patent No.: US 10,744,157 B2
(45) Date of Patent: Aug. 18, 2020

(54) ANTI-MICA ANTIGEN BINDING FRAGMENTS, FUSION MOLECULES, CELLS WHICH EXPRESS AND METHODS OF USING

(71) Applicant: THE TRUSTEES OF DARTMOUTH COLLEGE, New Hampshire, NH (US)

(72) Inventors: Charles Sentman, Grantham, NH (US); Michael Battles, Canaan, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 181 days.

(21) Appl. No.: 15/561,748

(22) PCT Filed: Mar. 25, 2016

(86) PCT No.: PCT/US2016/024322
§ 371 (c)(1),
(2) Date: Sep. 26, 2017

(87) PCT Pub. No.: WO2016/154585
PCT Pub. Date: Sep. 29, 2016

(65) Prior Publication Data
US 2018/0085400 A1    Mar. 29, 2018

Related U.S. Application Data

(60) Provisional application No. 62/138,561, filed on Mar. 26, 2015.

(51) Int. Cl.
| | |
|---|---|
| C07K 16/28 | (2006.01) |
| A61K 35/17 | (2015.01) |
| A61K 47/68 | (2017.01) |
| A61P 35/00 | (2006.01) |
| A61K 51/10 | (2006.01) |
| A61K 39/00 | (2006.01) |

(52) U.S. Cl.
CPC .......... *A61K 35/17* (2013.01); *A61K 47/6835* (2017.08); *A61K 51/1045* (2013.01); *A61K 51/1096* (2013.01); *A61P 35/00* (2018.01); *C07K 16/2809* (2013.01); *C07K 16/2833* (2013.01); *C07K 16/2851* (2013.01); *A61K 2039/505* (2013.01); *C07K 2317/31* (2013.01); *C07K 2317/622* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 3,832,253 A | 8/1974 | Di Palma et al. | |
| 3,854,480 A | 12/1974 | Zaffaroni | |
| 4,452,775 A | 6/1984 | Kent | |
| 4,667,014 A | 5/1987 | Nestor, Jr. et al. | |
| 4,690,915 A | 9/1987 | Rosenberg | |
| 4,748,034 A | 5/1988 | de Rham | |
| 5,075,109 A | 12/1991 | Tice et al. | |
| 5,239,660 A | 8/1993 | Ooi | |
| 5,929,212 A | 7/1999 | Jolliffe et al. | |
| 8,192,984 B2 | 6/2012 | Atabekov et al. | |
| 2005/0112095 A1 | 5/2005 | Hsu et al. | |
| 2010/0272718 A1 | 10/2010 | Urso et al. | |
| 2011/0091372 A1 | 4/2011 | Ghayur et al. | |

FOREIGN PATENT DOCUMENTS

| | | |
|---|---|---|
| CN | 102911270 | 2/2013 |
| WO | WO 2005/061547 | 7/2005 |
| WO | WO 2006/113665 | 10/2006 |
| WO | WO 2008/122039 | 10/2008 |
| WO | WO 2008/157379 | 12/2008 |
| WO | WO 2010/080538 | 7/2010 |
| WO | WO 2010/119257 | 10/2010 |
| WO | 2011/090762 | 7/2011 |
| WO | 2013/049517 | 4/2013 |
| WO | 2013/117647 | 8/2013 |
| WO | 2014/117121 | 7/2014 |
| WO | 2014/144791 | 9/2014 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Winkler et al (J. Imm., 265:4505-4514, 2000).*
Hirsch R, et al. "Effects of in vivo administration of anti-T3 monoclonal antibody on T cell function in mice. I. Immunosuppression of transplantation responses," J Immunol. Jun. 1, 1988;140(11):3766-72.
Shastri et al. "Endogenous generation and presentation of the ovalbumin peptide/Kb complex to T cells." The Journal of Immunology. Apr. 1, 1993;150(7):2724-36.
Baeuerle PA, Reinhardt C. "Bispecific T-cell engaging antibodies for cancer therapy." Cancer research. Jun. 15, 2009;69(12):4941-4.
Salih et al. "Soluble NKG2D ligands: prevalence, release, and functional impact." Front Biosci. May 1, 2008;13(5):3448-56.
Ailor et al. "Modifying secretion and post-translational processing in insect cells. Current opinion in biotechnology." Apr. 1, 1999;10(2):142-5.
Arakawa et al. "Cloning and Sequencing of the VH and YK Genes of an Anti-CD3 Monoclonal Antibody, and Construction of a Mouse/Human Chimeric Antibody. The Journal of Biochemistry." Sep. 1, 1996;120(3):657-62.
Bargou et al. "Tumor regression in cancer patients by very low doses of a T cell—engaging antibody," Science. Aug. 15, 2008;321(5891):974-7.

(Continued)

*Primary Examiner* — Brad Duffy
(74) *Attorney, Agent, or Firm* — Robin L. Teskin; Baker, Donelson, Bearman, Caldwell & Berkowitz, PC

(57) ABSTRACT

Antigen binding fragments, chimeric antigen receptors, and bi-specific T-cell engagers having specificity for MICA and methods for using the same in the diagnosis and treatment of disorders associated with MICA and/or MICB expression are provided.

15 Claims, 12 Drawing Sheets
Specification includes a Sequence Listing.

(56) References Cited

OTHER PUBLICATIONS

Bei et al. "Baculovirus expression of a functional single-chain immunoglobulin and its IL-2 fusion protein. Journal of immunological methods." Oct. 26, 1995;186(2):245-55.
Bird et al. "Single-chain antigen binding proteins," Science. Oct. 21, 1988;242(4877):423-6.
Bonini et al. "HSV-TK gene transfer into donor lymphocytes for control of allogeneic graft-versus-leukemia." Science. Jun. 13, 1997;276(5319):1719-24.
Bonnafous et al. "Targeting MICA with therapeutic antibodies for the treatment of cancer." Journal for immunotherapy of cancer. Nov. 1, 2013;1(S1):P41.
Brischwein et al. "Strictly target cell-dependent activation of T cells by bispecific single-chain antibody constructs of the BiTE class." Journal of immunotherapy. Nov. 1, 2007;30(8):798-807.
Burgess et al. "The NKG2D receptor: immunobiology and clinical implications." Immunologic research. Jan. 1, 2008;40(1):18-34.
Canevari et al. "Regression of advanced ovarian carcinoma by Intraperitoneal treatment with autologous TLymphocytes retargeted by a bispecific monoclonal antibody." JNCI: Journal of the National Cancer Institute. Oct. 4, 1995;87(19):1463-9.
Carayannopoulos et al. "Recombinant human IgA expressed in insect cells." Proceedings of the National Academy of Sciences. Aug. 30, 1994;91(18):8348-52.
Carpenito et al. "Control of large, established tumor xenografts with genetically retargeted human T cells containing CD28 and CD137 domains". Proceedings of the National Academy of Sciences. Mar. 3, 2009;106(9):3360-5.
Chalupny et al. "Down-regulation of the NKG2D ligand MICA by the human cytomegalovirus glycoprotein UL142." Biochemical and biophysical research communications. Jul. 21, 2006;346(1):175-81.
Colonna, Marco. "NK cells: new issues and challenges." European journal of immunology. Nov. 2008;38(11):2927-9.
Dorai et al. "Mammalian Cell Expression of Single-Chain Fv (sFv) Antibody Proteins and Their C-terminal Fusions with Interleukin-2 and Other Effector Domains." Bio/technology. Sep. 1994;12(9):890-7.
Duval et al. "Adoptive transfer of allogeneic cytotoxic T lymphocytes equipped with a HLA-A2 restricted MART-1 T-cell receptor: a phase I trial in metastatic melanoma." Clinical Cancer Research. Feb. 15, 2006;12(4):1229-36.
Feldhaus et al. "Flow-cytometric isolation of human antibodies from a nonimmune *Saccharomyces cerevisiae* surface display library." Nature biotechnology. Feb. 2003;21(2):163-70.
Fischer et al. "Towards molecular farming in the future: transient protein expression in plants." Biotechnology and applied biochemistry. Oct. 1999;30(2):113-6.
Frenken et al. "ScFv antibody fragments produced in *Saccharomyces cerevisiae* accumulate in the endoplasmic reticulum and the vacuole." InBiological Membranes: structure, biogenesis and dynamics 1994 (pp. 223-236). Springer, Berlin, Heidelberg.
Frenken et al. "Recent advances in the large-scale production of antibody fragments using lower eukaryotic microorganisms." Research in immunology. Jul. 1, 1998;149(6):589-99.
Gonzalez et al. "Genetic engineering of cytolytic T lymphocytes for adoptive T-cell therapy of neuroblastoma." The Journal of Gene Medicine: A cross-disciplinary journal for research on the science of gene transfer and its clinical applications. Jun. 2004;6(6):704-11.
Griffioen et al. "Retroviral transfer of human CD20 as a suicide gene for adoptive T-cell therapy." haematoiogica. Sep. 1, 2009;94(9):1316-20.
Hasemann CA, Capra JD. High-level production of a functional immunoglobulin heterodimer in a baculovirus expression system. Proceedings of the National Academy of Sciences. May 1, 1990;87(10):3942-6.
Hiatt et al, 'Production of antibodies in transgenic plants.' Nature, Nov. 2, 1989;342(6245):76-8.

Holdenrieder et al. "Soluble MICB in malignant diseases: analysis of diagnostic significance and correlation with soluble MICA." Cancer Immunology, Immunotherapy. Dec. 1, 2006;55(12):1584-9.
Huston et al. "Protein engineering of antibody binding sites: recovery of specific activity in an anti-digoxin single-chain Fv analogue produced in *Escherichia coli*." Proceedings of the National Academy of Sciences. Aug. 1, 1988;85(16):5879-83.
Introna et al. "Genetic modification of human T cells with CD20: a strategy to purify and lyse transduced cells with anti-CD20 antibodies," Human gene therapy. Mar. 1, 2000;11(4):611-20.
Jost et al. "Mammalian expression and secretion of functional single-chain Fv molecules." Journal of Biological Chemistry. Oct. 21, 1994;269(42):26267-73.
Kato et al. "Regulation of the expression of MHC class I-related chain A, B (MICA, MICB) via chromatin remodeling and its impact on the susceptibility of leukemic cells to the cytotoxicity of NKG2D-expressing cells," Leukemia. Oct. 2007;21(10):2103-8.
King et al. "Expression, purification and characterization of B72. 3 Fv fragments." Biochemical Journal. Mar. 15, 1993;290(3):723-9.
Kowolik et al. "CD28 costimulation provided through a CD19-specific chimeric antigen receptor enhances in vivo persistence and antitumor efficacy of adoptively transferred T cells." Cancer research. Nov. 15, 2006;66(22):10995-1004.
Kretzschmar et al. "High-level expression in insect cells and purification of secreted monomeric single-chain Fv antibodies." Journal of immunological methods. Sep. 9, 1996;195(1-2):93-101.
Kuroiwa et al. "Cloned transchromosomic calves producing human immunoglobulin." Nature biotechnology. Sep. 2002;20(9):889-94.
Lang et al. "Chimeric CD19 antibody mediates cytotoxic activity against leukemic blasts with effector cells from pediatric patients who received T-cell—depleted allografts." Blood. May 15, 2004;103(10):3982-5.
Le Gall et al. "Effect of linker sequences between the antibody variable domains on the formation, stability and biological activity of a bispecific tandem diabody," Protein Engineering Design and Selection. Apr. 1, 2004;17(4):357-66.
Little et al. "Of mice and men: hybridoma and recombinant antibodies." Immunology today, Aug. 1, 2000;21(8):364-70.
Maher et al. "Human T-lymphocyte cytotoxicity and proliferation directed by a single chimeric TCRζ/CD28 receptor." Nature biotechnology. Jan. 2002;20(1):70-5.
Mahiouz et al. "Expression of recombinant anti-E-selectin single-chain Fv antibody fragments in stably transfected insect cell lines," Journal of immunological methods. Mar. 15, 1998;212(2):149-60.
Marcu-Malina et al. "Re-targeting T-cells against cancer by gene-transfer of tumor reactive receptors." Expert Opinion on Biological Therapy, May 1, 2009;9(5):579-91.
Märten et al. "Soluble MIC is elevated in the serum of patients with pancreatic carcinoma diminishing γδ T cell cytotoxicity." International journal of cancer. Nov. 15, 2006;119(10):2359-65.
Neuberger MS. "Making novel antibodies by expressing transfected immunoglobulin genes." Trends in Biochemical Sciences. Sep. 1, 1985;10(9):347-9.
Neuberger et al. "Recombinant antibodies possessing novel effector functions." Nature. Dec. 1984;312(5995):604-8.
Nyyssönen et al. "Efficient production of antibody fragments by the filamentous fungus Trichoderma reesei." Bio/Technology. May 1993;11(5):591-5.
Papazahariadou et al. "Involvement of NK cells against tumors and parasites," The International journal of biological markers. Apr. 2007;22(2):144-53.
Parente-Pereira et al. "Trafficking of CAR-engineered human T cells following regional or systemic adoptive transfer in SCID beige mice." Journal of clinical immunology. Aug. 1, 2011;31(4):710-8.
Paschen et al. "Differential clinical significance of individual NKG2D ligands in melanoma: soluble ULBP2 as an indicator of poor prognosis superior to S100B." Clinical cancer research. Aug. 15, 2009;15(16):5208-15.
Pollock et al. "Transgenic milk as a method for the production of recombinant antibodies." Journal of immunological methods. Dec. 10, 1999;231(1-2):147-57.

(56) References Cited

OTHER PUBLICATIONS

Pulè et al. "A chimeric T cell antigen receptor that augments cytokine release and supports clonal expansion of primary human T cells." Molecular Therapy. Nov. 1, 2005;12(5):933-41.

Riechmann et al. "Expression of an antibody Fv fragment in myeloma cells." Journal of molecular biology. Oct. 5, 1988;203(3):825-8.

Sáez-Borderías et al. "Expression and function of NKG2D in CD4+ T cells specific for human cytomegalovirus." European journal of immunology. Dec. 2006;36(12):3198-206.

Salih et al. "Release of MICB molecules by tumor cells: mechanism and soluble MICB in sera of cancer patients." Human immunology. Mar. 1, 2006;67(3):188-95.

Santoni et al. "Natural killer (NK) cells from killers to regulators: distinct features between peripheral blood and decidual NK cells." American Journal of Reproductive Immunology. Sep. 2007;58(3):280-8.

Siegel et al. "High efficiency recovery and epitope-specific sorting of an scFv yeast display library." Journal of immunological methods. Mar. 1, 2004;286(1-2):141-53.

Song et al. "In vivo persistence, tumor localization, and antitumor activity of CAR-engineered T cells is enhanced by costimulatory signaling through CD137 (4-1BB)." Cancer research. Jul. 1, 2011;71(13):4617-27.

Sotiriadis et al. "Factors Affecting the Production of a Single-Chain Antibody Fragment by Aspergillus awamoriin a Stirred Tank Reactor." Biotechnology progress. 2001;17(4):618-23.

Terakura et al. "Generation of CD19-chimeric antigen receptor modified CD8+ T cells derived from virus-specific central memory T cells." Blood, the Journal of the American Society of Hematology. Jan. 5, 2012;119(1):72-82.

Tey et al. "Inducible caspase 9 Suicide gene to improve the safety of allodepleted T cells after haploidentical stem cell transplantation." Biology of Blood and Marrow Transplantation. Aug. 1, 2007;13(8):913-24.

Thomis et al. "A Fas-based suicide switch in human T cells for the treatment of graft-versus-host disease." Blood, the Journal of the American Society of Hematology. Mar. 1, 2001;97(5):1249-57.

Topalian et al. "Therapy of cancer using the adoptive transfer of activated killer cells and interleukin-2." Acta haematologica. 1987;78(Suppl. 1):75-6.

Tosh et al. "Variation in MICA and MICB genes and enhanced susceptibility to paucibacillary leprosy in South India." Human molecular genetics. Oct. 1, 2006;15(19):2880-7.

Unni et al. "Intrinsic sensor of oncogenic transformation induces a signal for innate immunosurveillance." Proceedings of the National Academy of Sciences. Feb. 5, 2008;105(5):1686-91.

Weaver-Feldhaus et al. "Yeast mating for combinatorial Fab library generation and surface display." FEBS letters. Apr. 23, 2004;564(1.-2):24-34.

Wrobel et al. "Lysis of a broad range of epithelial tumour cells by human γδ T cells: involvement of NKG2D ligands and T-cell receptor-versus NKG2D-dependent recognition." Scandinavian journal of immunology. Aug. 2007;66(2-3):320-8.

Wu et al. "Arming antibodies: prospects and challenges for immunoconjugates." Nature biotechnology. Sep. 2005;23(9):1137-46.

Young et al. "Production of recombinant antibodies in the milk of transgenic animals." Discussion. Research in immunology (Paris). 1998;149(6):609-20.

Zhao et al. "A herceptin-based chimeric antigen receptor with modified signaling domains leads to enhanced survival of transduced T lymphocytes and antitumor activity." The Journal of Immunology. Nov. 1, 2009;183(9):5563-74.

Zhao et al. "Multiple injections of electroporated autologous T cells expressing a chimeric antigen receptor mediate regression of human disseminated tumor." Cancer research. Nov. 15, 2010;70(22):9053-61.

Zhong et al. "Chimeric antigen receptors combining 4-1BB and CD28 signaling domains augment PI3kinase/AKT/Bcl-XL activation and CD8+ T cell—mediated tumor eradication," Molecular Therapy. Feb. 1, 2010;18(2):413-20.

* cited by examiner scFv B2

ATGGAATGGACCTGGGTCTTTCTCTTCCTCCTGTCAGTAACTGCAGGTG
TCCACTCCCAGGTACAGCTGCAGCAGTCAGGTCCAGGACTGGTGAAGCC
CTCGCAGACCCTCTCACTCACCTGTGCCATCTCCGGGACAGTGTCTCT
AGTAACAGTGCTGCTTGGAACTGGATCAGGCAGTCCCCATCGAGAGGCC
TTGAGTGGCTGGGAAGGACATACTACAGGTCCAAGTGGTATAATGATTA
TGCAGTATCTGTGAAAAGTCGAATAACCATCAACCCAGACACATCCACG
AACCAGTTCTCCCTGCAGCTGAACTCTGTGACTCCCGACGACACGGCTG
TGTATTACTGTGCAAGAGAGGGGCCCATGAGTGGGCCGATGCTTTTGA
TATCTGGGGCCAAGGGACAATGGTCACCGTCTCTTCAGGAATTCTAGGA
TCCGGTGGCGGTGGCAGCGGCGGTGGTGGTTCCGGAGGCGGCGGTTCTG
ACATCCAGTTGACCCAGTCTCCATCCTCCCTGTCTGCATCTGTAGGAGA
CAGAGTCACCATCACTTGCCAGGCGAGTCAAGACATTAGCAACTATTTA
AATTGGTATCAGCAGAAACCAGGGAAAGCCCCTAAGCTCCTGATCTACG
ATGCATCCAATTTGGAAACAGGGGTCCCACCAAGGTTCAGTGGAAGTGG
ATCTGGGACAGCTTTTACTTTCACCATCAGCAGCCTGCAGCCTGAAGAT
TTTGCAACATATTACTGTCAACAGTATGATAATCTCCCTCACACTTTCG
GCCCTGGGACCAAAGTGGATATCAAATCC (SEQ ID NO:1)

```
                                                    CDR1
MEWTWVFLFLLSVTAGVHSQVQLQQSGPGLVKPSQTLSLTCAIS|GDSVS|
Signal Sequence
                          CDR2
|SNSAAWN|WIRQSPSRGLEWLGRT|YYRSKWYN|DYAVSVKSRITINPDTST
         Heavy Chain Variable Region
                              CDR3
NQFSLQLNSVTPDDTAVYYCAR|EGAHEWADAFDI|WGQGTMVTVSSGILG
                                                    CDR1
SGGGGSGGGGSGGGGSDIQLTQSPSSLSASVGDRVTITC|QASQDISNYL|
Linker
            CDR2
|N|WYQQKPGKAPKLLIY|DASNLET|GVPPRFSGSGSGTAFTFTISSLQPED
             Light Chain Variable Region
   CDR3
FATYYC|QQYDNLPHT|FGPGTKVDIKS (SEQ ID NO:2)
```

*FIG. 1A* scFv C11

ATGGAATGGACCTGGGTCTTTCTCTTCCTCCTGTCAGTAACTGCAGGTG
TCCACTCCGAGGTGCAGCTGGTGGAGTCTGGGGGAGGCTTGGTGCAGCC
TGGAAAGTCCCTGAAACTCCTGTGAGGCCTCTGGATTCACCTTCAGC
GGCTATGGCATGCACTGGGTCCGCCAGGCTCCAGGGAGGGGCTGGAGT
CGGTCGCATACATTACTAGTAGTAGTATTAATATCAAATATGCTGACGC
TGTGAAAGGCCGGTTCACCGTCTCCAGAGACAATGCCAAGAACTTACTG
TTTCTACAAATGAACATTCTCAAGTCTGAGGACACAGCCATGTACTACT
GTGCAAGATTCGACTGGGACAAAAATTACTGGGGCCAAGGAACCATGGT
CACCGTCTCCTCAGCCGGCGGAGGCGGATCAGGAGGAGGAGGATCAGGC
GGAGGAGGATCAGAATTCGACATCCAGATGACCCAGTCTCCATCATCAC
TGCCTGCCTCCCTGGGAGACAGAGTCACTATCAACTGTCAGGCCAGTCA
GGACATTAGCAATTATTTAAACTGGTACCAGCAGAAACCAGGGAAAGCT
CCTAAGCTCCTGATCTATTATACAAATAAATTGGCAGATGGAGTCCCAT
CAAGGTTCAGTGGCAGTGGTTCTGGGAGAGATTCTTCTTTCACTATCAG
CAGCCTGGAATCCGAAGATATTGGATCTTATTACTGTCAACAGTATTAT
AACTATCCGTGGACGTTCGGACCTGGCACCAAGCTGGAAATCAAACGG
(SEQ ID NO:3)

*MEWTWVFLFLLSVTAGVHS*EVQLVESGGGLVQPGKSLKLSCEAS GFTFS CDR1

Signal Sequence

GYGMH WVRQAPGRGLESVAYI TSSSIN KYADAVKGRFTVSRDNAKNLL
CDR2

Heavy Chain Variable Region

FLQMNILKSEDTAMYYCAR FDWDKNY WGQGTMVTVSSAGGGGSGGGGSG
CDR3
Linker

GGGSEFDIQMTQSPSSLPASLGDRVTINC QASQDISNYLN WYQQKPGKA
CDR1

PKLLIY YTNKLAD GVPSRFSGSGSGRDSSFTISSLESEDIGSYYC QQYY
CDR2 CDR3

Light Chain Variable Region

NYPWT FGPGTKLEIKR (SEQ ID NO:4)

*FIG. 1B* scFv C25

ATGGAATGGACCTGGGTCTTTCTCTTCCTCCTGTCAGTAACTGCAGGTG
TCCACTCCCAGGTACAGCTGCAGCAGTCAGGTCCAGGACTGGTGAAGCC
CTCGCAGACCCTCTCACTCACCTGTGCCATCTCCGGGGACAGTGTCTCT
AGCAACAGGGGTGCTTGGAACTGGATCCGGCAGTCCCCATCGAGAGGCC
TTGAGTGGCTGGGAAGGACATACTACAGGTCCAGGTGGATTAATGATTA
TGCAGTATCTGTGAAAAGTCGAATAACCGTCAACCCAGACACATCCAAG
AACCAGTTCTCCCTGCAGCTGAATTCTGTGACTCCCGAGGACACGGCTG
TGTATTACTGTGCAAGAGGGCAGCAGGAGAGGTACGACCCTGGGGCCA
GGGAACCCTGGTCACCGTCTCGTCAGGGAGTGCATCCGCCCCAACCGGA
ATTCTAGGATCCGGTGGCGGTGGCAGCGGCGGTGGTGGTTCGGGGGCG
GCGGTTCTTCCTATGTGCTGACTCAGCCACCCTCAGCGTCTGGGACCCC
CGGGCAGAGGGTCACCATCTCTTGTTCTGGAAGCAGTTCCAACATCGGA
AGGAAAGGTGTATATTGGTTTCAGCAGCTCCCAGGAACGGCCCCCAAAG
TCCTCATTTATGGGAATAATCAGCGGCGGTCAGGGGTCCCTGACCGATT
CTCTGGCTCCAGATCTGGCACCTCAGGCTCCCTGGCCATCAGTGGACTC
CGGTCCGAGGATGAGGCTGATTATTACTGTGCAGCATGGGATGACAGCC
TGAATGGTCCTGTGTTCGGAGGAGGCACCCAGCTGACCGTCCTCTCC (SEQ ID NO:5)

*MEWTWVFLFLLSVTAGVHS*QVQLQQSGPGLVKPSQTLSLTCAIS GDSVS
        Signal Sequence                                                    CDR1

CDR2
SNRGAWN WIRQSPSRGLEWLGRT YYRSRWI NDYAVSVKSRITVNPDTSK
                 Heavy Chain Variable Region
                          CDR3
NQFSLQLNSVTPEDTAVYYCAR GQQERYDP WGQGTLVTVSSGSASAPTG CDR1
ILGSGGGGSGGGGSGGGGSSYVLTQPPSASGTPGQRVTISC SGSSSNIG
       Linker
                            CDR2
RKGVY WFQQLPGTAPKVLIY GNNQRRS GVPDRFSGSRSGTSGSLAISGL
               Light Chain Variable Region
             CDR3
RSEDEADYYC AAWDDSLNGPV FGGGTQLTVLS (SEQ ID NO:6)

*FIG. 1C* scFv C8

ATGGAATGGACCTGGGTCTTTCTCTTCCTCCTGTCAGTAACTGCAGGTG
TCCACTCCGAGGTGCAGCTGATGGAGTCTGGGGGAGGCGTGGTCCAGCC
TGGGGGGTCCCTGAGACTCTCCTGTGCAGGCTCTGGTTCACCGTCAGC
AGCAACTTCATGAGCTGGGTCCGCCAGGCTCCAGGGAAGGGTCTGGAGT
GGGTCTCACTTATTTATAGCGATGGTAGCGGTGGTAACACATACTACGC
AGACTCCGTGAAGGGCCGATTCACCGTCTCCAGAGACAATTCCAAGAAC
ACGCTGTATCTTCAAATGAACAGCCTGAGAGAAGAGGACACGGCCCTGT
ATTACTGTGCGAGAGTATCTCGTAGGCGTAGTGGTAGACTATTCGATCT
CTGGGGCCGTGGTACCCTGGTCACTGTCTCCTCAGGAATTCTAGGATCC
GGTGGCGGTGGCAGCGGCGGTGGTGGTTCCGGAGGCGGCGGTTCTCAGT
CTGCTCTGACTCAGCCTCCCTCCGCGTCCGGGTCTCCTGGACAGTCAGT
CACCATCTCCTGCACTGGAACCAGCAGTGACGTTGGTGGTTCTAATTAT
GTCTCCTGGTACCAACAGCACCCAGGCAAAGTCCCCAAACTCATAATTT
ATGAGGTCAGTAAGCGGCCCTCAGGGGTCCTGATCGCTTCTCTGGCTC
CAAGTCTGGCAACACGGCCTCCTGACCGTCTCTGGGCTCCAGGCTGAG
GATGAGGCTGATTATTACTGCAGCTCATATGCAGGCGGCAAGAAGGTGT
TCGGCGGAGGGACCAAGCTCACCGTCCTCTCC (SEQ ID NO:7)

*MEWTWVFLFLLSVTAGVH*SEVQLMESGGGVVQPGGSLRLSCAGS GFTVS
Signal Sequence                                CDR1

SNFMS WVRQAPGKGLEWVSLI YSDGSGGN TYYADSVKGRFTVSRDNSKN
      CDR2
Heavy Chain Variable Region

TLYLQMNSLREEDTALYYCAR VSRRRSGRLFDL WGRGTLVTVSSGILGS
                      CDR3

GGGGSGGGGSGGGGSQSALTQPPSASGSPGQSVTISC TGTSSDVGGSNY
Linker                                   CDR1

VS WYQQHPGKVPKLIIY EVSKRPS GVPDRFSGSKSGNTASLTVSGLQAE
                  CDR2
Light Chain Variable Region

DEADYYC SSYAGGKKV FGGGTKLTVLS (SEQ ID NO:8)
        CDR3

*FIG. 1D*

SEQUENCE LISTING

```
<160> NUMBER OF SEQ ID NOS: 70

<210> SEQ ID NO 1
<211> LENGTH: 813
<212> TYPE: DNA
<213> ORGANISM: Artificial Sequence
<220> FEATURE:
<223> OTHER INFORMATION: scFv B2
```

<400> SEQUENCE: 1

```
atggaatgga cctgggtctt tctcttcctc ctgtcagtaa ctgcaggtgt ccactcccag    60
gtacagctgc agcagtcagg tccaggactg gtgaagccct cgcagaccct ctcactcacc   120
tgtgccatct ccggggacag tgtctctagt aacagtgctg cttggaactg gatcaggcag   180
tccccatcga gaggccttga gtggctggga aggacatact acaggtccaa gtggtataat   240
gattatgcag tatctgtgaa aagtcgaata accatcaacc cagacacatc cacgaaccag   300
ttctccctgc agctgaactc tgtgactccc gacgacacgg ctgtgtatta ctgtgcaaga   360
gagggggccc atgagtgggc cgatgctttt gatatctggg gccaagggac aatggtcacc   420
gtctcttcag gaattctagg atccggtggc ggtggcagcg gcggtggtgg ttccggaggc   480
ggcggttctg acatccagtt gacccagtct ccatcctccc tgtctgcatc tgtaggagac   540
agagtcacca tcacttgcca ggcgagtcaa gacattagca actatttaaa ttggtatcag   600
cagaaaccag ggaaagcccc taagctcctg atctacgatg catccaattt ggaaacaggg   660
gtcccaccaa ggttcagtgg aagtggatct gggacagctt ttactttcac catcagcagc   720
ctgcagcctg aagattttgc aacatattac tgtcaacagt atgataatct ccctcacact   780
ttcggccctg ggaccaaagt ggatatcaaa tcc                                813
```

<210> SEQ ID NO 2
<211> LENGTH: 271
<212> TYPE: PRT
<213> ORGANISM: Artificial Sequence
<220> FEATURE:
<223> OTHER INFORMATION: scFv B2

<400> SEQUENCE: 2

```
Met Glu Trp Thr Trp Val Phe Leu Phe Leu Leu Ser Val Thr Ala Gly
1               5                   10                  15

Val His Ser Gln Val Gln Leu Gln Gln Ser Gly Pro Gly Leu Val Lys
            20                  25                  30

Pro Ser Gln Thr Leu Ser Leu Thr Cys Ala Ile Ser Gly Asp Ser Val
        35                  40                  45

Ser Ser Asn Ser Ala Ala Trp Asn Trp Ile Arg Gln Ser Pro Ser Arg
    50                  55                  60

Gly Leu Glu Trp Leu Gly Arg Thr Tyr Tyr Arg Ser Lys Trp Tyr Asn
65                  70                  75                  80

Asp Tyr Ala Val Ser Val Lys Ser Arg Ile Thr Ile Asn Pro Asp Thr
                85                  90                  95

Ser Thr Asn Gln Phe Ser Leu Gln Leu Asn Ser Val Thr Pro Asp Asp
            100                 105                 110

Thr Ala Val Tyr Tyr Cys Ala Arg Glu Gly Ala His Glu Trp Ala Asp
        115                 120                 125

Ala Phe Asp Ile Trp Gly Gln Gly Thr Met Val Thr Val Ser Ser Gly
    130                 135                 140

Ile Leu Gly Ser Gly Gly Gly Gly Ser Gly Gly Gly Gly Ser Gly Gly
145                 150                 155                 160

Gly Gly Ser Asp Ile Gln Leu Thr Gln Ser Pro Ser Ser Leu Ser Ala
                165                 170                 175

Ser Val Gly Asp Arg Val Thr Ile Thr Cys Gln Ala Ser Gln Asp Ile
            180                 185                 190

Ser Asn Tyr Leu Asn Trp Tyr Gln Gln Lys Pro Gly Lys Ala Pro Lys
        195                 200                 205
```

```
Leu Leu Ile Tyr Asp Ala Ser Asn Leu Glu Thr Gly Val Pro Pro Arg
        210                 215                 220

Phe Ser Gly Ser Gly Ser Gly Thr Ala Phe Thr Phe Thr Ile Ser Ser
225                 230                 235                 240

Leu Gln Pro Glu Asp Phe Ala Thr Tyr Tyr Cys Gln Gln Tyr Asp Asn
                245                 250                 255

Leu Pro His Thr Phe Gly Pro Gly Thr Lys Val Asp Ile Lys Ser
            260                 265                 270

<210> SEQ ID NO 3
<211> LENGTH: 783
<212> TYPE: DNA
<213> ORGANISM: Artificial Sequence
<220> FEATURE:
<223> OTHER INFORMATION: scFv C11

<400> SEQUENCE: 3
atggaatgga cctgggtctt tctcttcctc ctgtcagtaa ctgcaggtgt ccactccgag      60
gtgcagctgg tggagtctgg gggaggcttg gtgcagcctg gaaagtccct gaaactctcc    120
tgtgaggcct ctggattcac cttcagcggc tatggcatgc actgggtccg ccaggctcca    180
gggagggggc tggagtcggt cgcatacatt actagtagta gtattaatat caaatatgct    240
gacgctgtga aggccggttt caccgtctcc agagacaatg ccaagaactt actgtttcta    300
caaatgaaca ttctcaagtc tgaggacaca gccatgtact actgtgcaag attcgactgg    360
gacaaaaatt actggggcca aggaaccatg gtcaccgtct cctcagccgg cggaggcgga    420
tcaggaggag gaggatcagg cggaggagga tcagaattcg acatccagat gacccagtct    480
ccatcatcac tgcctgcctc cctgggagac agagtcacta tcaactgtca ggccagtcag    540
gacattagca attatttaaa ctggtaccag cagaaaccag ggaaagctcc taagctcctg    600
atctattata caaataaatt ggcagatgga gtcccatcaa ggttcagtgg cagtggttct    660
gggagagatt cttctttcac tatcagcagc ctggaatccg aagatattgg atcttattac    720
tgtcaacagt attataacta tccgtggacg ttcggacctg gcaccaagct ggaaatcaaa    780
cgg                                                                 783

<210> SEQ ID NO 4
<211> LENGTH: 261
<212> TYPE: PRT
<213> ORGANISM: Artificial Sequence
<220> FEATURE:
<223> OTHER INFORMATION: scFv C11

<400> SEQUENCE: 4

Met Glu Trp Thr Trp Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Lys Ser Leu Lys Leu Ser Cys Glu Ala Ser Gly Phe Thr Phe
        35                  40                  45

Ser Gly Tyr Gly Met His Trp Val Arg Gln Ala Pro Gly Arg Gly Leu
    50                  55                  60

Glu Ser Val Ala Tyr Ile Thr Ser Ser Ser Ile Asn Ile Lys Tyr Ala
65                  70                  75                  80

Asp Ala Val Lys Gly Arg Phe Thr Val Ser Arg Asp Asn Ala Lys Asn
                85                  90                  95
```

| Leu | Leu | Phe | Leu | Gln | Met | Asn | Ile | Leu | Lys | Ser | Glu | Asp | Thr | Ala | Met |
|---|---|---|---|---|---|---|---|---|---|---|---|---|---|---|---|
| | | | 100 | | | | 105 | | | | | 110 | | | |

Tyr Tyr Cys Ala Arg Phe Asp Trp Asp Lys Asn Tyr Trp Gly Gln Gly
      115               120                   125

Thr Met Val Thr Val Ser Ser Ala Gly Gly Gly Ser Gly Gly Gly
    130                 135              140

Gly Ser Gly Gly Gly Ser Glu Phe Asp Ile Gln Met Thr Gln Ser
145            150              155            160

Pro Ser Ser Leu Pro Ala Ser Leu Gly Asp Arg Val Thr Ile Asn Cys
            165            170             175

Gln Ala Ser Gln Asp Ile Ser Asn Tyr Leu Asn Trp Tyr Gln Gln Lys
        180              185            190

Pro Gly Lys Ala Pro Lys Leu Leu Ile Tyr Tyr Thr Asn Lys Leu Ala
       195             200            205

Asp Gly Val Pro Ser Arg Phe Ser Gly Ser Gly Ser Gly Arg Asp Ser
    210               215             220

Ser Phe Thr Ile Ser Ser Leu Glu Ser Glu Asp Ile Gly Ser Tyr Tyr
225            230            235            240

Cys Gln Gln Tyr Tyr Asn Tyr Pro Trp Thr Phe Gly Pro Gly Thr Lys
        245              250            255

Leu Glu Ile Lys Arg
       260

<210> SEQ ID NO 5
<211> LENGTH: 831
<212> TYPE: DNA
<213> ORGANISM: Artificial Sequence
<220> FEATURE:
<223> OTHER INFORMATION: scFv C25

<400> SEQUENCE: 5

```
atggaatgga cctgggtctt tctcttcctc ctgtcagtaa ctgcaggtgt ccactcccag    60
gtacagctgc agcagtcagg tccaggactg gtgaagccct cgcagaccct ctcactcacc   120
tgtgccatct ccggggacag tgtctctagc aacaggggtg cttggaactg gatccggcag   180
tccccatcga gaggccttga gtggctggga aggacatact acaggtccag gtggattaat   240
gattatgcag tatctgtgaa aagtcgaata accgtcaacc cagacacatc caagaaccag   300
ttctccctgc agctgaattc tgtgactccc gaggacacgg ctgtgtatta ctgtgcaaga   360
gggcagcagg agaggtacga ccctgggggc cagggaaccc tggtcaccgt ctcgtcaggg   420
agtgcatccg ccccaaccgg aattctagga tccggtggcg gtggcagcgg cggtggtggt   480
tccggggggcg gcggttcttc ctatgtgctg actcagccac cctcagcgtc tgggaccccc   540
gggcagaggg tcaccatctc ttgttctgga agcagttcca acatcggaag gaaaggtgta   600
tattggtttc agcagctccc aggaacggcc cccaaagtcc tcatttatgg gaataatcag   660
cggccggtcag gggtccctga ccgattctct ggctccagat ctggcacctc aggctccctg   720
gccatcagtg gactccggtc cgaggatgag gctgattatt actgtgcagc atgggatgac   780
agcctgaatg gtcctgtgtt cggaggaggc acccagctga ccgtcctctc c             831
```

<210> SEQ ID NO 6
<211> LENGTH: 277
<212> TYPE: PRT
<213> ORGANISM: Artificial Sequence
<220> FEATURE:
<223> OTHER INFORMATION: scFv C25

<400> SEQUENCE: 6

```
Met Glu Trp Thr Trp Val Phe Leu Phe Leu Leu Ser Val Thr Ala Gly
1               5                   10                  15

Val His Ser Gln Val Gln Leu Gln Gln Ser Gly Pro Gly Leu Val Lys
            20                  25                  30

Pro Ser Gln Thr Leu Ser Leu Thr Cys Ala Ile Ser Gly Asp Ser Val
        35                  40                  45

Ser Ser Asn Arg Gly Ala Trp Asn Trp Ile Arg Gln Ser Pro Ser Arg
    50                  55                  60

Gly Leu Glu Trp Leu Gly Arg Thr Tyr Tyr Arg Ser Arg Trp Ile Asn
65                  70                  75                  80

Asp Tyr Ala Val Ser Val Lys Ser Arg Ile Thr Val Asn Pro Asp Thr
                85                  90                  95

Ser Lys Asn Gln Phe Ser Leu Gln Leu Asn Ser Val Thr Pro Glu Asp
            100                 105                 110

Thr Ala Val Tyr Tyr Cys Ala Arg Gly Gln Gln Glu Arg Tyr Asp Pro
        115                 120                 125

Trp Gly Gln Gly Thr Leu Val Thr Val Ser Ser Gly Ser Ala Ser Ala
    130                 135                 140

Pro Thr Gly Ile Leu Gly Ser Gly Gly Gly Gly Ser Gly Gly Gly Gly
145                 150                 155                 160

Ser Gly Gly Gly Gly Ser Ser Tyr Val Leu Thr Gln Pro Pro Ser Ala
                165                 170                 175

Ser Gly Thr Pro Gly Gln Arg Val Thr Ile Ser Cys Ser Gly Ser Ser
            180                 185                 190

Ser Asn Ile Gly Arg Lys Gly Val Tyr Trp Phe Gln Gln Leu Pro Gly
        195                 200                 205

Thr Ala Pro Lys Val Leu Ile Tyr Gly Asn Asn Gln Arg Arg Ser Gly
    210                 215                 220

Val Pro Asp Arg Phe Ser Gly Ser Arg Ser Gly Thr Ser Gly Ser Leu
225                 230                 235                 240

Ala Ile Ser Gly Leu Arg Ser Glu Asp Glu Ala Asp Tyr Tyr Cys Ala
                245                 250                 255

Ala Trp Asp Asp Ser Leu Asn Gly Pro Val Phe Gly Gly Gly Thr Gln
            260                 265                 270

Leu Thr Val Leu Ser
        275
```

<210> SEQ ID NO 7
<211> LENGTH: 816
<212> TYPE: DNA
<213> ORGANISM: Artificial Sequence
<220> FEATURE:
<223> OTHER INFORMATION: scFv C8

<400> SEQUENCE: 7

```
atggaatgga cctgggtctt tctcttcctc ctgtcagtaa ctgcaggtgt ccactccgag    60
gtgcagctga tggagtctgg gggaggcgtg gtccagcctg gggggtccct gagactctcc   120
tgtgcaggct ctgggttcac cgtcagcagc aacttcatga gctgggtccg ccaggctcca   180
gggaagggtc tggagtgggt ctcacttatt tatagcgatg gtagcggtgg taacacatac   240
tacgcagact ccgtgaaggg ccgattcacc gtctccagag acaattccaa gaacacgctg   300
tatcttcaaa tgaacagcct gagagaagag gacacggccc tgtattactg tgcgagagta   360
```

```
tctcgtaggc gtagtggtag actattcgat ctctggggcc gtggtaccct ggtcactgtc    420
tcctcaggaa ttctaggatc cggtggcggt ggcagcggcg gtggtggttc cggaggcggc    480
ggttctcagt ctgctctgac tcagcctccc tccgcgtccg gtctcctgg acagtcagtc     540 accatctcct gcactggaac cagcagtgac gttggtggtt ctaattatgt ctcctggtac    600
caacagcacc caggcaaagt ccccaaactc ataatttatg aggtcagtaa gcggccctca    660
ggggtccctg atcgcttctc tggctccaag tctggcaaca cggcctccct gaccgtctct    720
gggctccagg ctgaggatga ggctgattat tactgcagct catatgcagg cggcaagaag    780
gtgttcggcg agggaccaa gctcaccgtc ctctcc                                816
```

<210> SEQ ID NO 8
<211> LENGTH: 272
<212> TYPE: PRT
<213> ORGANISM: Artificial Sequence
<220> FEATURE:
<223> OTHER INFORMATION: scFv C8

<400> SEQUENCE: 8

```
Met Glu Trp Thr Trp Val Phe Leu Phe Leu Leu Ser Val Thr Ala Gly
1               5                   10                  15

Val His Ser Glu Val Gln Leu Met Glu Ser Gly Gly Gly Val Val Gln
            20                  25                  30

Pro Gly Gly Ser Leu Arg Leu Ser Cys Ala Gly Ser Gly Phe Thr Val
        35                  40                  45

Ser Ser Asn Phe Met Ser Trp Val Arg Gln Ala Pro Gly Lys Gly Leu
    50                  55                  60

Glu Trp Val Ser Leu Ile Tyr Ser Asp Gly Ser Gly Asn Thr Tyr
65                  70                  75                  80

Tyr Ala Asp Ser Val Lys Gly Arg Phe Thr Val Ser Arg Asp Asn Ser
                85                  90                  95

Lys Asn Thr Leu Tyr Leu Gln Met Asn Ser Leu Arg Glu Glu Asp Thr
            100                 105                 110

Ala Leu Tyr Tyr Cys Ala Arg Val Ser Arg Arg Ser Gly Arg Leu
        115                 120                 125

Phe Asp Leu Trp Gly Arg Gly Thr Leu Val Thr Val Ser Ser Gly Ile
    130                 135                 140

Leu Gly Ser Gly Gly Gly Gly Ser Gly Gly Gly Gly Ser Gly Gly Gly
145                 150                 155                 160

Gly Ser Gln Ser Ala Leu Thr Gln Pro Pro Ser Ala Ser Gly Ser Pro
                165                 170                 175

Gly Gln Ser Val Thr Ile Ser Cys Thr Gly Thr Ser Ser Asp Val Gly
            180                 185                 190

Gly Ser Asn Tyr Val Ser Trp Tyr Gln Gln His Pro Gly Lys Val Pro
        195                 200                 205

Lys Leu Ile Ile Tyr Glu Val Ser Lys Arg Pro Ser Gly Val Pro Asp
    210                 215                 220

Arg Phe Ser Gly Ser Lys Ser Gly Asn Thr Ala Ser Leu Thr Val Ser
225                 230                 235                 240

Gly Leu Gln Ala Glu Asp Glu Ala Asp Tyr Tyr Cys Ser Ser Tyr Ala
                245                 250                 255

Gly Gly Lys Lys Val Phe Gly Gly Gly Thr Lys Leu Thr Val Leu Ser
            260                 265                 270
```

```
<210> SEQ ID NO 9
<211> LENGTH: 124
<212> TYPE: PRT
<213> ORGANISM: Artificial Sequence
<220> FEATURE:
<223> OTHER INFORMATION: scFv B2 Variable Heavy Region

<400> SEQUENCE: 9

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Thr Asn
65                  70                  75                  80

Gln Phe Ser Leu Gln Leu Asn Ser Val Thr Pro Asp Asp Thr Ala Val
                85                  90                  95

Tyr Tyr Cys Ala Arg Glu Gly Ala His Glu Trp Ala Asp Ala Phe Asp
            100                 105                 110

Ile Trp Gly Gln Gly Thr Met Val Thr Val Ser Ser
        115                 120

<210> SEQ ID NO 10
<211> LENGTH: 108
<212> TYPE: PRT
<213> ORGANISM: Artificial Sequence
<220> FEATURE:
<223> OTHER INFORMATION: scFv B2 Variable Light Region

<400> SEQUENCE: 10

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Pro Arg Phe Ser Gly
    50                  55                  60

Ser Gly Ser Gly Thr Ala Phe Thr Phe Thr Ile Ser Ser Leu Gln Pro
65                  70                  75                  80

Glu Asp Phe Ala Thr Tyr Tyr Cys Gln Gln Tyr Asp Asn Leu Pro His
                85                  90                  95

Thr Phe Gly Pro Gly Thr Lys Val Asp Ile Lys Ser
            100                 105

<210> SEQ ID NO 11
<211> LENGTH: 116
<212> TYPE: PRT
<213> ORGANISM: Artificial Sequence
<220> FEATURE:
<223> OTHER INFORMATION: scFv C11 Variable Heavy Region

<400> SEQUENCE: 11

Glu Val Gln Leu Val Glu Ser Gly Gly Gly Leu Val Gln Pro Gly Lys
1               5                   10                  15

Ser Leu Lys Leu Ser Cys Glu Ala Ser Gly Phe Thr Phe Ser Gly Tyr
            20                  25                  30
```

```
Gly Met His Trp Val Arg Gln Ala Pro Gly Arg Gly Leu Glu Ser Val
         35                  40                  45

Ala Tyr Ile Thr Ser Ser Ser Ile Asn Ile Lys Tyr Ala Asp Ala Val
 50                  55                  60

Lys Gly Arg Phe Thr Val Ser Arg Asp Asn Ala Lys Asn Leu Leu Phe
 65                  70                  75                  80

Leu Gln Met Asn Ile Leu Lys Ser Glu Asp Thr Ala Met Tyr Tyr Cys
                 85                  90                  95

Ala Arg Phe Asp Trp Asp Lys Asn Tyr Trp Gly Gln Gly Thr Met Val
                100                 105                 110

Thr Val Ser Ser
        115

<210> SEQ ID NO 12
<211> LENGTH: 110
<212> TYPE: PRT
<213> ORGANISM: Artificial Sequence
<220> FEATURE:
<223> OTHER INFORMATION: scFv C11 Variable Light Region

<400> SEQUENCE: 12

Glu Phe Asp Ile Gln Met Thr Gln Ser Pro Ser Ser Leu Pro Ala Ser
 1               5                  10                  15

Leu Gly Asp Arg Val Thr Ile Asn Cys Gln Ala Ser Gln Asp Ile Ser
                20                  25                  30

Asn Tyr Leu Asn Trp Tyr Gln Gln Lys Pro Gly Lys Ala Pro Lys Leu
             35                  40                  45

Leu Ile Tyr Tyr Thr Asn Lys Leu Ala Asp Gly Val Pro Ser Arg Phe
 50                  55                  60

Ser Gly Ser Gly Ser Gly Arg Asp Ser Ser Phe Thr Ile Ser Ser Leu
 65                  70                  75                  80

Glu Ser Glu Asp Ile Gly Ser Tyr Tyr Cys Gln Gln Tyr Tyr Asn Tyr
                 85                  90                  95

Pro Trp Thr Phe Gly Pro Gly Thr Lys Leu Glu Ile Lys Arg
                100                 105                 110

<210> SEQ ID NO 13
<211> LENGTH: 132
<212> TYPE: PRT
<213> ORGANISM: Artificial Sequence
<220> FEATURE:
<223> OTHER INFORMATION: scFv C25 Variable Heavy Region

<400> SEQUENCE: 13

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
                20                  25                  30

Arg Gly Ala Trp Asn Trp Ile Arg Gln Ser Pro Ser Arg Gly Leu Glu
             35                  40                  45

Trp Leu Gly Arg Thr Tyr Tyr Arg Ser Arg Trp Ile Asn Asp Tyr Ala
 50                  55                  60

Val Ser Val Lys Ser Arg Ile Thr Val Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Gly Gln Gln Glu Arg Tyr Asp Pro Trp Gly Gln
                100                 105                 110
```

```
Gly Thr Leu Val Thr Val Ser Ser Gly Ser Ala Ser Ala Pro Thr Gly
        115                 120                 125

Ile Leu Gly Ser
        130

<210> SEQ ID NO 14
<211> LENGTH: 111
<212> TYPE: PRT
<213> ORGANISM: Artificial Sequence
<220> FEATURE:
<223> OTHER INFORMATION: scFv C25 Variable Light Region

<400> SEQUENCE: 14

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Lys
            20                  25                  30

Gly Val Tyr Trp Phe Gln Gln Leu Pro Gly Thr Ala Pro Lys Val Leu
        35                  40                  45

Ile Tyr Gly Asn Asn Gln Arg Arg Ser Gly Val Pro Asp Arg Phe Ser
    50                  55                  60

Gly Ser Arg Ser Gly Thr Ser Gly Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Gln Leu Thr Val Leu Ser
            100                 105                 110

<210> SEQ ID NO 15
<211> LENGTH: 123
<212> TYPE: PRT
<213> ORGANISM: Artificial Sequence
<220> FEATURE:
<223> OTHER INFORMATION: scFv C8 Variable Heavy Region

<400> SEQUENCE: 15

Glu Val Gln Leu Met Glu Ser Gly Gly Gly Val Val Gln Pro Gly Gly
1               5                   10                  15

Ser Leu Arg Leu Ser Cys Ala Gly Ser Gly Phe Thr Val Ser Ser Asn
            20                  25                  30

Phe Met Ser Trp Val Arg Gln Ala Pro Gly Lys Gly Leu Glu Trp Val
        35                  40                  45

Ser Leu Ile Tyr Ser Asp Gly Ser Gly Asn Thr Tyr Tyr Ala Asp
    50                  55                  60

Ser Val Lys Gly Arg Phe Thr Val Ser Arg Asp Asn Ser Lys Asn Thr
65                  70                  75                  80

Leu Tyr Leu Gln Met Asn Ser Leu Arg Glu Glu Asp Thr Ala Leu Tyr
                85                  90                  95

Tyr Cys Ala Arg Val Ser Arg Arg Ser Gly Arg Leu Phe Asp Leu
            100                 105                 110

Trp Gly Arg Gly Thr Leu Val Thr Val Ser Ser
        115                 120

<210> SEQ ID NO 16
<211> LENGTH: 110
<212> TYPE: PRT
<213> ORGANISM: Artificial Sequence
<220> FEATURE:
<223> OTHER INFORMATION: scFv C8 Variable Light Region
```

```
<400> SEQUENCE: 16

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Ser
            20                  25                  30

Asn Tyr Val Ser Trp Tyr Gln Gln His Pro Gly Lys Val Pro Lys Leu
        35                  40                  45

Ile Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Gly
                85                  90                  95

Lys Lys Val Phe Gly Gly Gly Thr Lys Leu Thr Val Leu Ser
            100                 105                 110

<210> SEQ ID NO 17
<211> LENGTH: 12
<212> TYPE: PRT
<213> ORGANISM: Artificial Sequence
<220> FEATURE:
<223> OTHER INFORMATION: Variable Heavy Region CDR 1
<220> FEATURE:
<221> NAME/KEY: misc_feature
<222> LOCATION: (8)..(8)
<223> OTHER INFORMATION: Xaa may be Ser or Arg
<220> FEATURE:
<221> NAME/KEY: misc_feature
<222> LOCATION: (9)..(9)
<223> OTHER INFORMATION: Xaa may be Ala or Gly

<400> SEQUENCE: 17

Gly Asp Ser Val Ser Ser Asn Xaa Xaa Ala Trp Asn
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Variable Heavy Region CDR 1
<220> FEATURE:
<221> NAME/KEY: misc_feature
<222> LOCATION: (4)..(4)
<223> OTHER INFORMATION: Xaa may be Val or Phe
<220> FEATURE:
<221> NAME/KEY: misc_feature
<222> LOCATION: (6)..(6)
<223> OTHER INFORMATION: Xaa may be Ser or Gly
<220> FEATURE:
<221> NAME/KEY: misc_feature
<222> LOCATION: (7)..(7)
<223> OTHER INFORMATION: Xaa may be Asn or Tyr
<220> FEATURE:
<221> NAME/KEY: misc_feature
<222> LOCATION: (8)..(8)
<223> OTHER INFORMATION: Xaa may be Phe or Gly
<220> FEATURE:
<221> NAME/KEY: misc_feature
<222> LOCATION: (10)..(10)
<223> OTHER INFORMATION: Xaa may be Ser or His

<400> SEQUENCE: 18

Gly Phe Thr Xaa Ser Xaa Xaa Xaa Met Xaa
1               5                   10
```

```
<210> SEQ ID NO 19
<211> LENGTH: 8
<212> TYPE: PRT
<213> ORGANISM: Artificial Sequence
<220> FEATURE:
<223> OTHER INFORMATION: Variable Heavy Region CDR2
<220> FEATURE:
<221> NAME/KEY: misc_feature
<222> LOCATION: (5)..(5)
<223> OTHER INFORMATION: Xaa may be Lys or Arg
<220> FEATURE:
<221> NAME/KEY: misc_feature
<222> LOCATION: (7)..(7)
<223> OTHER INFORMATION: Xaa may be Tyr or Ile
<220> FEATURE:
<221> NAME/KEY: misc_feature
<222> LOCATION: (8)..(8)
<223> OTHER INFORMATION: Xaa may be Asn or absent

<400> SEQUENCE: 19

Tyr Tyr Arg Ser Xaa Trp Xaa Xaa
1               5

<210> SEQ ID NO 20
<211> LENGTH: 6
<212> TYPE: PRT
<213> ORGANISM: Artificial Sequence
<220> FEATURE:
<223> OTHER INFORMATION: Variable Heavy Region CDR2

<400> SEQUENCE: 20

Thr Ser Ser Ser Ile Asn
1               5

<210> SEQ ID NO 21
<211> LENGTH: 8
<212> TYPE: PRT
<213> ORGANISM: Artificial Sequence
<220> FEATURE:
<223> OTHER INFORMATION: Variable Heavy Region CDR2

<400> SEQUENCE: 21

Tyr Ser Asp Gly Ser Gly Gly Asn
1               5

<210> SEQ ID NO 22
<211> LENGTH: 12
<212> TYPE: PRT
<213> ORGANISM: Artificial Sequence
<220> FEATURE:
<223> OTHER INFORMATION: Variable Heavy Region CDR3

<400> SEQUENCE: 22

Glu Gly Ala His Glu Trp Ala Asp Ala Phe Asp Ile
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Variable Heavy Region CDR3

<400> SEQUENCE: 23

Phe Asp Trp Asp Lys Asn Tyr
1               5
```

```
<210> SEQ ID NO 24
<211> LENGTH: 8
<212> TYPE: PRT
<213> ORGANISM: Artificial Sequence
<220> FEATURE:
<223> OTHER INFORMATION: Variable Heavy Region CDR3

<400> SEQUENCE: 24

Gly Gln Gln Glu Arg Tyr Asp Pro
1               5

<210> SEQ ID NO 25
<211> LENGTH: 12
<212> TYPE: PRT
<213> ORGANISM: Artificial Sequence
<220> FEATURE:
<223> OTHER INFORMATION: Variable Heavy Region CDR3

<400> SEQUENCE: 25

Val Ser Arg Arg Arg Ser Gly Arg Leu Phe Asp Leu
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Variable Light Region CDR 1

<400> SEQUENCE: 26

Gln Ala Ser Gln Asp Ile Ser Asn Tyr Leu Asn
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Variable Light Region CDR 1
<220> FEATURE:
<221> NAME/KEY: misc_feature
<222> LOCATION: (1)..(1)
<223> OTHER INFORMATION: Xaa may be Thr or Ser
<220> FEATURE:
<221> NAME/KEY: misc_feature
<222> LOCATION: (3)..(3)
<223> OTHER INFORMATION: Xaa may be Thr or Ser
<220> FEATURE:
<221> NAME/KEY: misc_feature
<222> LOCATION: (6)..(6)
<223> OTHER INFORMATION: Xaa may be Asp or Asn
<220> FEATURE:
<221> NAME/KEY: misc_feature
<222> LOCATION: (7)..(7)
<223> OTHER INFORMATION: Xaa may be Val or Ile
<220> FEATURE:
<221> NAME/KEY: misc_feature
<222> LOCATION: (9)..(9)
<223> OTHER INFORMATION: Xaa may be Gly or absent
<220> FEATURE:
<221> NAME/KEY: misc_feature
<222> LOCATION: (10)..(10)
<223> OTHER INFORMATION: Xaa may be Ser or Arg
<220> FEATURE:
<221> NAME/KEY: misc_feature
<222> LOCATION: (11)..(11)
<223> OTHER INFORMATION: Xaa may be Asn or Lys
<220> FEATURE:
<221> NAME/KEY: misc_feature
<222> LOCATION: (12)..(12)
<223> OTHER INFORMATION: Xaa may be Tyr or Gly
```

```
<220> FEATURE:
<221> NAME/KEY: misc_feature
<222> LOCATION: (14)..(14)
<223> OTHER INFORMATION: Xaa may be Ser or Tyr

<400> SEQUENCE: 27

Xaa Gly Xaa Ser Ser Xaa Xaa Gly Xaa Xaa Xaa Xaa Val Xaa
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Variable Light Region CDR 2

<400> SEQUENCE: 28

Asp Ala Ser Asn Leu Glu Thr
1               5

<210> SEQ ID NO 29
<211> LENGTH: 7
<212> TYPE: PRT
<213> ORGANISM: Artificial Sequence
<220> FEATURE:
<223> OTHER INFORMATION: Variable Light Region CDR 2

<400> SEQUENCE: 29

Tyr Thr Asn Lys Leu Ala Asp
1               5

<210> SEQ ID NO 30
<211> LENGTH: 7
<212> TYPE: PRT
<213> ORGANISM: Artificial Sequence
<220> FEATURE:
<223> OTHER INFORMATION: Variable Light Region CDR 2

<400> SEQUENCE: 30

Gly Asn Asn Gln Arg Arg Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Variable Light Region CDR 2

<400> SEQUENCE: 31

Glu Val Ser Lys Arg Pro Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Variable Light Region CDR3
<220> FEATURE:
<221> NAME/KEY: misc_feature
<222> LOCATION: (4)..(4)
<223> OTHER INFORMATION: Xaa may be Asp or Tyr
<220> FEATURE:
<221> NAME/KEY: misc_feature
<222> LOCATION: (6)..(6)
<223> OTHER INFORMATION: Xaa may be Leu or Tyr
```

```
<220> FEATURE:
<221> NAME/KEY: misc_feature
<222> LOCATION: (8)..(8)
<223> OTHER INFORMATION: Xaa may be His or Trp

<400> SEQUENCE: 32

Gln Gln Tyr Xaa Asn Xaa Pro Xaa Thr
1               5

<210> SEQ ID NO 33
<211> LENGTH: 11
<212> TYPE: PRT
<213> ORGANISM: Artificial Sequence
<220> FEATURE:
<223> OTHER INFORMATION: Variable Light Region CDR3

<400> SEQUENCE: 33

Ala Ala Trp Asp Asp Ser Leu Asn Gly Pro Val
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Variable Light Region CDR3

<400> SEQUENCE: 34

Ser Ser Tyr Ala Gly Gly Lys Lys Val
1               5

<210> SEQ ID NO 35
<211> LENGTH: 12
<212> TYPE: PRT
<213> ORGANISM: Artificial Sequence
<220> FEATURE:
<223> OTHER INFORMATION: scFv B2 Variable Heavy Region CDR1

<400> SEQUENCE: 35

Gly Asp Ser Val Ser Ser Asn Ser Ala Ala Trp Asn
1               5                   10

<210> SEQ ID NO 36
<211> LENGTH: 8
<212> TYPE: PRT
<213> ORGANISM: Artificial Sequence
<220> FEATURE:
<223> OTHER INFORMATION: scFv B2 Variable Heavy Region CDR 2

<400> SEQUENCE: 36

Tyr Tyr Arg Ser Lys Trp Tyr Asn
1               5

<210> SEQ ID NO 37
<211> LENGTH: 9
<212> TYPE: PRT
<213> ORGANISM: Artificial Sequence
<220> FEATURE:
<223> OTHER INFORMATION: scFv B2 Variable Light Region CDR 3

<400> SEQUENCE: 37

Gln Gln Tyr Asp Asn Leu Pro His Thr
1               5
```

-continued

```
<210> SEQ ID NO 38
<211> LENGTH: 10
<212> TYPE: PRT
<213> ORGANISM: Artificial Sequence
<220> FEATURE:
<223> OTHER INFORMATION: scFv C11 Variable Heavy Region CDR1

<400> SEQUENCE: 38

Gly Phe Thr Phe Ser Gly Tyr Gly Met His
1               5                   10

<210> SEQ ID NO 39
<211> LENGTH: 9
<212> TYPE: PRT
<213> ORGANISM: Artificial Sequence
<220> FEATURE:
<223> OTHER INFORMATION: scFv C11 Variable Light Region CDR3

<400> SEQUENCE: 39

Gln Gln Tyr Tyr Asn Tyr Pro Trp Thr
1               5

<210> SEQ ID NO 40
<211> LENGTH: 12
<212> TYPE: PRT
<213> ORGANISM: Artificial Sequence
<220> FEATURE:
<223> OTHER INFORMATION: scFv C25 Variable Heavy Region CDR1

<400> SEQUENCE: 40

Gly Asp Ser Val Ser Ser Asn Arg Gly Ala Trp Asn
1               5                   10

<210> SEQ ID NO 41
<211> LENGTH: 7
<212> TYPE: PRT
<213> ORGANISM: Artificial Sequence
<220> FEATURE:
<223> OTHER INFORMATION: scFv C25 Variable Heavy Region CDR2

<400> SEQUENCE: 41

Tyr Tyr Arg Ser Arg Trp Ile
1               5

<210> SEQ ID NO 42
<211> LENGTH: 13
<212> TYPE: PRT
<213> ORGANISM: Artificial Sequence
<220> FEATURE:
<223> OTHER INFORMATION: scFv C25 Variable Light Region CDR1

<400> SEQUENCE: 42

Ser Gly Ser Ser Ser Asn Ile Gly Arg Lys Gly Val Tyr
1               5                   10

<210> SEQ ID NO 43
<211> LENGTH: 10
<212> TYPE: PRT
<213> ORGANISM: Artificial Sequence
<220> FEATURE:
<223> OTHER INFORMATION: scFv C8 Variable Heavy Region CDR1

<400> SEQUENCE: 43

Gly Phe Thr Val Ser Ser Asn Phe Met Ser
1               5                   10
```

```
<210> SEQ ID NO 44
<211> LENGTH: 14
<212> TYPE: PRT
<213> ORGANISM: Artificial Sequence
<220> FEATURE:
<223> OTHER INFORMATION: scFv C8 Variable Light Region CDR1

<400> SEQUENCE: 44

Thr Gly Thr Ser Ser Asp Val Gly Gly Ser Asn Tyr Val Ser
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Anti-CD3 Antigen Binding Fragment Heavy Chain
      Variable Region CDR1

<400> SEQUENCE: 45

Ser Gly Tyr Thr Phe Thr Arg Tyr Thr Met His
1               5                   10

<210> SEQ ID NO 46
<211> LENGTH: 17
<212> TYPE: PRT
<213> ORGANISM: Artificial Sequence
<220> FEATURE:
<223> OTHER INFORMATION: Anti-CD3 Antigen Binding Fragment Heavy Chain
      Variable Region CDR2

<400> SEQUENCE: 46

Tyr Ile Asn Pro Ser Arg Gly Tyr Thr Asn Tyr Asn Gln Lys Phe Lys
1               5                   10                  15

Asp

<210> SEQ ID NO 47
<211> LENGTH: 8
<212> TYPE: PRT
<213> ORGANISM: Artificial Sequence
<220> FEATURE:
<223> OTHER INFORMATION: Anti-CD3 Antigen Binding Fragment Heavy Chain
      Variable Region CDR3

<400> SEQUENCE: 47

Tyr Tyr Asp Asp His Tyr Cys Leu
1               5

<210> SEQ ID NO 48
<211> LENGTH: 10
<212> TYPE: PRT
<213> ORGANISM: Artificial Sequence
<220> FEATURE:
<223> OTHER INFORMATION: Anti-CD3 Antigen Binding Fragment Light Chain
      Variable Region CDR1

<400> SEQUENCE: 48

Ser Ala Ser Ser Ser Val Ser Tyr Met Asn
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Anti-CD3 Antigen Binding Fragment Light Chain
      Variable Region CDR2
```

```
<400> SEQUENCE: 49

Asp Thr Ser Lys Leu Ala Ser
1               5

<210> SEQ ID NO 50
<211> LENGTH: 8
<212> TYPE: PRT
<213> ORGANISM: Artificial Sequence
<220> FEATURE:
<223> OTHER INFORMATION: Anti-CD3 Antigen Binding Fragment Light Chain
      Variable Region CDR3

<400> SEQUENCE: 50

Gln Gln Trp Ser Ser Asn Pro Phe
1               5

<210> SEQ ID NO 51
<211> LENGTH: 15
<212> TYPE: PRT
<213> ORGANISM: Artificial Sequence
<220> FEATURE:
<223> OTHER INFORMATION: Linker Example

<400> SEQUENCE: 51

Gly Gly Gly Gly Ser Gly Gly Gly Gly Ser Gly Gly Gly Gly Ser
1               5                   10                  15

<210> SEQ ID NO 52
<211> LENGTH: 10
<212> TYPE: PRT
<213> ORGANISM: Artificial Sequence
<220> FEATURE:
<223> OTHER INFORMATION: Linker Example

<400> SEQUENCE: 52

Ser Ala Lys Thr Thr Pro Lys Leu Gly Gly
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Linker Example

<400> SEQUENCE: 53

Arg Ala Asp Ala Ala Pro Thr Val Ser
1               5

<210> SEQ ID NO 54
<211> LENGTH: 12
<212> TYPE: PRT
<213> ORGANISM: Artificial Sequence
<220> FEATURE:
<223> OTHER INFORMATION: Linker Example

<400> SEQUENCE: 54

Arg Ala Asp Ala Ala Ala Ala Gly Gly Pro Gly Ser
1               5                   10

<210> SEQ ID NO 55
<211> LENGTH: 27
<212> TYPE: PRT
<213> ORGANISM: Artificial Sequence
<220> FEATURE:
<223> OTHER INFORMATION: Linker Example
```

<400> SEQUENCE: 55

Arg Ala Asp Ala Ala Ala Gly Gly Gly Gly Ser Gly Gly Gly
1               5                   10                  15

Ser Gly Gly Gly Gly Ser Gly Gly Gly Ser
            20                  25

<210> SEQ ID NO 56
<211> LENGTH: 113
<212> TYPE: PRT
<213> ORGANISM: Homo sapiens

<400> SEQUENCE: 56

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 57
<211> LENGTH: 86
<212> TYPE: PRT
<213> ORGANISM: Homo sapiens

<400> SEQUENCE: 57

Val Lys Gly Lys His Leu Cys Pro Ser Pro Leu Phe Pro Gly Pro Ser
1               5                   10                  15

Lys Pro Phe Trp Val Leu Val Val Val Gly Gly Val Leu Ala Cys Tyr
            20                  25                  30

Ser Leu Leu Val Thr Val Ala Phe Ile Ile Phe Trp Val Arg Ser Lys
        35                  40                  45

Arg Ser Arg Leu Leu His Ser Asp Tyr Met Asn Met Thr Pro Arg Arg
    50                  55                  60

Pro Gly Pro Thr Arg Lys His Tyr Gln Pro Tyr Ala Pro Pro Arg Asp
65                  70                  75                  80

Phe Ala Ala Tyr Arg Ser
                85

<210> SEQ ID NO 58
<211> LENGTH: 327
<212> TYPE: PRT
<213> ORGANISM: Homo sapiens

<400> SEQUENCE: 58

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr
                325

<210> SEQ ID NO 59
<211> LENGTH: 63
<212> TYPE: PRT
<213> ORGANISM: Foot-and-mouth disease virus

<400> SEQUENCE: 59

Gly Ser Gly Ser Arg Val Thr Glu Leu Leu Tyr Arg Met Lys Arg Ala
1               5                   10                  15

Glu Thr Tyr Cys Pro Arg Pro Leu Leu Ala Ile His Pro Thr Glu Ala
            20                  25                  30

Arg His Lys Gln Lys Ile Val Ala Pro Val Lys Gln Leu Leu Asn Phe
        35                  40                  45

Asp Leu Leu Lys Leu Ala Gly Asp Val Glu Ser Asn Pro Gly Pro
    50                  55                  60

<210> SEQ ID NO 60
<211> LENGTH: 25
<212> TYPE: PRT
<213> ORGANISM: Strongylocentrotus purpurates

<400> SEQUENCE: 60

Asp Gly Phe Cys Ile Leu Tyr Leu Leu Leu Ile Leu Leu Met Arg Ser
1               5                   10                  15

Gly Asp Val Glu Thr Asn Pro Gly Pro
            20                  25

<210> SEQ ID NO 61
<211> LENGTH: 20
<212> TYPE: PRT
<213> ORGANISM: Amphimedon queenslandica

<400> SEQUENCE: 61

Leu Leu Cys Phe Met Leu Leu Leu Leu Ser Gly Asp Val Glu Leu
1               5                   10                  15

Asn Pro Gly Pro
            20

<210> SEQ ID NO 62
<211> LENGTH: 20
<212> TYPE: PRT
<213> ORGANISM: Amphimedon queenslandica

<400> SEQUENCE: 62

His His Phe Met Phe Leu Leu Leu Leu Ala Gly Asp Ile Glu Leu
1               5                   10                  15

Asn Pro Gly Pro
            20

<210> SEQ ID NO 63
<211> LENGTH: 20
<212> TYPE: PRT
<213> ORGANISM: Saccoglossus kowalevskii

<400> SEQUENCE: 63

Trp Phe Leu Val Leu Leu Ser Phe Ile Leu Ser Gly Asp Ile Glu Val
1               5                   10                  15

Asn Pro Gly Pro
            20

<210> SEQ ID NO 64
<211> LENGTH: 20
<212> TYPE: PRT
<213> ORGANISM: Branchiostoma floridae

<400> SEQUENCE: 64

Lys Asn Cys Ala Met Tyr Met Leu Leu Leu Ser Gly Asp Val Glu Thr
1               5                   10                  15

Asn Pro Gly Pro
            20

<210> SEQ ID NO 65
<211> LENGTH: 20
<212> TYPE: PRT
<213> ORGANISM: Branchiostoma floridae

```
<400> SEQUENCE: 65

Met Val Ile Ser Gln Leu Met Leu Lys Leu Ala Gly Asp Val Glu Glu
1               5                   10                  15

Asn Pro Gly Pro
            20

<210> SEQ ID NO 66
<211> LENGTH: 22
<212> TYPE: PRT
<213> ORGANISM: Porcine Teschovirus-1

<400> SEQUENCE: 66

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 67
<211> LENGTH: 21
<212> TYPE: PRT
<213> ORGANISM: Thoseaasigna virus

<400> SEQUENCE: 67

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 68
<211> LENGTH: 23
<212> TYPE: PRT
<213> ORGANISM: Equine Rhinitis A virus

<400> SEQUENCE: 68

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 69
<211> LENGTH: 8
<212> TYPE: PRT
<213> ORGANISM: Artificial Sequence
<220> FEATURE:
<223> OTHER INFORMATION: 2a consensus sequence
<220> FEATURE:
<221> NAME/KEY: misc_feature
<222> LOCATION: (2)..(2)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid

<400> SEQUENCE: 69

Asp Xaa Glu Xaa Asn Pro Gly Pro
1               5

<210> SEQ ID NO 70
<211> LENGTH: 8
<212> TYPE: PRT
<213> ORGANISM: Artificial Sequence
<220> FEATURE:
<223> OTHER INFORMATION: OVA-immunodominant peptide
```

```
<400> SEQUENCE: 70

Ser Ile Ile Asn Phe Glu Lys Leu
1               5
```

ANTI-MICA ANTIGEN BINDING FRAGMENTS, FUSION MOLECULES, CELLS WHICH EXPRESS AND METHODS OF USING

RELATED APPLICATIONS

This application is a 371 National Phase application of International Application No. PCT/US16/24322 filed Mar. 25, 2016, which claims priority to, and incorporates by reference in its entirety both the above mentioned PCT application and, U.S. Provisional Application Ser. No. 62/138,561 filed on Mar. 26, 2015.

This application includes, as part of its disclosure, an electronic biological sequence listing text file having the name "43252o2001.txt" which has a file size of 42,268 bytes and which was created on Sep. 26, 2017, which is hereby incorporated by reference in its entirety.

This invention was made with government support under contract number CA164178 awarded by the National Cancer Institute. The government has certain rights in the invention.

SEQUENCE DISCLOSURE

This application includes, as part of its disclosure, an electronic biological sequence listing text file having the name "1143252o002001.txt" which has a file size of 42,316 bytes and which was created on Jan. 28, 2020, which is hereby incorporated by reference in its entirety.

BACKGROUND OF THE INVENTION

Natural Killer Group 2D (NKG2D) is a member of the NKG2 family of HLA class I C-type lectin receptors and is expressed as a homodimer by natural killer (NK) cells (Burgess, et al. (2008) *Immunol. Res.* 40:18-34; Jonjic, et al. (2008) *Eur. J. Immunol.* 38:2927-68) and cytotoxic lymphocytes (Wrobel, et al. (2007) *Scand. J. Immunol.* 66:320-28; Saez-Borderias, et al. (2006) *Eur. J. Immunol.* 36:3198-06). The ligands for NKG2D are induced-self proteins that are absent or present at very low levels on the surface of normal cells, but can be expressed in increased amounts in infected, transformed, senescent, and stressed cells, and include the human major histocompatibility complex class I chain-related gene A (MICA) and MICB ligands (Mendoza-Rincon (2007) In *Advances in Cancer Research at UNAM*, Mas-Oliva, et al. eds. Mexico City, Manual Moderno, pg. 127-135), which are stress-induced molecules often expressed by various tumors, including those of epithelial origin (Paschen, et al. (2009) *Clin. Cancer Res.* 15:5208-15; Unni, et al. (2008) *Proc. Natl. Acad Sci. USA* 105:1686-91) and leukemias (Kato, et al. (2007) *Leukemia* 21:2103-08), as well as by virus-infected cells (Chalupny, et al. (2006) *Biochem. Biophys. Res. Commun.* 346:175-81; Tosh, et al. (2006) *Hum. Mol. Genet.* 15:2880-87). The recognition of the MICA and MICB ligands on tumor cells by the NKG2D receptor, found on NK cells, induces the cytotoxic activity of NK cells (Santoni, et al. (2007) *Am. J. Reprod Immunol.* 58:280-88) and the subsequent lysis of their tumor targets (Papazahariadou, et al. (2007) *Int. J. Biol. Markers* 22:144-53). The secretion of MICA and MICB by cancer cells has been suggested as a mechanism for tumor cell immune escape through the saturation of NKG2D receptors on cytotoxic cells (Salih, et al. (2006) *Hum. Immunol.* 67:188-95; Marten, et al. (2006) *Int. J. Cancer* 119:2359-65), thus abrogating their ability to recognize tumor cells. In fact, higher amounts of these molecules were found in the sera of human cancer patients compared to healthy individuals (Salih, et al. (2008) *Front. Biosci.* 4A:2041-45), and a direct correlation was found between increased serum concentrations of these molecules and tumor stage (Holdenrieder, et al. (2006) *Cancer Immunol. Immunother.* 55:1584-89). Patients responding to immunotherapy have been shown to mount antibody responses targeting MICA, which permits re-engagement of immunity (May, et al. (2012) *J. Clin. Oncol.* 30(suppl.):abstract 2502). Moreover, antibodies targeting MICA and MICB have been shown to block the MICA/NKG2D interaction and mediate complement-dependent cytotoxicity (CDC) and antibody-dependent cell cytotoxicity (ADCC) toward MICA expressing cells (Bonnafous, et al. (2013) *J. Immuno Ther. Cancer* 1(Suppl 1):P41). See also, WO 2014/144791 and WO 2013/117647.

SUMMARY OF THE INVENTION

The present invention provides antibodies and antigen specific binding fragments which specifically bind to MICA, as well as chimeric antigen receptors ("CARs") or bi-specific T-cell engagers (BiTE®'s) which comprise said anti-MICA antibodies or antigen binding fragments.

The present invention also provides recombinant cells, e.g., T cells or other immune cells which are engineered to express any of the foregoing, and diagnostic or therapeutic compositions containing any of the foregoing.

The present invention also provides methods of therapy and diagnosis using anti-MICA and antigen specific binding fragments, chimeric antigen receptors ("CARs") or bi-specific T-cell engagers (BiTE®'s), which comprise said anti-MICA antibodies or antigen binding fragments, recombinant cells, e.g., T cells or other immune cells which are engineered to express any of the foregoing, in therapeutic or diagnostic methods wherein detecting, inhibiting or blocking the effects of MICA or MICB is therapeutically beneficial, e.g., cancer, autoimmune disorders, inflammatory disease, infection, and transplant rejection. A particularly preferred usage of these antibodies and antigen specific binding fragments, chimeric antigen receptors ("CARs") or bi-specific T-cell engagers (BiTE®'s) and cells which express same is in the treatment of cancer, e.g., cancers characterized by the upregulation or overexpression of MICA antigens.

The subject anti-MICA antibodies or antigen binding fragments may be directly or indirectly attached to other moieties, e.g., immune signaling moieties or other antibodies or antibody fragments. In an exemplary embodiment an anti-MICA or anti-MICB antibody according to the invention is comprised in a chimeric antigen receptor, containing other moieties such as a transmembrane region, an intracellular T-cell receptor signaling domain, (e.g., obtained from CD3 zeta, an FcRγ signaling domain, and/or an intracellular domain of a costimulatory molecule. In another exemplary embodiment the CAR may comprise CD28 sequences, e.g., the CD28 hinge, transmembrane and cytoplasmic domains.

In some embodiments, the antigen binding fragment or CAR or BiTE® may be fused to a label, cytotoxic agent or therapeutic radioisotope.

In some other embodiments, the antigen binding fragment is a component of a chimeric antigen receptor, wherein the antigen binding fragment is fused to a transmembrane region, an intracellular T-cell receptor signaling domain, (e.g., obtained from CD3 zeta) or FcRγ signaling domain, or my comprise the intracellular domain of a costimulatory molecule.

In some exemplary embodiments, an anti-MICA antibody or antigen binding fragment according to the invention mat be comprised within a bi-specific T-cell engager, and the antibody or antigen binding fragment is fused to an antigen binding domain that binds to an immune effector cell antigen, e.g., CD3 or other immune cell antigen such as those identified infra.

In other exemplary embodiments, the invention specifically provides immune cells, e.g., T cells, preferably primary human T cells, or other primary human immune cells which are engineered to express a CAR comprising an anti-MICA antibody or antigen binding fragment according to the invention or a BiTE® comprising same, wherein the CAR or BiTE® may comprise an antibody or antigen binding fragment that binds to an antigen on an immune effector cell, e.g., CD3 or another antigen expressed on an immune effector cell such as are described infra.

In other exemplary embodiments, the invention specifically provides pharmaceutical or diagnostic compositions including an effective amount of antibodies or antigen binding fragments according to the invention, or BiTE®'s or CAR's comprising same, which contain one or more pharmaceutically acceptable carriers or excipients.

In preferred exemplary embodiments, the invention specifically provides for in vivo usage of the subject anti-MICA antibodies or antigen binding fragments of the invention, or BiTE®'s or CARs or cells engineered to express same wherein the methods comprise administering a therapeutically effective amount of any of the foregoing in order to deplete soluble MICA, MICB and/or to deplete MICA or MICB expressing cells in a recipient in need thereof, e.g., one with cancer, an autoimmune disorder, inflammatory disease, infection, or one with transplanted cells, tissue or organs wherein depletion of MICA and/or MICB and MICA or MICB cells is therapeutically desirable.

In other exemplary embodiments, the invention specifically provides for ex vivo usage of the subject anti-MICA antibodies or antigen binding fragments of the invention, or BiTE®'s or CARs or cells engineered to express same, wherein any of the foregoing is placed into contact with cells or bodily fluids derived from a donor in order to deplete MICA or MICB and/or to deplete MICA or MICB expressing cells.

In other exemplary embodiments, the invention specifically provides for kits containing the subject anti-MICA antibodies or antigen binding fragments of the invention, or BiTE®'s, CARs, other fusions containing or immune cells which are engineered to express same, which may further comprise other actives, detectable labels or excipients and directions for the user.

The invention specifically contemplates chimeric antigen receptors (CARs) and immune cells engineered to express same, wherein such CARs include an antigen binding fragment of an antibody or fragment that specifically binds to MICA according to the invention, which CAR may further optionally include a transmembrane region, an intracellular T-cell receptor signaling domain, an FcRγ signaling domain, one or more linkers, or any combination thereof. In some embodiments, the transmembrane region and intracellular T-cell receptor signaling domain may be those of CD3 zeta. In other embodiments, the chimeric antigen receptor may include an intracellular signaling domain of a costimulatory molecule, e.g., CD28, 4-1BB or another as described infra.

The invention further specifically provides novel bi-specific T-cell engagers or BiTE®'s including an antigen binding fragment of an antibody that specifically binds to MICA, and an antigen binding domain that binds to an immune effector cell antigen; wherein in some embodiments the immune effector cell antigen is CD3.

The invention further specifically provides therapeutic methods using any of the foregoing wherein the administration thereof to subjects in need induces effector cell promoted lysis of MICA and/or MICB expressing tumor cells.

The invention further specifically provides therapeutic methods using any of the foregoing wherein the administration thereof to subjects in need ameliorates a disease or condition associated with aberrant expression of MICA and/or MICB such as cancer, autoimmune disorders, inflammatory disease, infection, or a transplanted cells, tissue or organs. The invention especially contemplates the administration of primary T cells engineered to express a CAR according to the invention, which T cells optionally may be further modified to eliminate or reduce the expression or function of the endogenous T cell receptors (TCR's) and/or to eliminate or reduce the expression or function of the endogenous HLA genes or HLA gene regulators.

The subject anti-MICA and/or MICB antibodies or antigen binding fragments, preferably human scFvs, or other human or humanized antibodies, as well as BiTE®'s, CAR's, and immune cells which express same, are useful in ameliorating, preventing, treating, or relieving at least one disease or symptom thereof which is associated with the increased expression of MICA and/or MICB on cells and/or excretion of soluble MICA and/or MICB by cells. These diseases include in particular cancer, autoimmune disorder, inflammatory disease, infection, transplant rejection.

Examples of cancers which may be treated using the subject anti-MICA antibodies or antigen binding fragments, preferably human or humanized, as well as BiTE®'s, CAR's and immune cells which express same include by way of example lymphoma, leukemia, melanoma, and/or sarcoma, such as bladder cancer; breast cancer; colon cancer; kidney cancer; liver cancer; lung cancer; ovary cancer; prostate cancer; pancreas cancer; stomach cancer; cervix cancer; thyroid cancer; skin cancer including squamous cell carcinoma; lymphoid lineage tumors including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma and Burkett's lymphoma; myeloid lineage tumors, including acute and chronic myelogenous leukemias and promyelocytic leukemia; mesenchymal tumors, including fibrosarcoma and rhabdomyosarcoma; neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; melanoma, xeroderma pigmentosum, keratoacanthoma, seminoma, thyroid follicular cancer and teratocarcinoma; T-cell and B-cell tumors, including T-prolymphocytic leukemia (T-PLL), small cell and cerebriform cell type; large granular lymphocyte leukemia (LGL) preferably of the T-cell type; Sézary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic large cell lymphoma; intestinal T-cell lymphoma; T-lymphoblastic; and lymphoma/leukemia. In a specific embodiment, the cancer is epithelial. In other specific exemplary embodiments, the cancer treated is pancreatic cancer, prostate cancer, breast cancer, melanoma, mastocytoma, leukemia, or ovarian cancer.

The antibodies or antigen binding fragment thereof of the present invention and BiTE®'s, CAR's, other fusions containing or cells engineered to express any of the foregoing also may be used to ameliorate, prevent, treat, or relieve other immune diseases wherein MICA or MICB antigens may be overexpressed or secreted including systemic lupus erythematosus, Hashimoto's thyroiditis, myasthenia gravis, Guillain-Barre syndrome, autoimmune uveitis, primary biliary cirrhosis, autoimmune hepatitis, autoimmune hemolytic anemia, pernicious anemia, autoimmune thrombocytopenia, Grave's disease, autoimmune oophoritis, autoimmune orchitis, temporal arteritis, anti-phospholipid syndrome, Wegener's granulomatosis, Behçet's disease, scleroderma, polymyositis, dermatomyositis, ankylosing spondylitis, Sjögren's syndrome, dermatitis herpetiformis, pemphigus vulgaris, vitiligo, psoriatic arthritis, osteoarthritis, steroid-resistant asthma, chronic obstructive pulmonary disease, or atherosclerosis.

The present invention specifically provides anti-MICA antigen binding fragments referred to herein as B2, C11, C25, and C8 and anti-MICA antibodies comprising the same or substantially the same CDRs as any of said antibodies or antibodies which compete or bind to the same or overlapping linear or conformational epitope(s) on MICA as any of B2, C11, C25, or C8. Particularly, the present invention specifically provides anti-MICA antibodies or antigen binding fragments comprising at least two, at least three, at least four, at least five, or at least six complementarity determining regions (CDRs) of an anti-MICA antibody selected from B2, C11, C25, or C8.

In specific embodiments of the inventions, the anti-MICA antibody or antigen binding fragment of the invention will include:

(i) an anti-MICA antibody or antibody fragment that comprises the variable heavy ($V_H$) CDR1, 2 and 3 polypeptides of SEQ ID NO:35, 36 and 22 respectively and the VL CDRs of SEQ ID NO:26, 28 and 37 respectively;

(ii) an anti-MICA antibody or antigen binding fragment that comprises the $V_H$ CDR1, 2 and 3 polypeptides of SEQ ID NO:38, 20 and 23 respectively and the variable light ($V_L$) CDR1, 2 and 3 polypeptides of SEQ ID NO:26, 29 and 39 respectively;

(iii) an anti-MICA antibody or antigen binding fragment that comprises the $V_H$ CDR1, 2 and 3 polypeptides of SEQ ID NO:40, 41 and 24 respectively and the $V_L$ CDR1, 2 and 3 polypeptides of SEQ ID 42, 30 and 33 respectively;

(iv) an anti-MICA antibody or antigen binding fragment that comprises the VH CDR1, 2 and 3 polypeptides of SEQ ID NO:43, 21 and 25 respectively and the $V_L$ CDR1, 2 and 3 polypeptides of SEQ ID NO:44, 31 and 34 respectively;

(v) an anti-MICA antibody or antigen binding fragment that comprises a $V_H$ chain polypeptide preferably at least 80, 85 or 90, 95, 96, 97, 98, 99 or 100% identical to SEQ ID NO:9 and a variable light chain polypeptide at least 90, 95, 96, 97, 98, 99 or 100% identical to SEQ ID NO:10, and comprising at least 4, 5 or 6 of the same CDRs as said antibody or antibody fragment;

(vi) an anti-MICA antibody or antigen binding fragment that comprises a $V_H$ chain polypeptide preferably at least 80, 85 or 90, 95, 96, 97, 98, 99 or 1000/identical to SEQ ID NO: 11 and a variable light chain polypeptide at least 90, 95, 96, 97, 98, 99 or 100% identical to SEQ ID NO: 12 and comprising at least 4, 5 or 6 of the same CDRs as said antibody or antibody fragment;

(vii) an anti-MICA antibody or antibody fragment that comprises a $V_H$ polypeptide preferably at least 80, 85 or 90, 95, 96, 97, 98, 99 or 100% identical to SEQ ID NO:13 and a variable light chain polypeptide at least 90, 95, 96, 97, 98, 99 or 100% identical to SEQ ID NO:15 and comprising at least 4, 5 or 6 of the same CDRs as said antibody or antibody fragment;

(viii) an anti-MICA antibody or antibody fragment that comprises a $V_H$ polypeptide preferably at least 80, 85 or 90, 95, 96, 97, 98, 99 or 100% identical to SEQ ID NO:13 and a $V_L$ polypeptide preferably at least 80, 85 or 90, 95, 96, 97, 98, 99 or 100% identical to SEQ ID NO:16 and comprising at least 4, 5 or 6 of the same CDRs as said antibody or antibody fragment; and/or (ix) an anti-MICA antibody or antigen binding fragment that comprises (1) a $V_H$ comprising (i) a CDR1 selected from any of SEQ ID NO:17 or 18, a CDR2 selected from SEQ ID NO:19, 20 or 21, and a CDR3 selected from SEQ ID NO:22, 23, 24, or 25; and (2) a $V_L$ comprising a CDR1 selected from SEQ ID NO:26 or 27, a CDR2 selected from SEQ ID NO:28, 29, 30 or 31, and a CDR3 selected from SEQ ID NO:32, 33 or 34; and (x) scFv's, Fab's, F(ab)$_2$'s, Fv, F(ab')$_2$'s, F(ab), dsFv's, scFv-Fc's, (scFv)$_2$'s, diabodies, microbodies, dual affinity retargeting reagents (DART's), sdAb's, and bivalent single chain variable fragments such as di-scFv's, bi-scFv's, bi-specific T-cell engagers ("BiTE®'s") containing any of the foregoing antibody sequences or any combination thereof, and most especially a CAR or a BiTE® or a recombinant cell comprising or expressing an anti-MICA antibody or antigen binding fragment according to any of the foregoing.

In another specific embodiment of the inventions, the antibody or antigen binding fragment of the invention as in (i)-(x) may further include a linker which attaches the anti-MICA antibody or antigen binding fragment to another moiety, e.g., another antibody antigen binding fragment, e.g., one that that specifically binds to an antigen expressed by an immune effector cell or a domain of an immune signaling or costimulatory polypeptide such as CD28, 4-1BB, and the like.

In another specific embodiment of the inventions, the antibody or antigen binding fragment of the invention as in (i)-(x) may be comprised in a fusion or conjugate, e.g., a BiTE® or CAR that comprises an antibody or antigen binding fragment that specifically binds CD3, e.g., one that comprises:

(i) a heavy chain variable region comprising,
  (i) a CDR1 of SEQ ID NO:45,
  (ii) a CDR2 of SEQ ID NO:46, and
  (iii) a CDR3 of SEQ ID NO:47; and
(ii) a light chain variable region comprising,
  (i) a CDR1 of SEQ ID NO:48,
  (ii) a CDR2 of SEQ ID NO:49, and
  (iii) a CDR3 of SEQ ID NO:50.

In another specific embodiment of the inventions, the antibody or antigen binding fragment of the invention as in (i)-(x) may be comprised in a fusion or conjugate, e.g., a BiTE® that comprises another antibody or antigen binding fragment which specifically binds to an antigen expressed by an immune effector cell such as those identified infra.

In another embodiment of the invention, the antibody or antigen binding fragment of the invention may comprise any bi-specific T-cell engager molecule, F(ab)$_2$, Fv, scFv, F(ab') 2, F(ab), VL, VH, dsFv, scFv-Fc, (scFv)$_2$, diabody, microbody, dual affinity retargeting reagents (DART), sdAb, bivalent single chain variable fragment such as di-scFv or bi-scFv, or any combination thereof containing an anti-MICA antibody according to the invention.

In one embodiment of the invention, the antibody or antigen binding fragment is an IgG, IgA, IgM, or IgE, preferably a human IgG1, IgG2, IgG3 or IgG4.

The invention specifically includes embodiments wherein the inventive binding molecule has a first binding domain decreases the binding of major histocompatibility complex class I chain-related gene A (MICA) or major histocompatibility complex class I chain-related gene B (MICB) with natural killer group 2D (NKG2D), and a second binding domain with affinity for an effector cell antigen, wherein the first binding domain comprises an antigen binding fragment that specifically binds MICA and/or MICB, preferably one of the antibodies and antigen binding fragments described herein and the second binding domain binds to an antigen expressed by an immune effector cell, e.g., a natural killer (NK) cell, a T cell, a B cell, a dendritic cell, and/or a myeloid lineage cell, preferably a myeloid lineage cell selected from a monocyte, macrophage, dendrocyte, or neutrophilic granulocyte, or a T cell selected from a cytotoxic T cell (CTL) or $CD8^+$ T cell, a helper T cell or $CD4^+$ T cell, a memory T cell, a T cell progenitor, an immature or naïve T cell, a TH1 cell, or a TH2 cell.

In one embodiment of the invention, the effector cell antigen is one or more of CD3, CD16, CD25, CD28, CD64, CD89, NKG2D, and NKp46; preferably the effector cell antigen is CD3.

Another embodiment of the invention is directed to a chimeric antigen receptor (CAR) comprising a binding domain that decreases the binding of major histocompatibility complex class I chain-related gene A (MICA) or major histocompatibility complex class I chain-related gene B (MICB) with natural killer group 2D (NKG2D); a transmembrane domain; and an intracellular cell signaling domain. In some embodiments of the invention, the binding domain is any of the binding molecules described herein.

In some of the CAR embodiments of the invention, the intracellular signaling domain can be selected from any one or more of CD3ζ, FcRγ, Syk-PTK, CD28, 41BB, CD134, ICOS, OX40, DAP10, and CD19, in any order from carboxy terminus to amino terminus. Preferably the intracellular signaling domain is selected from any one or more of CD3ζ, FcRγ, Syk-PTK, CD28, 41BB, DAP10, or CD134, in any order from carboxy terminus to amino terminus. More preferably the intracellular signaling domain comprises CD28, CD3ζ, 41BB, DAP10, and/or OX40, in any order from carboxy terminus to amino terminus.

In a preferred embodiment, the MICA binding domain of the CAR is B2.

The invention is also directed to embodiments including vectors comprising a polynucleotide sequence encoding any of the binding molecules described above and/or any of the CARs described herein.

In one embodiment of the invention, the invention is directed to a cell comprising any of the CAR molecules described herein or any of the vectors described herein. In a preferred embodiment, the cell is a T cell or other immune cell, preferably primary human immune cells.

Also contemplated herein are kits comprising any the binding molecules, vectors and/or cells described herein.

In a further embodiment of the invention, contemplated are compositions including any of the binding molecules, vectors and/or cells described infra. In a preferred embodiment, the compositions will comprise pharmaceutical compositions which may include pharmaceutically acceptable diluent, excipient, carrier, solubilizer, emulsifier, preservative, or mixture thereof.

In a particularly preferred embodiment of the invention, methods are provided directed to ameliorating, preventing, and/or decreasing the symptoms of a subject suffering from a disease associated with increased expression of major histocompatibility complex class I chain-related gene A (MICA) or major histocompatibility complex class I chain-related gene B (MICB), comprising administering to the subject an effective amount of any one or more of the binding molecules described herein, and/or any one or more of the cells described herein. In one embodiment the subject is administered one or more of the engineered immune cells described herein, preferably T cells engineered to express one or more CARs according to the invention. In a preferred embodiment, the T cells are obtained from the treated subject or other immune compatible donors. Such embodiments may further include steps such as obtaining T cells, optionally from the subject; transducing the T cells with the a vector such that the T cells express the CAR; optionally knocking out or reducing TCR or HLA expression, and injecting the transduced T cells into the subject.

In a further embodiment, the T cells may contain a polynucleotide encoding a gene that triggers cell death, i.e., suicide gene when expressed. This gene is optionally regulated by a signal that can be administered to the subject when it is desired to eliminate the T cells from the subject. The gene may preferably be selected from one or more of the following genes: HSV-TK suicide gene, hygromycin thymidine kinase (HyTK) suicide gene, an elimination gene encoding truncated CD19 which eliminates the T cells upon treatment with an appropriate mAb, a gene encoding the extracellular region of CD20, a gene encoding the extracellular region of EGFR, which like gene encoding truncated CD19 will eliminate the cells via mAb-mediated treatment, or a gene encoding a Fas-based artificial suicide gene such as *E. coli* cytosine deaminase gene or caspase-9. The cell death gene may be encoded in a vector.

In another embodiment of the invention, methods of ameliorating, preventing, and/or decreasing the symptoms of a subject suffering from a disease associated with increased expression of MICA or MICB, are contemplated in which the subject is injected with any one or more of the binding molecules described herein, preferably the injection is into the subject's blood stream.

In another contemplated embodiment of the invention, the binding molecule of the invention or cells which express same may be administered with a second therapeutic agent, wherein the moieties may be in the same or different compositions. The selection of a second therapeutic agent will depend on the disease of the subject, for instance when the disease is cancer, the method further comprises co-administration of a cytotoxic, cystostatic, or anti-angiogenic agent suitable for treating the cancer; when the disease is a B-cell lymphoma, the method further comprises co-administration of rituximab, alemtuzumab, or a CHOP chemotherapeutic regimen; when the disease is a viral infection, the method further comprises co-administration of antiviral therapies, including nucleotide and nucleoside analogues, preferably Lamivudine, Adefovir dipivoxil, Tenofevir, and/or Entecavir, and optionally immune modulatory drugs, preferably steroids, rituximab, interferon-alpha-2b and/or pegylated interferon-alpha-2a; when the disease is an inflammatory condition, the method further comprises co-administration of immunomodulatory therapies, including azathioprine, basiliximab, cyclosporine A, daclizumab, mycophenolic acid, mycophenolate mofetil, prednisone, sirolimus, and/or tacrolimus; when the disease is transplant rejection, the method further comprises co-administration of methylprednisolone, lymphocyte immune globulin, thymoglobulin, OKT3, basiliximab, rapamycin, and/or daclizimab; when the disease is diabetes, the method further comprises co-administration of an agent that promotes the growth of pancreatic beta-cells or enhances beta-cell transplantation, preferably beta cell growth or survival factors or immunomodulatory antibodies; when the disease is rheumatoid arthritis, the method further comprises co-administration of one or more of methotrexate; an anti-TNF-α antibody; a TNF receptor 1 (TNFR1)-Ig fusion protein, an anti-IL-15 antibody, a non-steroidal anti-inflammatory drug (NSAID), and a disease-modifying anti-rheumatic drug (DMARD); a biological agent, preferably an anti-TNF agent such as ENBREL®, infliximab, adalimumab, and/or rituximab; when the disease is hematopoietic transplant rejection, the method further comprises co-administration of one or more of hematopoietic growth factor(s), preferably erythropoietin, G-CSF, GM-CSF, IL-3, IL-II, thrombopoietin, or antimicrobial(s), preferably antibiotic, antiviral, and/or antifungal agents; when the disease is solid organ transplant rejection, the method further comprises co-administration of CTLA4-Ig, or abatacept; when the disease is psoriasis, the method further comprises co-administration of one or more of tar and derivatives thereof, phototherapy, corticosteroids, Cyclosporine A, vitamin D analogs, methotrexate, p38 mitogen-activated protein kinase (MAPK) inhibitors, as well as biologic agents such as anti-TNF-alpha agents and RITUXAN®; or when the disease is an inflammatory bowel disease (such as Crohn's Disease or ulcerative colitis), the method further comprises co-administration of one or more of aminosalicylates, corticosteroids, immunomodulators, antibiotics, or biologic agents such as REMICADE® and HUMIRA®.

In a further embodiment of the invention, contemplated are methods of manufacturing a chimeric antigen receptor (CAR) T cell, which can include one or more of the steps of obtaining isolated T cells; and transducing the T cells with a vector, plasmid or mRNA, such that the T cells express a CAR according to the invention.

BRIEF DESCRIPTION OF THE DRAWINGS

FIGS. 1A-1D depict the nucleotide and deduced amino acid sequences of scFv molecules B2 (FIG. 1A), C11 (FIG. 1B), C25 (FIG. 1C) and C8 (FIG. 1D). Signal sequences are in italics, heavy chain variable region sequences are underlined with a solid line, linker sequences are in bold, and light chain variable region sequences are underlined with a dashed line. Complementary determining region (CDR) sequences are in boxes. The cloned C11 nucleotide sequence had an MfeI restriction endonuclease site that was removed by replacing the T at position 525 with a C (underlined nucleotide in FIG. 1B) to facilitate cloning.

FIG. 3B, Donors X and Y). Amount of BiTE included is shown as in ng/well, from 0 to 100 ng/well. the NKG2D BiTE also recognizes MICA and is shown as a control. T cells with BiTE only and tumor cells with BiTE only are also shown as controls. B16F10-B7H6 and B16F10 are negative control cell lines for the anti-MICA BiTE.

DETAILED DESCRIPTION OF THE INVENTION

Figure 2A:
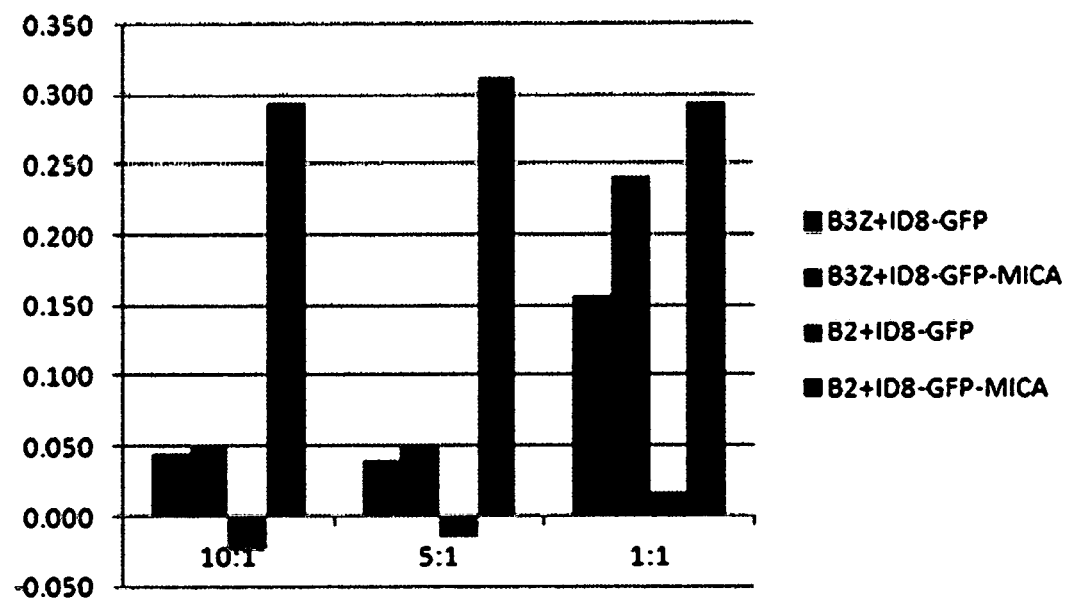
FIGS. 2A and 2B show that a T-cell reporter line expressing an anti-MICA CAR (B2) induce cell activation in the presence of tumor cells that express MICA (ID8-GFP-MICA or P815-MICA) compared to the control reporter T cell line (B3Z). Effector:target cell ratio is indicated.

Before describing the invention in detail, the following definitions are provided.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of .+−.20% or .+−.10%, more preferably .+−.5%, even more preferably .+−.1%, and still more preferably .+−.0.1% from the specified value, as such variations are appropriate to perform the disclosed methods.

"Bi-specific T-cell engagers" or "(BiTE®'s)" are a class of artificial bispecific monoclonal antibodies that are investigated for the use in therapy, e.g., as anti-cancer drugs. They direct a host's immune system, more specifically the T cells' effector responses (e.g. cytotoxic activity), against target, e.g., cancer cells. "BiTE®" is a registered trademark of Micromet AG. More specifically, BiTE®'s herein may comprise fusion proteins comprising two different single-chain variable fragments (scFvs), preferably wherein one of the scFvs binds to MICA or MICB and the other binds to an immune cell target, e.g., CD3.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are showing some response which by way of example may include these cells producing a cytokine, eliciting cytotoxicity, expressing or not expressing certain gene or genes such as activation makers such as CD69, and/or proliferating in an antigen-specific manner.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab).sub.2, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')$_2$, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a yeast as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is recognized by the immune system as being foreign. Auto-antigens comprise, but are not limited to, cellular proteins, phosphoproteins, cellular surface proteins, cellular lipids, nucleic acids, glycoproteins, including cell surface receptors.

As used herein, the term "autoimmune disease" is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type 1), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjögren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to whom it is later to be re-introduced into the individual.

As used herein, the term "allogeneic" refers to a graft derived from a different animal of the same species.

As used herein, the term "xenogeneic" refers to a graft derived from an animal of a different species.

As used herein, the term "cancer" is defined as disease characterized by uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

As used herein, the term "co-stimulatory ligand," includes a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

As used herein, the term "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class 1 molecule, BTLA and a Toll ligand receptor.

As used herein, the term "co-stimulatory signal", refers to a signal, which in combination with a primary signal, such as TCR/CD3 ligation, leads to T cell proliferation and/or upregulation or down regulation of key molecules.

As used herein, the term "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term an "effective amount" means an amount which provides a therapeutic or prophylactic benefit.

As used herein, the term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system. For example an "endogenous" TCR is one normally or naturally expressed on the surface of a primary T cell.

As used herein, the term "exogenous" refers to any material introduced from or produced outside an organism, cell, tissue or system.

As used herein, the term the term "expression" is defined as the transcription and/or translation of a particular nucleotide sequence driven by its promoter.

As used herein, the term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is a primary antibody that is often present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used, "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer into living cells.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human, e.g., by depleting MICA or MICB antigens and MICA or MICB expressing cells.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein the phrase "primary immune cells" or "primary T cells" refers to immune cells, e.g., T cells derived from donors, e.g., human donors which are allogeneic or autologous relative to a recipient which may be modified, e.g., in order to express a CAR, to delete or disrupt TCR expression or function, and the like, and which cells are useful in human therapy. These cells may be passaged during culturing and modification. Such primary immune cells and modified forms thereof may be distinguished from cell lines, e.g., immortalized T cell lines which are unsuitable for use in human therapy.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which activates or "turns on" the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-.beta., and/or reorganization of cytoskeletal structures, and the like.

A "stimulatory molecule," as the term is used herein, means a molecule on a T cell that specifically binds with a cognate stimulatory ligand present on a cell, e.g., an antigen presenting cell.

A "stimulatory ligand," as used herein, means a ligand that when present on an antigen presenting cell (e.g., an APC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter cilia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

As used herein, a "substantially purified" cell is a cell that is substantially not associated with, or which is removed from one or more other moieties with which it is normally associated, e.g., it may be free or essentially free of other cell types. By substantially free is intended that the other moieties, e.g., other cells, may still be present, albeit in lesser amounts or percentages absent purification. A substantially purified cell also refers to a cell which has been separated or substantially separated from other cell types with which it is normally associated in its naturally occurring state, i.e., the isolated cell or cells are present in relatively greater numbers or percentages in the composition relative to the cells which are removed as a consequence of the purification. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

As previously noted the present invention provides anti-MICA antibodies, fusions or conjugates containing such anti-MICA antibodies, e.g., CAR's and BiTE®'s, and immune cells, e.g., T cells, which are engineered to express such CAR's or BiTE®'s and which cells may be further modified so as to impair or eliminate TCR expression or TCR function and/or to delete or impair HLA expression and/or to provide for the inclusion of a suicide gene which is expressed under specific, generally inducible conditions. In particular the invention provides four fully human single-chain variable fragments (scFv) which bind to human MICA protein. The sequences are provided infra and in the Sequence Listing provided with this application.

These scFv proteins can be incorporated into a chimeric antigen receptor (CAR) and expressed by primary leukocytes or T cells to facilitate recognition and activation of the leukocytes or T cells against MICA+ cells, or combined with another scFv (as in a BiTE®) which binds to and activates leukocytes or T cells as a part of a bispecific or trispecific antibody-like molecule. Therefore, the scFv molecules of this invention find application in antibody, bispecific protein, trispecific protein, or chimeric antigen receptor immunotherapies and in the treatment of cancer, infection, autoimmunity and/or inflammation.

The scFv clones of the invention were isolated from a non-immune library of human antibody scFv molecules cloned and expressed on the surface of yeast (Feldhaus, et al. (2003) *Nature Biotechnol.* 21:163-170). Yeast selections and flow cytometry selection from the non-immune yeast display library using the MILTENYI MACS system in conjunction with flow cytometric sorting has been described previously (Feldhaus, et al. (2003) *Nature Biotechnol.* 21:163-170; Siegel, et al. (2004) *J. Immunol.* Methods 286:141-53; Weaver-Feldhaus, et al. (2004) *FEBS Lett.* 564:24-34). The isolated scFvs were designated B2, C11, C25 and C8. The nucleotide and deduced amino acid were determined and are depicted in FIGS. 1A-1D. The amino acid sequences of the heavy and light chain variable regions of the scFv molecules are presented in Table 1. In the Table the complementarity determining regions (CDRs), i.e., CDR1, CDR2 and CDR3, of each heavy and light regions are underlined and bolded.

TABLE 1

| scFv | Variable Region | Sequence | SEQ ID NO: |
|---|---|---|---|
| B2 | Heavy | QVQLQQSGPGLVKPSQTLSLTCAISGDSV SSNSAAWNWIRQSPSRGLEWLGRTYYRSK WYNDYAVSVKSRITINPDTSTNQFSLQLN SVTPDDTAVYYCAREGAHEWADAFDIWGQ GTMVTVSS | 9 |
| | Light | DIQLTQSPSSLSASVGDRVTITCQASQDI SNYLNWYQQKPGKAPKLLIYDASNLETGV PPRFSGSGSGTAFTFTISSLQPEDFATYY CQQQYDNLPHTFGPGTKVDIKS | 10 |
| C11 | Heavy | EVQLVESGGGLVQPGKSLKLSCEASGFTF SGYGMHWVRQAPGRGLESVAYITSSSINI KYADAVKGRFTVSRDNAKNLLFLQMNILK SEDTAMYYCARFDWDKNYWGQGTMVTVSS | 11 |
| | Light | EFDIQMTQSPSSLPASLGDRVTINCQASD ISNYLNWYQQKPGKAPKLLIYYTNKLADG VPSRFSGSGSGRDSSFTISSLESEDIGSY YCQQYYNYPWTFGPGTKLEIKR | 12 |
| C25 | Heavy | QVQLQQSGPGLVKPSQTLSLTCAISGDSV SSNRGAWNWIRQSPSRGLEWLGRTYYRSR WINDYAVSVKSRITVNPDTSKNQFSLQLN SVTPEDTAVYYCARGQQERYDPWGQGTLV TVSSGSASAPTGILGS | 13 |
| | Light | SYVLTQPPSASGTPGQRVTISCSGSSSNI GRKGVYWFQQLPGTAPKVLIYGNNQRRSG VPDRFSGSRSGTSGSLAISGLRSEDEADY YCAAWDDSLNGPVFGGGTQLTVLS | 14 |

TABLE 1-continued

| scFv | Variable Region | Sequence | SEQ ID NO: |
|---|---|---|---|
| C8 | Heavy | EVQLMESGGGVVQPGGSLRLSCAGSGFTV SSNFMSWVRQAPGKGLEWVSLIYSDGSGG NTYYADSVKGRFTVSRDNSKNTLYLQMNS LREEDTALYYCARVSRRRSGRLFDLWGRG TLVTVSS | 15 |
| | Light | QSALTQPPSASGSPGQSVTISCTGTSSDV GGSNYVSWYQQHPGKVPKLIIYEVSKRPS GVPDRFSGSKSGNTASLTVSGLQAEDEAD YYCSSYAGGKKVFGGGTKLTVLS | 16 |

A chimeric antigen receptor (CAR) was constructed containing the B2 scFv. Specifically, the B2 scFv was fused to a portion of the CD28 molecule (including the hinge, transmembrane and cytoplasmic domains) and the cytoplasmic region of CD3ζ. Using flow cytometry, it was confirmed that this CAR could recognize the MICA molecule. Furthermore, it was found that T-cells expressing the anti-MICA CAR were functional as they induced cell activation in the presence of target cells expressing MICA.

Further, an anti-MICA/anti-CD3 BiTE® (bi-specific T-cell engager) was constructed. As shown in the examples, this anti-MICA/anti-CD3 BiTE® was demonstrated to be functional, e.g., as evidenced by the fact that it was demonstrated to trigger IFN-γ secretion in T cell and tumor cell co-cultures. (see examples infra).

Particularly, the present invention provides an antigen binding fragment having specificity for MICA, wherein the antigen binding fragment has a variable heavy chain ($V_H$) comprising the amino acid sequence of SEQ ID NO:9, SEQ ID NO: 11, SEQ ID NO:13 or SEQ ID NO:15; and a variable light chain (V) comprising the amino acid sequence of SEQ ID NO:10, SEQ ID NO:12, SEQ ID NO:14 or SEQ ID NO:16. In some embodiments, the heavy chain and/or light chain variable region can be encoded by a DNA sequence such as that provided in FIGS. 1A-1D.

In other embodiments, the invention provides an antigen binding fragment that specifically binds MICA, wherein the antigen binding fragment comprises $V_H$ and $V_L$ CDR1, CDR2, and CDR3 sequences selected from the CDR sequences contained in Table 2.

TABLE 2

| Variable Region | CDR | Sequence | SEQ ID NO: |
|---|---|---|---|
| Heavy | 1 | GDSVSSN(S/R)(A/G)AWN | 17 |
| | | GFT(V/F)S(S/G)(N/Y)(F/G)M(S/H) | 18 |
| | 2 | YYRS(K/R)W(Y/I)(N/-) | 19 |
| | | TSSSIN | 20 |
| | | YSDGSGGN | 21 |
| | 3 | EGAHEWADAFDI | 22 |
| | | FDWDKNY | 23 |
| | | GQQERYDP | 24 |
| | | VSRRRSGRLFDL | 25 |
| Light | 1 | QASQDISNYLN | 26 |
| | | (T/S)G(T/S)SS(D/N)(V/I)G(G/-)(S/R)(N/K)(Y/G)V(S/Y) | 27 |
| | 2 | DASNLET | 28 |
| | | YTNKLAD | 29 |
| | | GNNQRRS | 30 |
| | | EVSKRPS | 31 |
| | 3 | QQY(D/Y)N(L/Y)P(H/W)T | 32 |
| | | AAWDDSLNGPV | 33 |
| | | SSYAGGKV | 34 |

More particularly, the invention provides an antigen binding fragment that specifically binds MICA, comprising $V_H$ and $V_L$ CDR1, CDR2, and CDR3 sequences selected from the CDR sequences listed in Table 3, e.g., the specific combinations of CDRs comprised in any of B2, C11, C25 or C8 as shown in Table 3.

TABLE 3

| scFv | Variable Region | CDR | Sequence | SEQ ID NO: |
|------|------|-----|----------|------------|
| B2 | Heavy | 1 | GDSVSSNSAAWN | 35 |
| | | 2 | YYRSKWYN | 36 |
| | | 3 | EGAHEWADSFDI | 22 |
| | Light | 1 | QASQDISNYLN | 26 |
| | | 2 | DASNLET | 28 |
| | | 3 | QQYDNLPHT | 37 |
| C11 | Heavy | 1 | GFTFSGYGMH | 38 |
| | | 2 | TSSSIN | 20 |
| | | 3 | FDWDKNY | 23 |
| | Light | 1 | QASQDISNYLN | 26 |
| | | 2 | YTNKLAD | 29 |
| | | 3 | QQYYNYPWT | 39 |
| C25 | Heavy | 1 | GDSVSSNRGAWN | 40 |
| | | 2 | YYRSRWI | 41 |
| | | 3 | GQQERYDP | 24 |
| | Light | 1 | SGSSSNIGRKGVY | 42 |
| | | 2 | GNNQRRS | 30 |
| | | 3 | AAWDDSLNGPV | 33 |
| C8 | Heavy | 1 | GFTVSSNFMS | 43 |
| | | 2 | YSDGSGGN | 21 |
| | | 3 | VSRRRSGRLFDL | 25 |
| | Light | 1 | TGTSSDVGGSNYVS | 44 |
| | | 2 | EVSKRPS | 31 |
| | | 3 | SSYAGGKKV | 34 |

In addition to a heavy chain of SEQ ID NO:9, SEQ ID NO:11, SEQ ID NO:13 or SEQ ID NO:15, the antigen binding fragment of the invention can further include a light chain derived from a Fab library using sequential naïve chain shuffling. Likewise, in addition to a light chain of SEQ ID NO:10, SEQ ID NO:12, SEQ ID NO:14 or SEQ ID NO:16, the antigen binding fragment of the invention can further include a heavy chain derived from a Fab library using sequential naïve chain shuffling.

In some embodiments, the invention provides an antigen binding fragment with avidity for MICA of about 10 µM or less, 5 µM or less, 2 µM or less, 1 µM or less, 500 nM or less, 400 nM or less, 300 nM or less, or 200 nM or less. The invention also provides an antigen binding fragment with avidity for MICA of about 100 nM or less, about 75 nM or less, about 50 nM or less, about 25 nM or less, about 10 nM or less, or about 5 nM or less. Avidity can be measured using art-known techniques, such as ELISA or BIACORE.

In one embodiment, the antigen binding fragment is a polypeptide fragment of an antibody. In one embodiment, the antibody is IgG, IgA, IgM, or IgE, of any isotype, e.g., IgG1, IgG2, IgG3, IgG4, IgA1, IgA2, etc. The antigen binding fragment can be isolated, recombinant, modified, synthetic and/or chimeric. Furthermore, the antigen binding fragment can be any antibody fragment having specificity for MICA, including, e.g., F(ab)$_2$, Fv, scFv, F(ab')$_2$, F(ab), $V_L$, $V_H$, dsFv, scFv-Fc, (scFv)$_2$, a diabody, a microbody, a BiTE® (as described infra), a DART (as described infra), any of the known single domain antibodies (sdAb) such as a nanobody, or a bivalent single chain variable fragment (i.e., a di-scFv or bi-scFv), or any combination thereof.

The antigen binding fragment of the invention can be produced by any known technique, for example, using any suitable eukaryotic or non-eukaryotic expression system. In certain embodiments, the antigen binding fragment is produced via a eukaryotic expression system, which utilizes mammalian cells (Neuberger, et al. (1984) Nature) 312:604-8; Neuberger (1985) Trends Biochem. Sci. 9:347-9; King, et al. (1993) Biochem. J. 290:723-9; Riechmann, et al. (1988) J. Mol. Boil. 203:825-8; Dorai, et al. (1994) Biotechnology (NY) 12:890-7; Jost, et al. (1994) J. Biol. Chem. 269:26267-73), insect cells (Ailor, et al. (1999) Curr. Opin. Biotechnol. 10:142-145; Bei, et al. (1995) J. Immunol. Methods 186: 245-55; Carayannopoulos, et al. (1994) Proc. Natl. Acad. Sci. USA 91:8348-52; Hasemann & Capra (1990) Proc. Natl. Acad. Sci. USA 87:3942-6; Kretzschmar, et al. (1996) J. Immunol. Methods 195:93-101; Mahiouz, et al. (1998) J. Immunol. Methods 212:149-160), plants (Hiatt, et al. (1989) Nature 342:76-78; Fischer, et al. (1999) Biotechnol. Appl. Biochem. 30:113-6), transgenic animals (Kuroiwa, et al. (2002) Nat. Biotechnol. 20:889-94; Little, et al. (2000) Immunol. Today 21:364-70; Pollock, et al. (1999) J. Immunol. Methods 231:147-157; Young, et al. (1998) Res. Immunol. 149:606-610) or lower eukaryotes such as yeast or filamentous fungi (Nyyssonen, et al. (1993) Biotechnology (NY) 11:591-5; Frenken, et al. (1994) In: Biological Membranes: Structure Biogenesis and Dynamics. Volume H82. Edited by NATO ASI Series. Springer-Verlag Berlin, Heidelberg; pg. 223-236; Frenken, et al. (1998) Res. Immunol. 149:589-599; Sotiriadis, et al. (2001) Biotechnol. Prog. 17:618-23). Further, to facilitate purification and/or detection, the antigen binding fragment can include a tag, e.g., a His$_6$ tag, FLAG tag, myc tag and the like. In particular, Saccharomyces or CHO cell expression systems can be used to produce any of the fragments disclosed herein using techniques known in the art.

Alternatively, the antigen binding fragment of the invention can be produced using a suitable non-eukaryotic expression system such as a bacterial expression system. In particular, bacterial expression systems such as E. coli can be used to produce any of the fragments disclosed herein using techniques known in the art.

Fusion molecules or conjugates including the antigen binding fragment are also embraced by this invention. Fusion proteins including the antigen binding fragment include, e.g., chimeric antigen receptors, kappa-lambda bodies, diabodies, bivalent single chain variable fragments, trivalent single chain variable fragment (e.g., a triabody or tribody) or a tetravalent single chain variable fragment (e.g., tetrabody with specificity for two to four antigens). In some embodiments, variable domains of scFv molecules (including diabodies, bivalent, trivalent and tetravalent molecules) are linked together into a single-chain construct, wherein said scFv molecule has specificity for one or more antigens in addition to MICA.

For example, the antigen binding fragment of the invention can be engineered (e.g., as a bivalent diabody or a conjugated Fab dimer or trimer) to have specificity for MICA and another tumor antigen, e.g., an antigen associated with a lymphoma, leukemia, melanoma, or sarcoma disclosed herein. Alternatively, the antigen binding fragment can be engineered to have specificity for MICA and an antigen that promotes activation or targeting of other cells, such as cytotoxic effector cells or T cells. Accordingly, the invention also includes BiTE®'s (bi-specific T-cell engagers) and DARTS (dual affinity retargeting reagents).

As is known in the art, a BiTE® generally refers to a single polypeptide chain molecule that has two antigen binding domains, one of which binds to an immune effector cell antigen (e.g., CD3) and the second of which binds to an antigen present on the surface of a target cell (WO 05/061547; Baeuerle, et al. (2008) *Drugs of the Future* 33:137-147; Bargou, et al. (2008) *Science* 321:974-977). BiTE® molecules have been constructed to various target antigens including CD19, EpCAM, Her2/neu, EGFR, CD66e (or CEA, CEACAM5), CD33, EphA2, and MCSP (or HMW-MAA) (Baeuerle, et al. (2009) *Curr. Opin. Mol. Ther.* 11:22-30). Key hallmarks of BiTE® molecules that, in their combination, distinguish them from other bispecific constructs, include a high potency of redirected lysis with $EC_{50}$ values ranging from 0.1 to 50 pmol/L (2-1,000 pg/mL) (Baeuerle, et al. (2009) supra); strict target cell-dependent activation of T cells (Brischwein, et al. (2007) *J. Immunother.* 30:798-807); and support of serial lysis by activated T cells, i.e., activity at low E:T ratios. BiTE® molecules are typically produced as recombinant, glycosylated proteins secreted by higher eukaryotic cell lines. Accordingly, in another embodiment of this invention, an anti-MICA antigen binding fragment (e.g., a scFv) is a component of a BiTE®.

In particular embodiments, the BiTE® of this invention is composed of an anti-MICA antigen binding fragment and an immune effector cell antigen binding fragment fused together by a linker. Immune effector cells include, e.g., natural killer (NK) cells, T cells including cytotoxic T cells, or B cells, but also cells of the myeloid lineage can be regarded as immune effector cells, such as monocytes or macrophages, dendritic cells and neutrophilic granulocytes. Hence, said effector cell is preferably an NK cell, a T cell, a B cell, a monocyte, a macrophage, a dendritic cell or a neutrophilic granulocyte. According to the invention, recruitment of effector cells to aberrant cells means that immune effector cells are brought in close vicinity to the aberrant target cells such that the effector cells can directly kill, or indirectly initiate the killing of the aberrant cells that they are recruited to. In order to avoid non-specific interactions it is preferred that the bispecific molecules of the invention specifically recognize antigens on immune effector cells that are at least over-expressed by these immune effector cells compared to other cells in the body. Such antigens may include, but are not limited to, CD3, CD16, CD25, CD28, CD64, CD89, NKG2D and NKp46. In some embodiments, the immune effector cell antigen is a T cell antigen. In certain embodiments, the immune effector cell antigen is CD3. Accordingly, in particular embodiments, the BiTE® of this invention is composed of an anti-MICA antigen binding fragment and an anti-CD3 antigen binding fragment fused together by a linker.

In specific embodiments, the anti-CD3 antigen binding fragment includes a heavy chain variable region having a CDR1 sequence of SGYTFTRYTMH (SEQ ID NO:45), CDR2 sequence of YINPSRGYTNYNQKFKD (SEQ ID NO:46), and CDR3 sequence of YYDDHYCL (SEQ ID NO:47); and a light chain variable region having a CDR1 sequence of SASSSVSYMN (SEQ ID NO:48), CDR2 sequence of DTSKLAS (SEQ ID NO:49) and CDR3 sequence of QQWSSNPF (SEQ ID NO:50). See Celltech U.S. Pat. No. 5,929,212, incorporated herein by reference in its entirety.

In specific embodiments the subject anti-MICA binding molecules may be comprised in a DART which refers to an immunoglobulin molecule that includes at least two polypeptide chains that associate (especially through a covalent interaction) to form at least two epitope binding sites, which may recognize the same or different epitopes. Each of the polypeptide chains of a DART includes an immunoglobulin light chain variable region and an immunoglobulin heavy chain variable region, but these regions do not interact to form an epitope binding site. Rather, the immunoglobulin heavy chain variable region of one (e.g., the first) of the DART polypeptide chains interacts with the immunoglobulin light chain variable region of a different (e.g., the second) DART polypeptide chain to form an epitope binding site. Similarly, the immunoglobulin light chain variable region of one (e.g., the first) of the DART polypeptide chains interacts with the immunoglobulin heavy chain variable region of a different (e.g., the second) DART polypeptide chain to form an epitope binding site. DARTs may be monospecific, bispecific, trispecific, etc., thus being able to simultaneously bind one, two, three or more different epitopes (which may be of the same or of different antigens). DARTs may additionally be monovalent, bivalent, trivalent, tetravalent, pentavalent, hexavalent, etc., thus being able to simultaneously bind one, two, three, four, five, six or more molecules. These two attributes of DARTs (i.e., degree of specificity and valency may be combined, for example to produce bispecific antibodies (i.e., capable of binding two epitopes) that are tetravalent (i.e., capable of binding four sets of epitopes), etc. The construction of DART molecules is disclosed in WO 2006/113665, WO 2008/157379, and WO 2010/080538. Accordingly, in another embodiment of this invention, an anti-MICA antigen binding fragment is included in a DART.

When combined with one or more antigen binding domains, the anti-MICA antigen binding fragment of the invention can be expressed as a fusion protein, wherein the variable domain order and linker length can influence folding and structure of the resulting protein. By way of illustration a tandem diabody molecule specific for antigen A and antigen B can have the structure of $V_H^A$-linker$_1$-$V_L^B$-linker$_2$-$V_H^B$-linker$_3$-$V_L^A$. By comparison, a BiTE® can have the structure of $V_L^A$-linker$_1$-$V_H^A$-linker$_2$-$V_H^B$-linker$_3$-$V_L^B$.

Linkers of use in this invention can be between 5 and 30 amino acid residues in length and can be selected from any suitable linker known in the art. See, e.g., LeGall, et al. (2004) *Prot. Eng. Design Select.* 17:357-366. Exemplary linkers include, but are not limited to, GGGGSGGGGSGGGGS (i.e., $(G_4S)_3$)(SEQ ID NO:51), SAKTTPKLGG (SEQ ID NO:52), RADAAPTVS (SEQ ID NO:53), RADAAAAGGPGS (SEQ ID NO:54), and RADAAAA$(G_4S)_4$ (SEQ ID NO:55).

As indicated, in a preferred embodiment an anti-MICA antigen binding fragment according to the invention may be included in a chimeric antigen receptor (CAR). CARs, also known as artificial T cell receptors, chimeric T cell receptors, or chimeric immunoreceptors, are engineered receptors, which graft an arbitrary specificity onto an immune effector cell. Typically, these receptors are used to graft the specificity of a monoclonal antibody onto a T cell, e.g., via retroviral vector expression. The most common form of these molecules are fusions of scFv derived from monoclonal antibodies, fused to CD3-zeta (CD3ζ) transmembrane and endodomain, i.e., an intracellular T-cell receptor (TCR) signaling domain. Such molecules result in the transmission of a ζ signal in response to recognition by the scFv of its target. "First-generation" CARs typically have the intracellular domain from the CD3ζ-chain, which is the primary transmitter of signals from endogenous TCRs.

"Second-generation" CARs add intracellular signaling domains from various costimulatory molecules (e.g., CD28, 41BB, ICOS, OX40, Dap10, CD19) to the cytoplasmic tail of the CAR to provide additional signals to the T cell. Preclinical studies have indicated that the second generation of CAR designs improves the antitumor activity of T cells (Maher, et al. (2002) *Nat. Biotechnol.* 20:70-75; Kowolik, et al. (2006) *Cancer Res.* 66:10995-11004). More recent, "third-generation" CARs combine multiple signaling domains, such as CD3z-CD28-41BB or CD3z-CD28-OX40, to further augment potency (Zhao, et al. (2009) *J. Immunol.* 183:5563-5574; Pule, et al. (2005) *Mol. Ther.* 12:933-941; Zhong, et al. (2010) *Mol. Ther.* 18:413-420). Accordingly, in one embodiment of this invention, an anti-MICA scFv fragment is included in a CAR.

CARs of this invention can be prepared using standard recombinant protein techniques using sequences of CD3-zeta and other costimulatory molecules known in the art. For example, the human CD3-zeta sequence is available under GENBANK accession number NP_932170, the human CD28 sequence is available under GENBANK accession number NP_006130, the human OX40 sequence is available under GENBANK accession number NP_003318, and the human CD19 sequence is available under GENBANK accession number AAA69966. In particular embodiments, the CAR of this invention includes a human CD3ζ cytoplasmic domain (amino acids 52-164; RVKFSRSADA PAYQQGQNQL YNELNLGRRE EYDVLDKRRG RDPEMGGKPQ RRKNPQEGLY NELQKDKMAE AYSEIGMKGE RRRGKGHDGL YQGLSTATKD TYDALHMQAL PPR; SEQ ID NO:56), human CD28 hinge-transmembrane-cytoplasmic domains (amino acids 135-220; VKGKHLCPSP LFPGPSKPFW VLVVVGGVLA CYSLLVTVAF IIFWVRSKRS RLLHSDYMNM TPRRPGPTRK HYQPYAPPRD FAAYRS; SEQ ID NO:57), and optionally a portion of CD19 (amino acids 1-327; MPPPRLLFFL LFLTPMEVRP EEPLVVKVEE GDNAVLQCLK GTSDGPTQQL TWSRESPLKP FLKLSLGLPG LGIHMRPLAS WLFIFNVSQQ MGGFYLCQPG PPSEKAWQPG WTVNVEGSGE LFRWNVSDLG GLGCGLKNRS SEGPSSPSGK LMSPKLYVWA KDRPEIWEGE PPCVPPRDSL NQSLSQDLTM APGSTLWLSC GVPPDSVSRG PLSWTHVHPK GPKSLLSLEL KDDRPARDMW VMETGLLLPR ATAQDAGKYY CHRGNLTMSF HLEITARPVL WHWLLRTGGW KVSAVTLAYL IFCLCSLVGI LHLQRALVLR RKRKRMT; SEQ ID NO:58).

In some embodiments, a fusion molecule of the invention includes the anti-MICA antigen binding fragment conjugated to a synthetic molecule, e.g., using any type of suitable conjugation. Recombinant engineering and incorporated selenocysteine (e.g., as described in WO 2008/122039) can be used to conjugate a synthetic molecule. Other methods of conjugation can include covalent coupling to native or engineered lysine side-chain amines or cysteine side-chain thiols. See, e.g., Wu, et al. (2005) *Nat. Biotechnol.* 23:1137-1146. The synthetic molecule can be any molecule such as one targeting a tumor. Examples of synthetic molecules include therapeutic agents such as cytotoxic, cytostatic, or anti-angiogenic agents and radioisotopes. A cytotoxic agent can be a plant, fungal, or bacterial molecule (e.g., a protein toxin). A therapeutic agent can be a maytansinoid (e.g., maytansinol or DM1 maytansinoid), a taxane, or a calicheamicin. Therapeutic agents include vincristine and prednisone. A therapeutic agent can be an antimetabolite (e.g., an antifolate such as methotrexate, a fluoropyrimidine such as 5-fluorouracil, cytosine arabinoside, or an analogue of purine or adenosine); an intercalating agent (for example, an anthracycline such as doxorubicin, daunomycin, epirubicin, idarubicin, mitomycin-C, dactinomycin, or mithramycin); a platinum derivative (e.g., cisplatin or carboplatin); an alkylating agent (e.g., nitrogen mustard, melphalan, chlorambucil, busulphan, cyclophosphamide, ifosfamide nitrosoureas or thiotepa); an antimitotic agent (e.g., a vinca alkaloid like vincristine or taxoid such as paclitaxel or docetaxel); a topoisomerase inhibitor (for example, etoposide and teniposide, amsacrine, topotecan); a cell cycle inhibitor (for example, a flavopyridol); or a microbtubule agent (e.g., an epothilone, discodermolide analog, or eleutherobin analog). A therapeutic agent can be a proteosome inhibitor or a topoisomerase inhibitor such as bortezomib, amsacrine, etoposide, etoposide phosphate, teniposide, or doxorubicin. Therapeutic radioisotopes include yttrium ($^{90}$Y), lutetium ($^{177}$Lu), actinium ($^{225}$Ac), praseodymium, astatine ($^{211}$At) rhenium ($^{186}$Re), bismuth ($^{212}$Bi or $^{213}$Bi), and rhodium ($^{188}$Rh). Antiangiogenic agents include linomide, bevacuzimab, angiostatin, and razoxane. The synthetic molecule can be another antibody such as rituximab or bevacuzimab.

A synthetic molecule can also be a label. Labels can be useful in diagnostic applications and can include, for example, contrast agents. A contrast agent can be a radioisotope label such as iodine ($^{131}$I or $^{125}$I) indium ($^{111}$In), technetium ($^{99}$Tc), phosphorus ($^{32}$P), carbon ($^{14}$C), tritium ($^{3}$H), other radioisotope (e.g., a radioactive ion) or a therapeutic radioisotope listed above. Additionally, contrast agents can include radiopaque materials, magnetic resonance imaging (MRI) agents, ultrasound imaging agents, and any other contrast agents suitable for detection by a device that images an animal body. A synthetic molecule can also be a fluorescent label, a biologically active enzyme label, a luminescent label, or a chromophore label.

Moreover, a synthetic molecule can also be a magnetic nanoparticle, a controlled release polymer nanoparticle or lipid composition. Magnetic nanoparticles include, but are not limited to iron (e.g., $Fe_3O_4$ or $Fe_2O_4$), cobalt, zinc, cadmium, nickel, gadolinium, chromium, copper, manganese, terbium, europium, gold, silver, platinum, or alloys thereof. Controlled release polymer nanoparticles can be produced using conventional methods from biodegradable or nonbiodegradable polymers, e.g., poly(lactic acid), derivatives of poly(lactic acid), PEGylated poly(lactic acid), poly(lactic-co-glycolic acid), derivatives of poly(lactic-co-glycolic acid), PEGylated poly(lactic-co-glycolic acid), a polyanhydride, poly(ortho esters), derivatives of poly(ortho esters), PEGylated poly(ortho esters), poly(caprolactone), derivatives of poly(caprolactone), PEGylated poly(caprolactone), poly(acrylic acid), derivatives of poly(acrylic acid), poly(urethane), derivatives of poly(urethane), or combinations thereof). Similarly, lipid composition (e.g., liposomes, solid lipid nanoparticles and the like) can be produced using conventional methods and conjugated to an antibody of this invention.

The invention further provides eukaryotic or non-eukaryotic cells that have been recombinantly engineered to produce an antigen binding fragment or fusion molecule (e.g., a fusion protein) of the invention. The eukaryotic or non-eukaryotic cells can be used as an expression system to produce the antigen binding fragment of the invention. In another embodiment, the invention provides MICA targeted immune cells that are engineered to recombinantly express a MICA-specific antigen binding fragment or fusion molecule of the invention. For example, the invention provides a T-cell engineered to express an antigen binding fragment of the invention (e.g., an scFv, scFv-Fc, (scFv)$_2$), which is linked to a synthetic molecule with the following domains: a spacer or hinge region (e.g., a CD28 or IgG hinge), a transmembrane region (e.g., a transmembrane canonical domain), and an intracellular T-cell receptor (TCR) signaling domain, thereby forming a CAR. Intracellular TCR signaling domains that can be included in a CAR include, but are not limited to, CD3zeta, FcR-gamma and Syk-PTK signaling domains as well as the CD28, 4-1BB, and CD134 co-signaling domains. Methods for constructing T-cells expressing a CAR are known in the art. See, e.g., Marcu-Malina, et al. (2009) *Exp. Opin. Biol. Ther.* 9:579-91. Similarly, a T-cell engineered to express an antigen binding fragment of the invention as a component of a BiTE® is also particularly embraced by this invention.

The invention further provides a method for inducing effector cell lysis (e.g., NK cells and/or T cells) of MICA expressing tumor cells that in some embodiments involves blocking the interaction of MICA with NKG2D, by administering an antigen binding fragment or fusion protein (e.g., CAR or BiTE®) of the invention. The antigen binding fragment can be a naked (unconjugated) antigen binding fragment or an antigen binding fragment conjugated to a synthetic molecule, e.g., a cytotoxic, cytostatic, or anti-angiogenic agent or a radioisotope. The method can be used to lyse MICA-expressing cells in vitro or in a subject (i.e., in vivo). The MICA-expressing cells can be in, for example, a cell culture or animal model of a disorder associated with aberrant expression or amounts of MICA. Cytotoxicity of an antigen binding fragment or fusion molecule (e.g., CAR or BiTE®) of the invention can be assessed using any conventional assay including, e.g., a lactate dehydrogenase cytotoxicity assay such as the CYTOTOX 96 non-radioactive cytotoxicity assay commercially available from PROMEGA or by assaying for the induction of certain cytokines such as γ-interferon.

The invention also provides a method of treating a subject that has, is suspected to have, or is at risk for a disease or disorder associated with increased amounts of MICA. As used in the context of the present invention, the term "increased" is intended to mean that MICA expression is elevated as compared to expression of MICA in normal or healthy cells. Generally, the method of treatment includes administering a therapeutically effective amount of an antibody fragment or fusion protein of the invention to the subject. A therapeutically effective amount may be, for example, an amount sufficient to cause an increase in the depletion of MICA⁺ cells in vivo, and/or an increase in the frequency of activated, reactive and/or cytotoxic NKG2D⁺ effector cells (e.g., NK cells) toward MICA-expressing cells.

The antigen binding fragment can be any anti-MICA antigen binding fragment described herein, including chimeric, synthetic, F(ab)$_2$, scFv, F(ab'$_2$, F(ab), VL, VH, dsFv, Fv, or (scFv)$_2$. In some embodiments, the method includes administering an scFv, a dsFv, a F(ab')$_2$, a diabody, a bivalent antibody, a CAR, a BiTE® or a DART. In other embodiments, the administered antigen binding fragment can be conjugated to a synthetic molecule described above, e.g., a cytotoxic, cytostatic, or anti-angiogenic agent or a therapeutic radioisotope. An exemplary cytotoxic agent is *Pseudomonas* exotoxin A (PE38).

Diseases or disorders that can be treated include, for example, cancers such as lymphomas, leukemia, melanomas, and sarcomas. More specifically, the method of the invention can be used in the treatment of carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias and promyelocytic leukemia; other tumors, including neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xeroderma pigmentosum, keratoacanthoma, seminoma, thyroid follicular cancer and teratocarcinoma. Other exemplary disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sézary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic large cell lymphoma; intestinal T-cell lymphoma; T-lymphoblastic; and lymphoma/leukemia.

In addition, the method of the invention can be used in the treatment of infections including, but not limited to bacterial, fungal and/or viral infections. Viruses contemplated as treatable using methods of the present invention include cytomegaloviras, herpesvirus, human immunodeficiency virus, Epstein-Barr virus, respiratory syncytial virus, hepatitis virus, influenza virus and any others. This method may be of particular use with patients who are partially immunocompromised as a result of therapeutic treatment (radiation, chemotherapy, cytostatic) or disease (AIDS), by providing mobilization of compromised T-cell function.

The present invention further provides methods for preventing and/or treating inflammatory diseases, including various inflammatory autoimmune disorders and syndromes associated with MICA expression and NKG2D activation. Such syndromes, include, but are not limited to, clinical situations in which induction of stress-related NKG2D ligands such as MICA, results in excessive activation and/or expansion of autoreactive T cells and/or NK cells, which may be reflected in increased levels of cytokines such as IL-2, TNF-α, and IL-15.

One example of an autoimmune disorder that can be treated in accordance with the method of the invention is rheumatoid arthritis (RA). Upon administration of an antigen binding fragment or fusion protein, the method results in a modulation of one or more biomarkers in a manner consistent with the treatment or prevention (as applicable) of RA (e.g., serum IL-6, TNF R, IL-2R, shed CD4, shed CD8, and/or C reactive protein). In another embodiment, the practice of the method results in a detectable reduction of synovial inflammation in the peripheral joints of the patient/host.

In yet another embodiment, the invention provides methods of reducing the likelihood of transplant rejection (or reducing the severity or time to onset of a transplant rejection-related condition). The method involves delivering (e.g., administering directly or administering by way of a composition or T-cell) an effective amount of an antigen binding fragment or fusion protein of the invention to a human patient or mammalian host that is about to be, is, or recently was the recipient of a tissue/organ transplant, such that the likelihood of rejection is detectably reduced (e.g., as compared to a control).

For example, the present invention provides methods for treating or preventing solid organ allograft rejection, the methods comprising administering a MICA binding agent according to the invention to a subject in need thereof, under conditions suitable for treating or preventing solid organ allograft rejection. In some embodiments, the graft is selected from the group consisting of a cardiac allograft, a lung allograft, a cardiac/lung allograft, a kidney allograft, a pancreas allograft, a kidney/pancreas allograft, a liver allograft, an intestine allograft and a skin allograft. In some embodiments, the administering is done prior to and after transplantation of the allograft. In some embodiments, the therapy may further comprise use of an immunomodulatory agent including but not limited to CTLA4-Ig, cyclosporin A, tacrolimus, sirolimus, everolimus, basiliximab, daclizumab, mycophenolate mofetil, mycophenolate sodium, azathioprine and FTY-720. In some embodiments, the adjunct therapy comprises one or more of an antibiotic, an anti-viral agent, an anti-fungal medication, an anti-ulcer medication and a diuretic.

In other embodiments the subject therapeutic methods result in preventing radiographic deterioration and improving physical function in the patient or host as exhibited by, e.g., a reduction in radiographic progression in the patient or host, reduction in swollen and tender joints (as determined by acceptable analytical criteria), and/or significantly improved quality of life (e.g., as determined by a reduction in disability scores on the RA Health Assessment Questionnaire). Other examples of autoimmune diseases or disorders that can be treated with an antigen binding fragment or fusion protein of the invention include multiple sclerosis, inflammatory bowel disease such as Crohn's disease or ulcerative colitis, psoriasis, type I diabetes mellitus.

The inventive methods and MICA binding agents disclosed and claimed herein can similarly be applied to a variety of other autoimmune diseases and inflammatory conditions associated with NKG2D and MICA, including systemic lupus erythematosus, Hashimoto's thyroiditis, myasthenia gravis, Guillain-Barre syndrome, autoimmune uveitis, primary biliary cirrhosis, autoimmune hepatitis, autoimmune hemolytic anemia, pernicious anemia, autoimmune thrombocytopenia, Grave's disease, autoimmune oophoritis, autoimmune orchitis, temporal arteritis, anti-phospholipid syndrome, Wegener's granulomatosis, Behçet's disease, scleroderma, polymyositis, dermatomyositis, ankylosing spondylitis, Sjögren's syndrome, dermatitis herpetiformis, pemphigus vulgaris, vitiligo, psoriatic arthritis, osteoarthritis, steroid-resistant asthma, chronic obstructive pulmonary disease, and atherosclerosis. In some embodiments, the transplant is a bone marrow (BM) or peripheral blood stem cell (PBSC) transplant. In some embodiments, the BMT transplant or PBSC transplant is administered as treatment of leukemia or lymphoma, while in other embodiments, the transplant is administered as treatment for other types of cancers such as neuroblastoma or multiple myeloma.

The invention also provides a method of treating a subject that has, is suspected to have, or is at risk for a disorder associated with elevated levels of MICA by adoptive transfer of the recombinant host cells, e.g., T-cells described herein, which express an antigen binding fragment of the invention, e.g., as a CAR or BiTE® that selectively binds MICA. Recombinant technology can be used to introduce CAR- or BiTE®-encoding genetic material into any suitable T-cells including effector memory T-cells (e.g., an autologous or third party-derived T-cell). The T-cells carrying the genetic material can be expanded (e.g., in the presence of cytokines). The recombinant T-cells are transferred, typically by infusion, to the patient. The transferred T-cells of the invention can bind MICA and reestablish an immune response against, e.g., cancer cells in the subject. The adoptive transfer method can be used, for example, to treat subjects that have or are suspected to have a cancer, infection, inflammatory condition or autoimmune disorder as described herein.

In embodiments pertaining to the use of recombinant T-cells, said cells optionally may be modified to impair or eliminate TCR expression or function and/or HLA expression or function. Also, these T cells or other immune cells which are engineered to express a MICA binding agent, e.g., a CAR according to the invention may also include a nucleic acid encoding a protein that is capable of triggering cell death or elimination. Examples of such proteins include suicide proteins such as thymidine kinase (TK) of the HISV virus (herpesvirus) type I (Bonini, et al. (1997) *Science* 276:1719-1724), a Fas-based "artificial suicide gene" (Thomis, et al. (2001) *Blood* 97:1249-1257), *E. coli* cytosine deaminase gene or caspase-9, which are activated by ganciclovir, AP1903, 5-fluorocytosine or a specific chemical inducer of dimerization (CID), respectively.

The nucleic acid encoding the protein for cell death or elimination allows for ablating the transduced T cells in case of toxicity and to destroy the cell containing or producing the CAR or BiTE® once a tumor has been reduced or eliminated. The use of suicide genes for eliminating transformed or transduced cells is described in the art. For example, Bonini, et al. ((1997) *Science* 276:1719-1724) teach that donor lymphocytes transduced with the HSV-TK suicide gene provide antitumor activity in patients for up to one year and elimination of the transduced cells is achieved using ganciclovir. Further, Gonzalez, et al. ((2004) *J. Gene Med.* 6:704-711) describe the targeting of neuroblastoma with cytotoxic T lymphocyte clones genetically modified to express a chimeric scFvFc:ζ immunoreceptor specific for an epitope on L1-CAM, wherein the construct further expresses the hygromycin thymidine kinase (HyTK) suicide gene to eliminate the transgenic clones.

Examples of other proteins of use in cell elimination include, e.g., truncated CD19 (Tey, et al. (2007) *Biol. Blood Marrow Transplant* 13:913-24), the extracellular region of CD20 (Introna, et al. (2000) *Hum. Gene Ther.* 11:611-20; Griffioen, et al. (2009) *Haematologica* 94:1316-20), and the extracellular region of EGFR (Terakura, et al. (2012) *Blood* 119:72-82). See also, Lang, et al. (2004) *Blood* 103:3982-5. Incorporation of these proteins into gene-modified T cells renders the cells susceptible to elimination by clinically used anti-CD19 antibodies, anti-CD20 antibodies, and anti-EGFR antibodies (e.g., cetuximab).

It is contemplated that the nucleic acid encoding the protein for cell death or elimination can be expressed from the same promoter as the CAR or the same promoter in a cell which expresses the BiTE® or may be expressed from a different promoter. Generally, however, nucleic acid encoding the protein for cell death or elimination, CAR or BiTE® reside on the same construct or vector. Expression of the protein for cell death or elimination from the same promoter as the CAR or BiTE® can be accomplished using, e.g., an internal ribosomal entry site (IRES) or cis-acting hydrolase element.

An "internal ribosome entry site" or "IRES" is a sequence motif that promotes attachment of ribosomes to that motif on internal mRNA sequences. Consequently, an mRNA containing an IRES sequence motif results in two translational products, one initiating from the 5'-end of the mRNA and the other by an internal translation mechanism mediated by the IRES. A number of IRES have been described and can be used in the nucleic acid construct of this invention. See, e.g., U.S. Pat. No. 8,192,984; WO 2010/119257; and US 2005/0112095.

A "cis-acting hydrolase element" or "CHYSEL" refers to a peptide sequence that causes a ribosome to release the growing polypeptide chain that it is being synthesizes without dissociation from the mRNA. In this respect, the ribosome continues translating and therefore produces a second polypeptide. Peptides such as the foot and mouth disease virus (FMDV) 2A sequence (GSGSRVTELLYRMKRAE-TYC PRPLLAIHPTEARHKQKIVAPVKQLL-NFDLLKLAGDVESNPGP, SEQ ID NO:59), sea urchin (*Strongylocentrotus purpuratus*) 2A sequence (DGFCI-LYLLLILLMRSGDVETNPGP, SEQ ID NO:60); Sponge (*Amphimedon queenslandica*) 2A sequence (LLCF-MLLLLLSGDVELNPGP, SEQ ID NO:61; or HHFM-FLLLLL AGDIELNPGP, SEQ ID NO:62); acorn worm (*Saccoglossus kowalevskii*) (WFLVLLSFILSGDIEVNPGP, SEQ ID NO:63) 2A sequence; amphioxus (*Branchiostoma floridae*) (KNCAMYMLLLSGDVETNPGP, SEQ ID NO:64; or MVISQLMLKLAGDVEENPGP, SEQ ID NO:65) 2A sequence porcine teschovirus-1 (GSOATNF-SLLKQAGDVEENPGP, SEQ ID NO:66) 2A sequence; Thoseaasigna virus (GSGEGRGSLLTCGDVEENPGP, SEQ ID NO:67) 2A sequence; and equine rhinitis A virus (GSGQCTNYALLKLAGDVESNPGP, SEQ ID NO:68) 2A sequence are CHYSELs of use in this invention. In some embodiments, the 2A sequence is a naturally occurring or synthetic sequence that includes the 2A consensus sequence D-X-E-X-NPGP (SEQ ID NO:69), in which X is any amino acid residue.

In embodiments where it is sought to inhibit the activity or growth of, or deplete, a patient's MICA-positive cells, the ability of the anti-MICA antigen binding fragment or fusion molecule thereof to inhibit proliferation of or deplete a patient's MICA-positive cells is assessed. If the MICA-positive cells are depleted by the anti-MICA antigen binding fragment or fusion molecule thereof, the patient is determined to be responsive to therapy with an anti-MICA an antigen binding fragment or fusion molecule thereof.

In addition to an antigen binding fragment or fusion protein, the foregoing methods of treatment can further include co-administering a second therapeutic agent for treating the disorder. For example, when the disorder to be treated involves a MICA-expressing cancer, the method can further include co-administration of a cytotoxic, cystostatic, or anti-angiogenic agent suitable for treating the cancer. If the cancer is a B-cell lymphoma, the method can further include, for example, co-administration of rituximab, alemtuzumab, or a CHOP chemotherapeutic regimen. When the disorder is a viral infection, the method can further include co-administration of antiviral therapies, including but not limited to nucleotide and nucleoside analogues (Lamivudine, Adefovir dipivoxil, Tenofevir, and Entecavir) and other immune modulatory drugs (steroids, rituximab, interferon-alpha-2b and pegylated interferon-alpha-2a). When the disorder is an inflammatory condition, the method can further include co-administration of immunomodulatory therapies, including but not limited to azathioprine, basiliximab, cyclosporine A, daclizumab, mycophenolic acid, mycophenolate mofetil, prednisone, sirolimus, and tacrolimus. In some embodiments, the antigen binding fragment or fusion protein is administered to a subject as part of an induction immunosuppression regimen. This approach includes all medications given immediately after transplantation in intensified doses for the purpose of preventing acute rejection. Although the drugs may be continued after discharge for the first 30 days after transplant, they are not used long-term for immunosuppressive maintenance. Associated medications can include methylprednisolone, lymphocyte immune globulin, thymoglobulin, OKT3, basiliximab or daclixumab. Rapamycin has also been used for induction immunosuppression.

When the disease being treated is Type 1 diabetes, the second therapeutic agent can include an agent that promotes the growth of pancreatic beta-cells or enhances beta-cell transplantation, such as, e.g., beta cell growth or survival factors or immunomodulatory antibodies. When the disease is rheumatoid arthritis, the additional agent is one or more of methotrexate; an anti-TNF-α antibody; a TNF receptor 1 (TNFR1)-Ig fusion protein, an anti-IL-15 antibody, a non-steroidal anti-inflammatory drug (NSAID), and a disease-modifying anti-rheumatic drug (DMARD). For example, the additional agent may be a biological agent such as an anti-TNF agent (e.g., ENBREL®), infliximab (REMICADE®) and adalimumab (HJUMIRA®) or rituximab (RITUXAN®). In some embodiments, in which the disease is hematopoietic transplant rejection, hematopoietic growth factor(s) (e.g., erythropoietin, G-CSF, GM-CSF, IL-3, IL-II, thrombopoietin, etc.) or antimicrobial(s) (e.g., antibiotic, antiviral, antifungal) may be administered as an adjunct therapy. In other embodiments, where the disease or disorder is solid organ transplant (e.g., a heart transplant) rejection, the additional agent may be, e.g., CTLA4-Ig (abatacept; ORENCIA®). In embodiments where the disorder is psoriasis, the additional agent is one or more of tar and derivatives thereof, phototherapy, corticosteroids, Cyclosporine A, vitamin D analogs, methotrexate, p38 mitogen-activated protein kinase (MAPK) inhibitors, as well as biologic agents such as anti-TNF-alpha agents and RITUXAN®. In embodiments where the disease or disorder is an inflammatory bowel disease such as, for example, Crohn's Disease or ulcerative colitis, the additional agent is one or more of aminosalicylates, corticosteroids, immunomodulators, antibiotics, or biologic agents such as REMICADE® and HUMIRA®.

Treatments according to the present invention do not necessarily imply 100% or complete treatment. Rather, there are varying degrees of treatment of which one of ordinary skill in the art recognizes as having a potential benefit or therapeutic effect. In this respect, the inventive method can provide any amount of any level of treatment. Furthermore, the treatment provided by the inventive method can include the treatment of one or more conditions or symptoms of the disease being treated.

For use in treatment, the invention also provides a pharmaceutical composition containing an antigen binding fragment or fusion molecule thereof, as well as recombinant T-cells containing the same, and a pharmaceutically acceptable carrier. Pharmaceutical compositions can be prepared from any of the antigen binding fragments, fusion molecules or T-cells described herein. An exemplary composition includes a recombinant T-cell harboring nucleic acids encoding anti-MICA scFv fused to anti-CD3e scFv via a flexible linker (i.e., a BiTE®). Yet another exemplary pharmaceutical composition includes anti-MICA scFv fused to the hinge, transmembrane and intracellular domains of CD28 and the intracellular domain of CD3zeta (i.e., a CAR).

The composition of the invention includes a carrier, desirably a pharmaceutically acceptable carrier. The pharmaceutically acceptable carrier can be any suitable pharmaceutically acceptable carrier. The term "pharmaceutically acceptable carrier," as used herein, means one or more compatible solid or liquid fillers, diluents, other excipients, or encapsulating substances, which are suitable for administration into a human or veterinary patient (e.g., a physiologically acceptable carrier or a pharmacologically acceptable carrier). The term "carrier" denotes an organic or inorganic ingredient, natural or synthetic, with which the active ingredient is combined to facilitate the application. The pharmaceutically acceptable carrier can be co-mingled with one or more of the active components and with each other, when more than one pharmaceutically acceptable carrier is present in the composition in a manner so as not to substantially impair the desired pharmaceutical efficacy. "Pharmaceutically acceptable" materials typically are capable of administration to a patient without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

The pharmaceutical composition can contain suitable buffering agents, including, for example, acetic acid in a salt, citric acid in a salt, boric acid in a salt, and phosphoric acid in a salt. The pharmaceutical compositions also optionally can contain suitable preservatives, such as benzalkonium chloride, chlorobutanol, parabens, and thimerosal.

The pharmaceutical composition can be presented in unit dosage form and can be prepared by any suitable method, many of which are well-known in the pharmaceutical arts. Such methods include the step of bringing the antibody of the invention into association with a carrier that constitutes one or more accessory ingredients. In general, the composition is prepared by uniformly and intimately bringing the active agent into association with a liquid carrier, a finely divided solid carrier, or both, and then, if necessary, shaping the product.

A composition suitable for parenteral administration conveniently includes a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland, fixed oil can be employed, such as synthetic mono- or di-glycerides. In addition, fatty acids such as oleic acid can be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

The delivery systems useful in the context of the invention include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain compositions of the invention.

Many types of release delivery systems are available and known to those of ordinary skill in the art. Suitable release delivery systems include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: erosional systems in which the active composition is contained in a form within a matrix such as those described in U.S. Pat. Nos. 4,452,775, 4,667,014, 4,748,034, and 5,239,660; and diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

Although systemic (intravenous, IV) injection is favored in clinical applications because of its ease of administration, several preclinical studies (Carpenito, et al. (2009) *Proc. Natl. Acad. Sci. USA* 106:3360-3365; Song, et al. (2011) *Cancer Res.* 71:4617-4627; Parente-Pereira, et al. (2011) *J. Clin. Immunol.* 31:710-718) suggest that the regional (intratumoral, IT or intraperitoneal, IP) administration of T-cells may provide optimal therapeutic effects, which may be in part due to increased T-cell trafficking to the tumor. For example, it has been shown that CAR T-cells remain at the site of inoculation with minimal systemic absorption when delivered via IP or IT routes (Parente-Pereira, et al. (2011) *J. Clin. Immunol.* 31:710-718). In contrast, after IV administration, CAR T-cells initially reach the lungs and then are redistributed to the spleen, liver, and lymph nodes. In addition, RNA CAR-electroporated T-cells may be particularly suitable for regional administration, due to the transient nature of the CAR expression on the T-cells (Zhao, et al. (2010) *Cancer Res.* 70:9053-9061). Furthermore, clinical studies have shown the feasibility and safety of both the intratumoral and intraperitoneal injection of T-cells (Canevari, et al. (1995) *J. Natl. Cancer Inst.* 87:1463-1469; Duval, et al. (2006) *Clin. Cancer Res.* 12:1229-123680). Overall, a local route of administration of recombinant T-cells may provide the optimal therapeutic effect and decrease the potential for the "on-target, off-organ" toxicity The amount of recombinant (CAR) T-cells, or antigen binding fragments described herein, administered should take into account the route of administration and should be such that a sufficient number of the recombinant T-cells or antigen binding fragments will be introduced so as to achieve the desired therapeutic response. Furthermore, the amounts of each active agent included in the compositions described herein (e.g., the amount per each cell to be contacted or the amount per certain body weight) can vary in different applications. In general, the concentration of recombinant T-cells desirably should be sufficient to provide in the subject being treated at least from about $1 \times 10^6$ to about $1 \times 10^9$ recombinant T-cells, even more desirably, from about $1 \times 10^7$ to about $5 \times 10^8$ recombinant T-cells, although any suitable amount can be utilized either above, e.g., greater than $5 \times 10^8$ cells, or below, e.g., less than $1 \times 10^7$ cells. The dosing schedule can be based on well-established cell-based therapies (see, e.g., Topalian & Rosenberg (1987) *Acta Haematol.* 78 Suppl 1:75-6; U.S. Pat. No. 4,690,915) or an alternate continuous infusion strategy can be employed.

The subject CAR-T cell may be used in treating or diagnosing human or animal subjects. Animal subjects include, but are not limited to, animal models, such as, mammalian models of conditions or disorders associated with elevated or excessive MICA expression such as the cancers, autoimmune diseases, inflammatory conditions and infections described herein.

In another embodiment, the invention provides use of the antigen binding fragment of the invention to detect in a test sample an altered amount of MICA (e.g., cell surface MICA or soluble MICA), for example, relative to a control. A test sample can be from a cell culture or from a test subject, e.g., a plasma or a tissue sample from a subject that has, is suspected to have, or is at risk for a disease or condition associated with increased expression of MICA in a subject. A control amount desirably corresponds to the MICA amount detected using the same antigen binding fragment in a corresponding sample(s) from one or more control cultures or subjects. Methods of using the antigen binding fragment of the invention to determine MICA amounts can include any immunoassay such as immuno-(western) blot, enzyme-linked immunosorbent assay (ELISA), and flow cytometry, e.g., fluorescence-activated cell sorting (FACS) analysis.

Additionally, MICA detection can be used to monitor the progress of a disorder associated with MICA expression. Amounts of MICA that are significantly elevated or decreased relative to control indicate that the subject's disorder is deteriorating or improving, respectively.

The foregoing screens can be used to identify the presence or to monitor the progress of disorders including, for example, cancer, autoimmune disease, inflammatory conditions and infection, e.g. all of the MICA-associated diseases noted above.

The invention also provides kits suitable for carrying out the methods of the invention. Typically, a kit includes two or more components required for performing a therapeutic or detection method of the invention. Kit components include, but are not limited to, one or more antigen binding fragments, fusion proteins or recombinant T-cells of the invention, appropriate reagents, and/or equipment.

A detection kit can include an antigen binding fragment of the invention and an immunoassay buffer suitable for detecting MICA (e.g., by ELISA or FACS). The kit may also contain one or more microliter plates, standards, assay diluents, wash buffers, adhesive plate covers, and/or instructions for carrying out a method of the invention using the kit. The kit can include an antigen binding fragment of the invention bound to a substrate (e.g., a multi-well plate or a chip), which is suitably packaged and useful to detect MICA. In some embodiments, the kit includes an antigen binding fragment of the invention that is conjugated to a label, such as, a fluorescent label, a biologically active enzyme label, a luminescent label, or a chromophore label. The kit can further include reagents for visualizing the conjugated antigen binding fragment, e.g., a substrate for the enzyme. In some embodiments, the kit includes an antigen binding fragment of the invention that is conjugated to a contrast agent and, optionally, one or more reagents or pieces of equipment useful for imaging the antibody in a subject. In some embodiments, means of taking a sample from an individual and/or of assaying the sample may be provided in the kit.

A kit for therapeutic applications can include, in suitable container means, recombinant T-cells or a nucleic acid construct encoding an antigen binding fragment or fusion molecule thereof, and related reagents of the present invention. In some embodiments, the kit further includes an additional agent for treating cancer, an autoimmune disorder, inflammatory condition or an infectious disease, and the additional agent may be combined with the nucleic acid construct(s) or cells of the invention or may be provided separately in the kit. In certain embodiments the kit includes cells, buffers, cell media, vectors, primers, restriction enzymes, salts, and so forth, for example.

Generally, the antigen binding fragment of the invention in a kit is suitably packaged, e.g., in a vial, pouch, ampoule, and/or any container appropriate for a therapeutic or detection method. Kit components can be provided as concentrates (including lyophilized compositions), which may be further diluted prior to use or they can be provided at the concentration of use. When the antigen binding fragment of the invention for use in vivo, single dosages may be provided in sterilized containers having the desired amount and concentration of agents.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1: Anti-MICA CAR

Anti-MICA CAR was constructed by fusing the B2 scFv to human CD28 hinge-transmembrane-cytoplasmic domains (residues 135-220) and CD3 ζ cytoplasmic domain (residues 52-164). The anti-MICA construct was then cloned into a retroviral vector pFB-neo (Stratagene, Palo Alto, Calif.), and expressed in T cells.

Figure 2B:
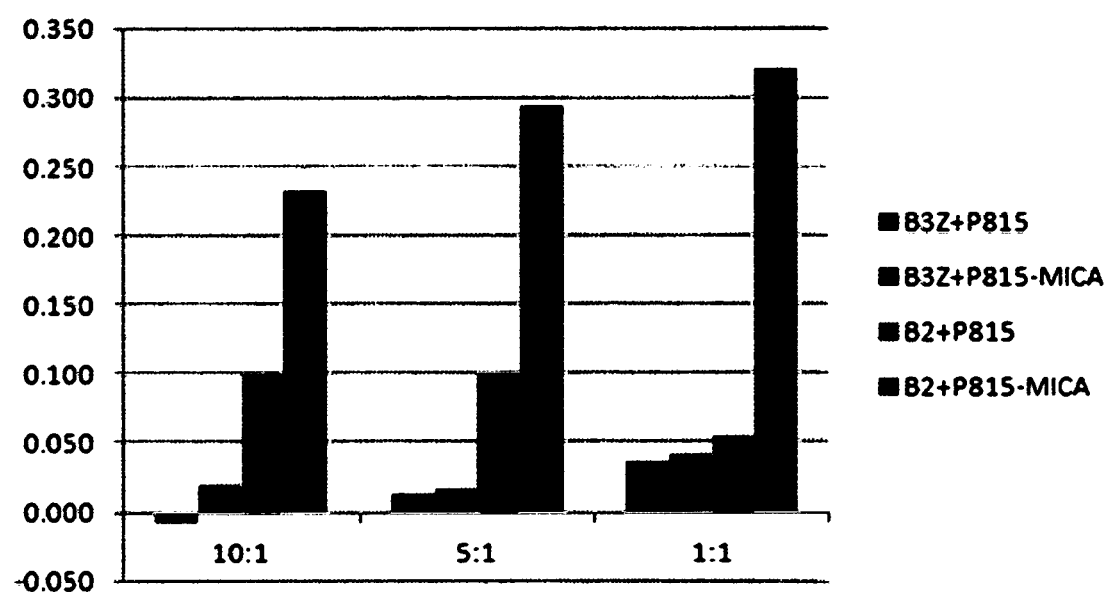

The cells were analyzed for expression of the MICA CAR through a B3Z Assay. B3Z assays were performed according to known methods (Shastri & Gonzalez (1993) *J. Immunol.* 150:2724-36). B3Z (B3xZ.8) is a CD8+ T cell hybridoma that expresses LacZ in response to activation of T cell receptors specific for the SIINFEKL peptide (SEQ ID NO:70) (OVA-immunodominant peptide) in the context of H-2K$^b$ MHC class I molecules. CAR signaling via CD3ζ (CD3-zeta) will induce LacZ expression in a similar manner. Briefly, $10^5$ B3Z or MICA-specific CAR-transduced B3Z cells at ratios of 10:1, 5:1 and 1:1 E:T (effector (B3Z cell):target (tumor cells) were co-cultured in flat-bottom 96-well plates with ID8-GFP, ID8-GFP-MICA, P815 or P815-MICA tumor cells for 24 hours (FIGS. 2A and 2B). P815 is a murine mastocytoma cell line, H-2$^d$ haplotype. ID8 is a mouse ovarian carcinoma cell line. ID8-GFP is a ID8 cell line transduced with the reporter green fluorescent protein (GFP)-expressing lentiviral particles. Both cells were engineered to express human MICA. The plates were spun, and the cell pellets were lysed and incubated with CPRG for detection of LacZ activity. Absorbance at 595 nm was measured by using an enzyme-linked immunosorbent assay plate reader after 6 hours.

The results of this analysis, presented in FIGS. 2A-2B, indicated that the anti-MICA CAR ("B2") was functional as it induced CAR-mediated activation in the presence of MICA on the target cells ("ID8-GFP-MICA" and "P815-MICA"). The B3Z cells alone, which were included in each assay and do not express a MICA binding CAR, did not respond tumor cells when MICA was not present. That is, incubation of the B3Z T cells and tumor cells (either ID8 or P815) alone yielded no signaling activation, as evidenced by there being little or no detectable signal from the LacZ reporter, even in the presence of MICA-expressing tumor cells (see "B3Z+ID8-GFP", "B3Z+ID8-GFP-MICA" samples in FIG. 2A, and "B3Z+P815", and "B3Z+P815-MICA" samples in FIG. 2B). While the sample "B3Z+ID8-GFP-MICA" produced some TCR activation, this was at the highest ratio of E:T (1:1). Likewise, incubation of B3Z T cells with MICA CAR cells in the presence of tumor cells alone did not yield an appreciable TCR activation signal ("B2+ID8-GFP" in FIG. 2A, and "B2+P815" in FIG. 2B). In contrast, the presence of MICA CAR cells ("B2") clearly amplified the TCR activation at all E:T ratios ("B2+ID8-GFP-MICA" in FIG. 2A and "B2+P815-MICA" in FIG. 2B).

Example 2: Anti-MICA BiTE® Activation of T Cells in the Presence of K562 and B16F10 Cells Anti-MICA B2 scFv was fused via a flexible linker (encoded by the sequence GGCGGAGGCGGATCAG-GAGGAGGAGGATCAGGCGGAGGAGGATCA which intervenes the anti-MICA scFv and an anti-OKT3 scFv (i.e, anti-CD3 scFv; Arakawa, et al. (1996) *J. Biochem.* 120:657-62; U.S. Pat. No. 5,929,212, the disclosures of each of which are incorporated herein by reference in their entirety, especially the anti-OKT3 (anti-CD3) antibody sequences disclosed therein) to create an anti-MICA BiTE® construct.

Figure 3A:
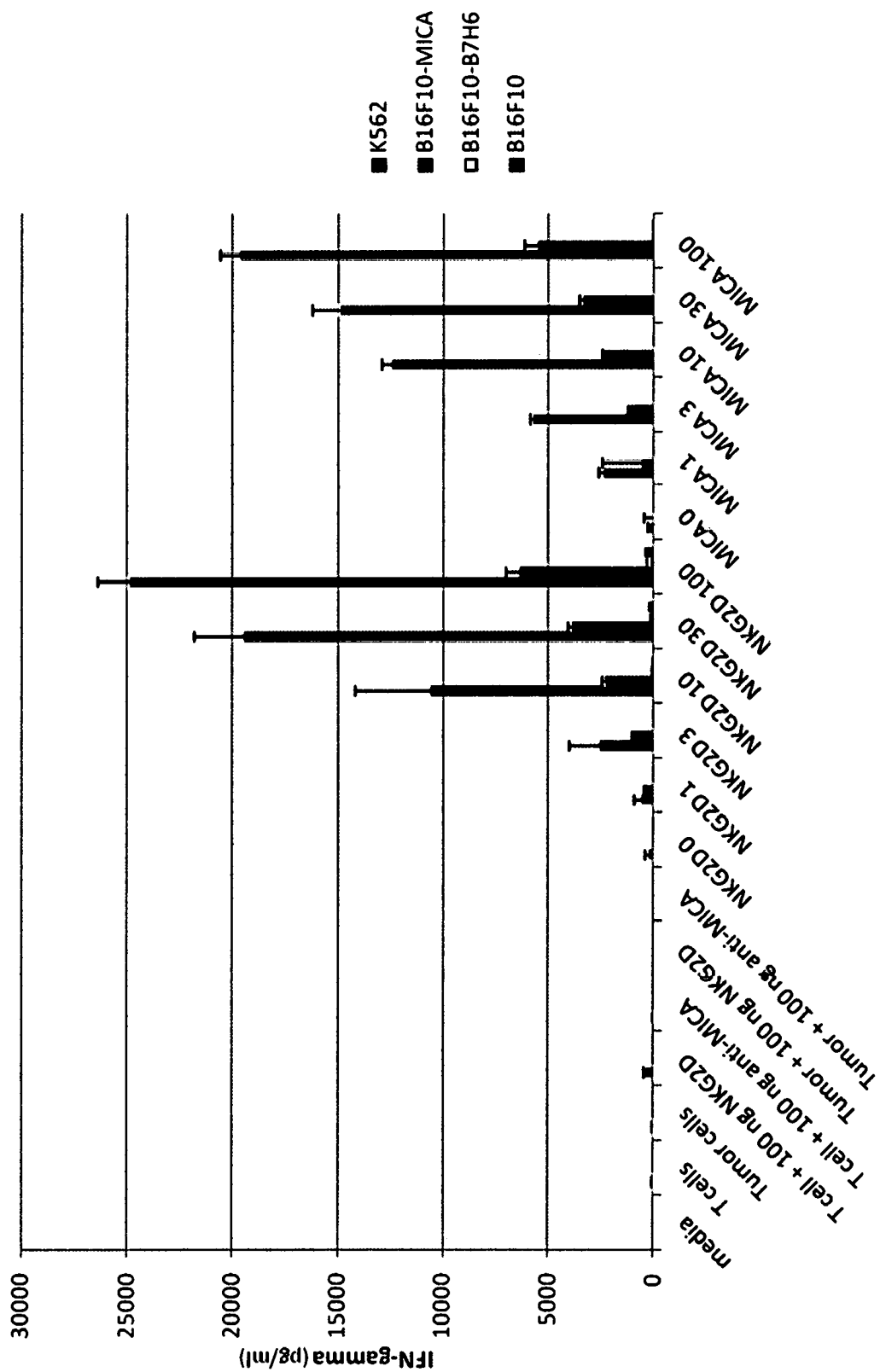
FIGS. 3A and 3B show that anti-MICA BiTE® triggers IFN-γ secretion in a T cell and tumor cell co-culture when tumor cells express MICA (K562, B16F10-MICA). T cells were OKT3-activated human PBMCs (FIG. 3A, Donor U.
Figure 3B:
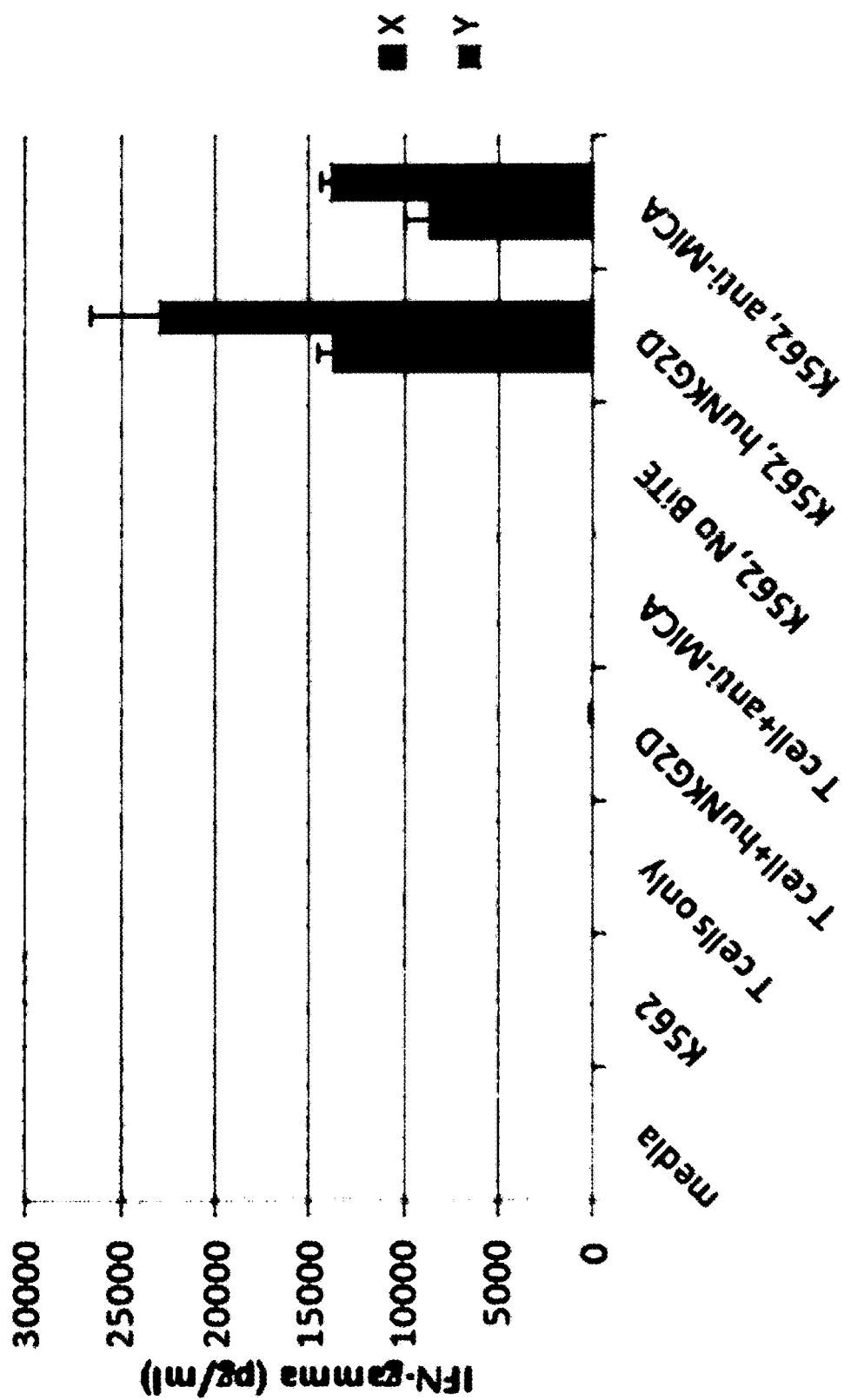

To determine whether anti-MICA BiTE® could engage both T cells and tumor cells and lead to T cell activation, OKT3-activated T cells (expanded for 8 days) were co-cultured with tumor cells (K562 (human chronic myelogenous leukemia (CML) cells), B16F10 (mouse melanoma cells), B16F10-B7H6, and B16F10-MICA) at different doses of a MICA-BiTE®(MICA), or NKG2D-BiTE® (NKG2D) (from 0 to 100 ng/well) for 1 day. Amounts of IFN-γ in cell-free conditioned media were analyzed with ELISA. This analysis indicated that the anti-MICA BiTE® induced IFN-γ secretion into the medium of T cells co-cultured with tumor cells expressing MICA (FIG. 3A). Further, culture of activated T cells from two additional donors (X and Y) confirmed IFN-γ production when cultured in the presence of a MICA-BiTE® and MICA expressing tumor cells (FIG. 3B).

Figure 4A:
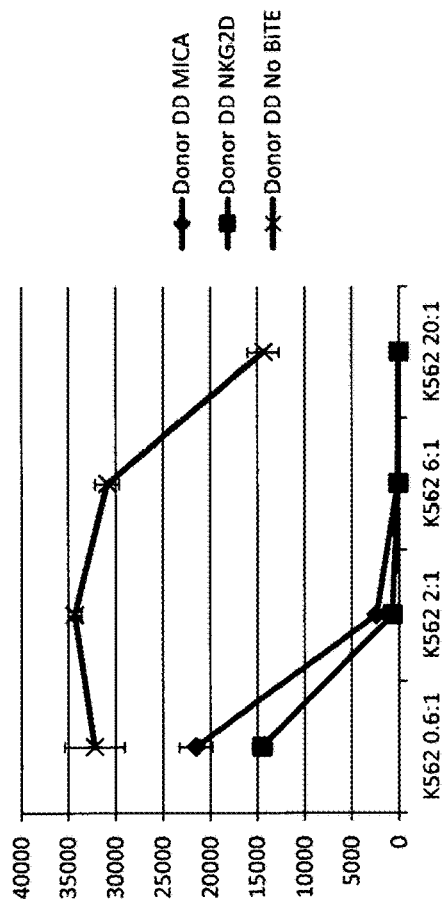
FIGS. 4A and 4B show that human T cells from 2 donors (EE and DD), kill K562 tumor cells in the presence of NKG2D-BiTE® (NKG2D, squares) or anti-MICA BiTE® (MICA, circles). An additional sample of donor EE T cells (crosses) with no BiTE® is included as a negative control. Killing of K562 cells is measured as decreasing luciferase emission (relative light units) at different effector:target cell ratios (0.6:1, 2:1, 6:1, 20:1).
Figure 4B:
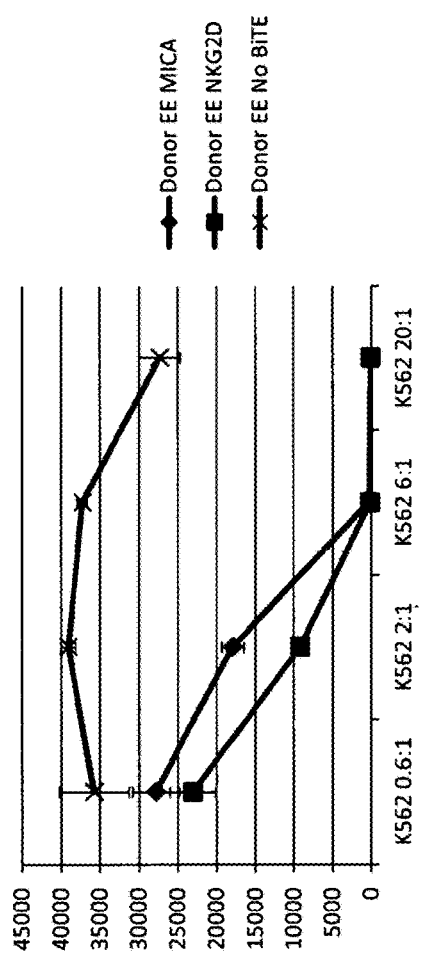

Example 3: Anti-MICA BiTE® or NKG2D-BiTE® Activation of Donor T Cells in the Presence of K562 Cells The same anti-MICA BiTE® construct of Example 2 was used in these experiments. To determine whether anti-MICA BiTE® and/or NKG2D-BiTE® could engage both T cells and tumor cells and lead to T cell activation, OKT3-activated T cells (expanded for 8 days) were co-cultured with K562 cells T cells were obtained from two different human donors (EE and DD, FIGS. 4A and 4B, respectively) and activated. The tumor cells express luciferase, and relative light units (RLU) were determined after 22 hours of incubation with T cells +/− anti-MICA BiTE® (MICA) or NKG2D-BiTE® (NKG2D) at the indicated ratios, as shown in FIG. 4A and FIG. 4B (two different donors, EE and DD, respectively). A loss of RLU indicates less survival of the tumor cells.

The T cell culture conditions used in the assay are described schematically below.

T Cell Culture Conditions
1. Donor PBMCs are thawed on Day 0
2. PBMCs are plated at 1 million cells per ml in RPMI with IL2 and soluble OKT3 mabs in a T75 flask.
   a. Final IL2 concentration: 50 U/ml
      i. Stock is 10,000 Units/ml
   b. Final OKT3 concentrations: 40 ng/ml
      i. Stock is 1 mg/ml, UltraLEAF™ Purified anti human CD3 Biolegend catalog number 317325.
   c. RPMI: HEPES, Non-essential Amino acids, Sodium Pyruvate, Penicillin/Streptomycin, BME, 10% FBS.
3. On Day 3, T cells are washed twice with HBSS.
   a. Cells are spun down for 5 minutes are 500 RCF at room temperature.
   b. Cells are resuspended in HBSS and spun down. Repeat.
   c. The final resuspension is in RPMI with IL2 (50 U/ml) with cells at 1 million/ml.
4. Day 5, T cells are split to 1 million/ml.
   a. RPMI media is used and IL2 added at 50 U/ml.
5. Day 7 (day before cells are used), T cells are split to 1 million/ml.
   a. RPMI media is used and IL2 added at 50 U/ml
6. Day 8, cells are used in Assay.
   a. T cells are washed once in HBSS before resuspending in RPMI to be used in assay The data obtained from these experiments show that the human T cells from donors EE and DD kill K562 tumor cells in the presence of NKG2D-BiTE® (NKG2D) or anti-MICA BiTE® (MICA) as evidenced by the decrease in RLU emitted from the K562 cells.

Example 4: Anti-MICA BiTE® or NKG2D-BiTE® Activation of Donor T Cells in the Presence of PANC1 Cells The anti-MICA BiTE® construct of Example 2 was again used in these experiments. These assays utilized a cytotoxicity luciferase assay format which in general comprised the following steps:

Cytotoxicity Luciferase Assay Format
1. Dilute Luciferin
   a. Stock of luciferin in 15,000 μg/ml in PBS
   b. Dilute to 200 μg/ml in RPMI.
   c. Add 50 μl of 200 μg/ml to each well using a multichannel pipet.
2. Read Plate:
   d. Turn computer on.
   e. Turn Luminometer on. The switch is in the back.
   f. Open MikroWin 2000
   g. Our program is called: luciferase 2 sec
   h. At the bottom of the screen, write file name. (Always include date)

i. Run program. It will ask you to load the plate. Load the plate and be sure it sits in the tray correctly so that it does not jam.
j. To Export data into Excel format: File→Export→Raw Data Export Driver. Export to a flash drive.
k. When done, go to Instrument→Unload plate to remove the plate. Close door by selecting "Load plate"
l. Open file in Excel to make sure it saved correctly.
m. Close MikroWin 2000. Turn off Computer. Turn off Luminometer.

Figure 5A:
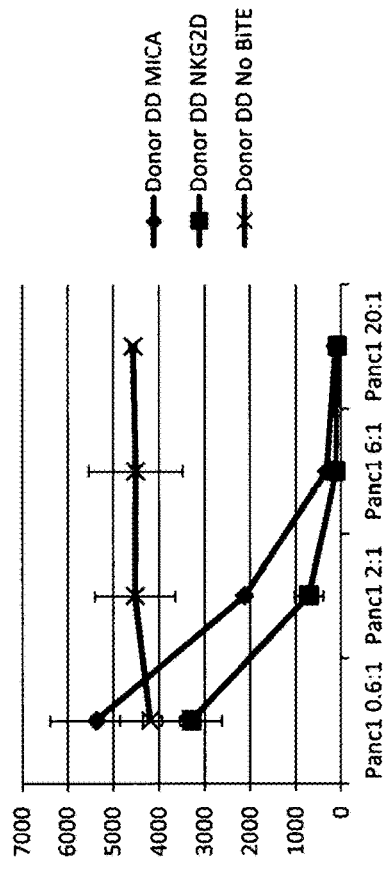
FIGS. 5A and 5B show that human T cells from 2 donors (EE and DD), kill PANC1 tumor cells in the presence of NKG2D-BiTE® (NKG2D, squares) or anti-MICA BiTE® (MICA, circles). An additional sample of donor EE T cells (crosses) with no BiTE® is included as a negative control. Killing of PANC1 cells is measured as decreasing luciferase emission (relative light units) at different effector:target cell ratios (0.6:1, 2:1, 6:1, 20:1). The results of these experiments contained in FIG. 6 show that T cells from 2 donors (EE and DD) incubated with different amounts of anti-MICA BiTE® or NKG2D-BiTE® (from 0 to 50 ng/ml) induced IFN-γ secretion into the medium when co-cultured with various tumor cells expressing MICA (K562, PC3, PANC1, and MCF7). Wells labeled as "T cells + . . . " had T cells without tumor cells in them.
Figure 5B:
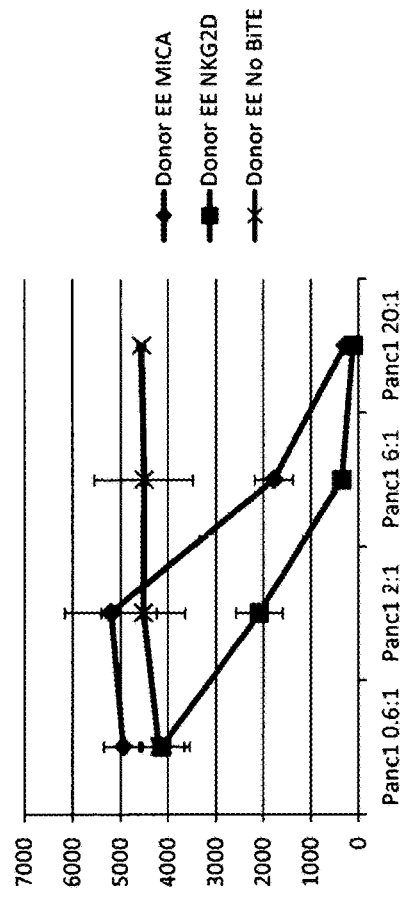

In these experiments in order to assess whether anti-MICA BiTE® and/or NKG2D-BiTE® could engage both T cells and PANC1 (human pancreatic epitheloid carcinoma) tumor cells and lead to T cell activation, OKT3-activated T cells (expanded for 8 days) were co-cultured with PANC1 cells. In these experiments T cells were obtained from two different human donors (EE and DD, FIG. 5A and 5B, respectively) and activated. The tumor cells express luciferase, and relative light units (RLU) were determined after 22 hours of incubation with T cells +/- anti-MICA BiTE® (MICA) or NKG2D-BiTE®(NKG2D) at the indicated ratios, as above-described and as shown in FIG. 5A and FIG. 5B.

The data demonstrated that the human T cells from 2 donors effectively killed PANC1 tumor cells in the presence of NKG2D-BiTE® (NKG2D) or anti-MICA BiTE® (MICA) as evidenced by the decrease in RLU emitted from the PANC1 cells.

Example 5: Anti-MICA BiTE® or NKG2D-BiTE® Activation of Donor T Cells in the Presence of a Panel of Tumor Cells The same anti-MICA BiTE® construct of Example 2 was again used in these experiments. In these experiments it was assessed whether the anti-MICA BiTE® construct elicited the expression of interferon gamma ELISA assay essentially as follows:

Interferon Gamma ELISA Assay
1. Count and resuspend tumor lines in RPMI complete medium (with FBS & supplements)
2. Prepare BiTE® dilutions in RPMI complete medium
3. Plate T cells, tumor cells, BiTE, and media, as appropriate.
4. Collect supernatant after 24 hrs and freeze.
5. Follow Biolegend Interferon gamma ELISA Kit instructions.

Specifically, in order to assess whether anti-MICA BiTE® and/or NKG2D-BiTE® could engage both T cells and tumor cells and lead to T cell activation, OKT3-activated T cells (two donors, EE and DD, expanded for 8 days) were co-cultured with human tumor cells (K562, PC3 (human prostate adenocarcinoma), PANC1, MCF7 (human breast epithelial adenocarcinoma)) at different doses of a MICA-BiTE® (MICA) or NKG2D-BiTE® (NKG2D)(from 0 to 50 ng/well) for 1 day. The amounts of IFN-γ in cell-free conditioned media were analyzed by ELISA as described above.

Figure 6:
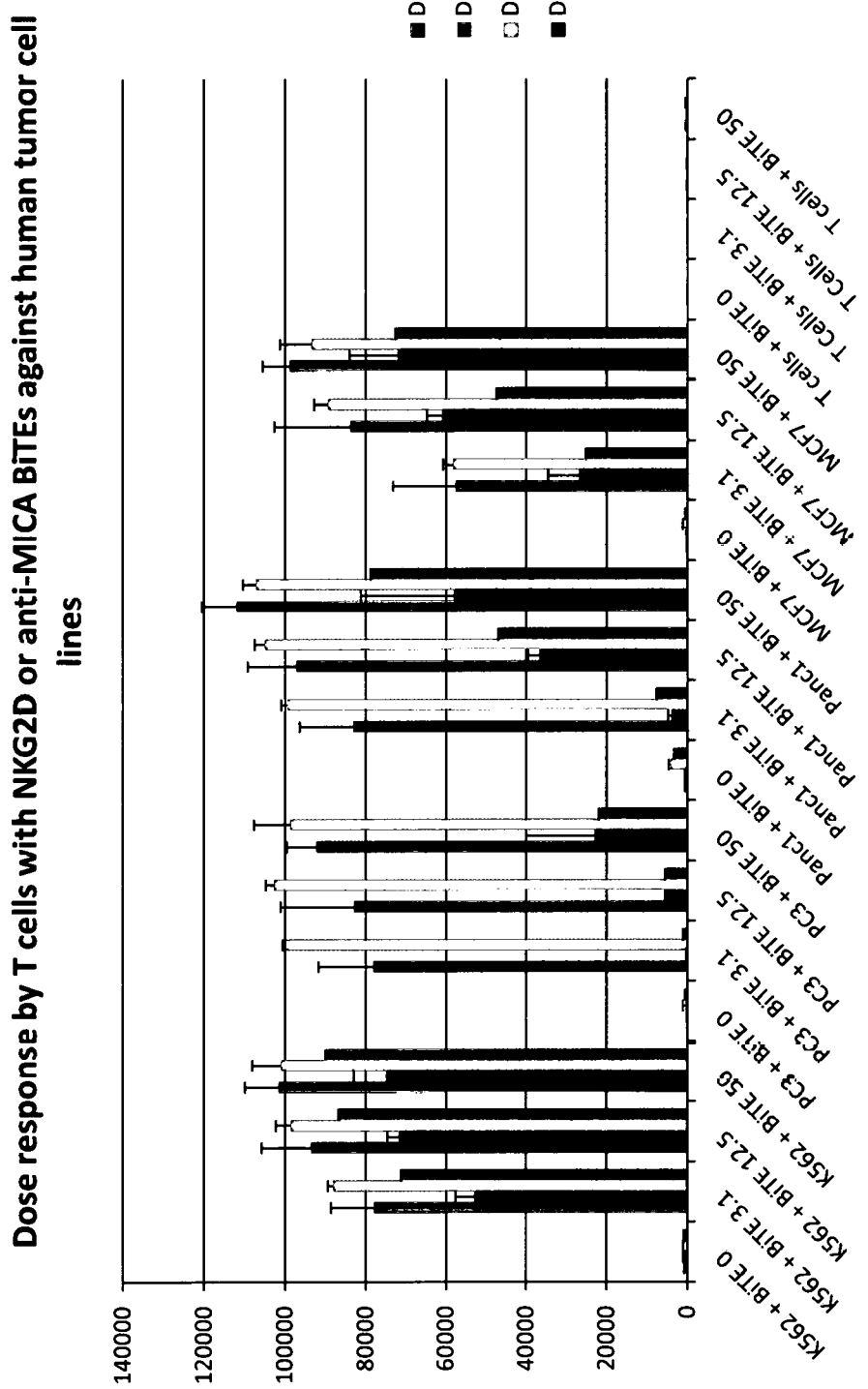

The data presented in FIG. 6 indicated that anti-MICA BiTE® and NKG2D-BiTE® induced IFN-γ secretion into the medium of T cells co-cultured with tumor cells expressing MICA. Culture of the activated T cells from both donors confirmed IFN-γ production when cultured in the presence of a MICA-BiTE®. These results further corroborate that anti-MICA BiTE® as described herein may be used to elicit anti-tumor activity against target tumors in vivo as IFN-γ expression is a key effector mechanism against tumors.

Example 6: T Cell EC50 Values for IFNγ Response to Anti-MICA BITE® or NKG2D-Bite®

Figure 7A:
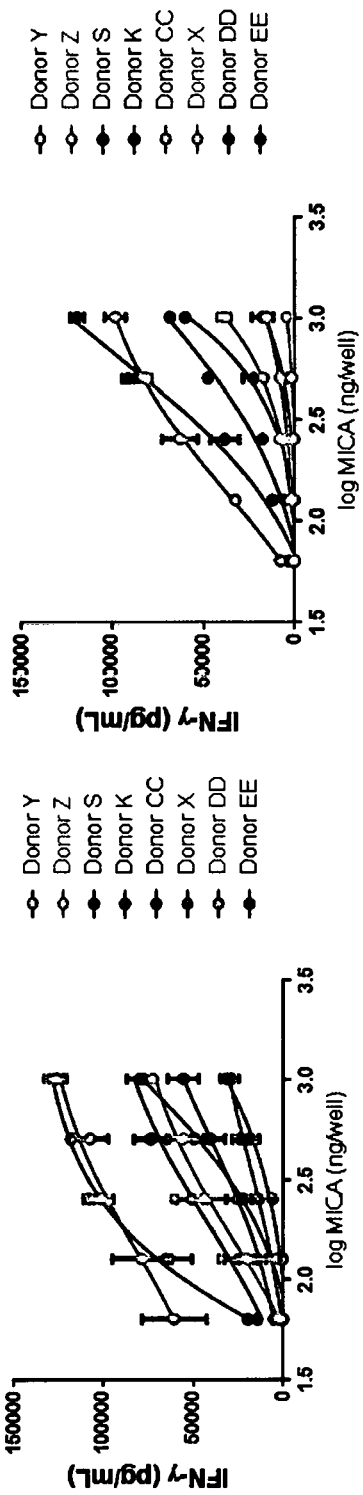
FIG. 7A and FIG. 7B show that T cells from 8 donors were activated by exposure to human NKG2D BiTE® (FIG. 7A) or anti-MICA BiTE®'s (FIG. 7B) in plate wells with immobilized rMICA at a range of different densities (0-1000 ng/well).
Figure 7B:
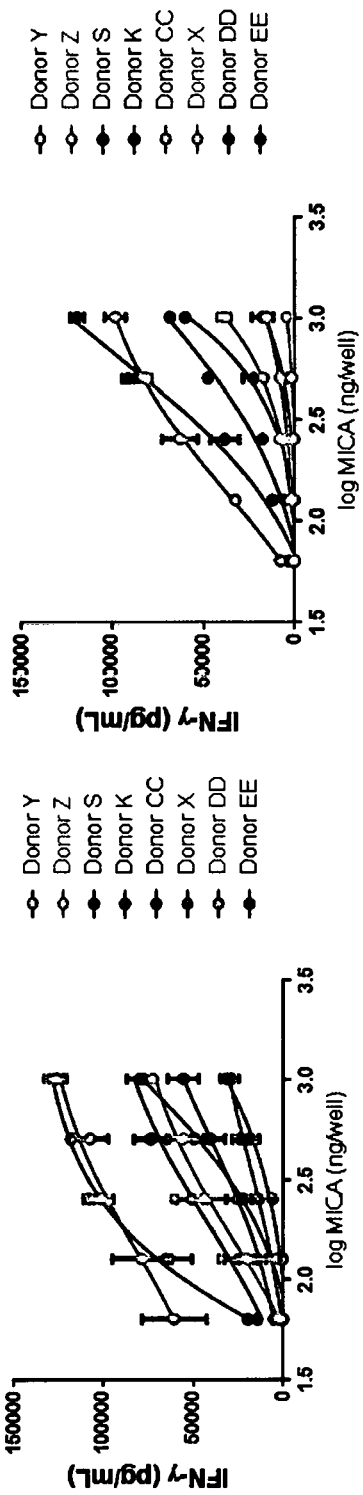

In these experiments T cells from 8 donors were activated by exposure to human NKG2D BiTE® or anti-MICA BiTE® in plate wells using plate bound MICA at a range of different densities (0-1000 ng/well). Cell-free medium was collected and IFNγ was measured by ELISA, again as described in Example 4. EC50 values were calculated from the dose response curves. FIG. 7A presents data relating to huNKG2D BiTE® activation of donor T cells. FIG. 7B presents data relating to anti-MICA BiTE® activation of donor T cells. Again these results obtained with T cells of different donors further corroborate that anti-MICA BiTE® as described herein may be used to elicit anti-tumor activity against target tumors in vivo as IFN-γ expression is a key effector mechanism against tumors.

Example 7: T Cell Dose Response to Tumor Cells with Anti-MICA BiTE® or NKG2D-Bite®

Figures 8A, 8B, 8C:
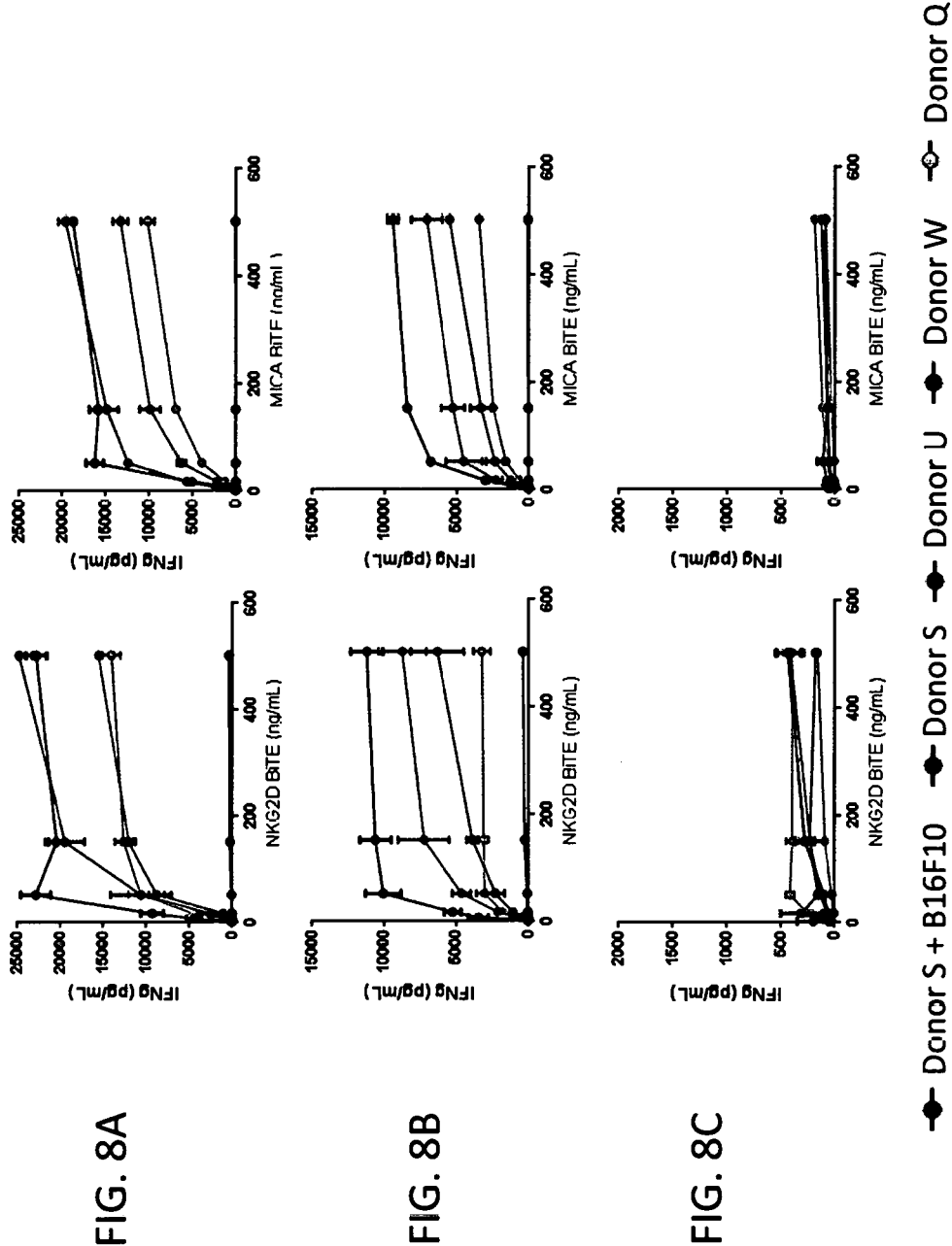
FIGS. 8A-8C show dose response curves in which T cells from four donors were activated in an NKG2D BiTE® or anti-MICA BiTE®-dependent manner (0 to 500 ng/ml) against K562 cells (FIG. 8A, left, right panel respectively), B16F10-MICA cells (FIG. 8B, left, right panel respectively), and B16F10-B7H6 cells (negative control cells) (FIG. 8C, left, right panel respectively).

In these experiments a T cell activation dose response was measured using donor T cells from 4 different human donors against K562 (FIG. 8A, left, right panel), B16F10-MICA (FIG. 8B, left, right panels) and B16F10-B7H6 (FIG. 8C, left, right panels, negative control) in the presence of either anti-MICA BiTE® or NKG2D-BiTE® (negative control) at different concentrations (0 to 500 ng/ml). T cells from four donors were tested. In one set of samples, (donor S in the Figure) the donor T cells included B16F10 as an additional negative control.

IFN-γ production was measured by ELISA as described in Example 4. The data shown in the Figure indicate that the T cells were activated in an anti-MICA BiTE®-dependent manner with maximal response being observed at concentrations below 200 ng/ml. These results further corroborate that anti-MICA BiTE® as described herein may be used to elicit anti-tumor activity against target tumors in vivo as IFN-γ expression is a key effector mechanism against tumors.

The entire disclosure of each document cited (including patents, patent applications, journal articles, abstracts, manuals, books, or other disclosures) in the Background of the Invention, Detailed Description, and Examples is herein incorporated by reference in their entireties. The invention is further described by the claims which follow. This invention includes all modifications and equivalents of the subject matter recited in the claims appended hereto as permitted by applicable law.

What is claimed is:

1. A MICA binding molecule that specifically binds to major histocompatibility complex class I chain-related gene A (MICA) selected from an antibody and an antigen binding fragment, wherein the MICA binding molecule comprises:
   (i) variable heavy ("VH") CDR1, 2 and 3 polypeptides of SEQ ID NO:35, 36 and 22 respectively; and variable light ("VL") CDRs of SEQ ID NO:26, 28 and 37 respectively;
   and wherein:
   the antigen binding fragment comprises an antigen binding domain, a single chain variable fragment (scFv), an scFv-Fc, or an antibody fragment selected from $F(ab')_2$, $F(ab)_2$, $F(ab')$, $F(ab)$, Fv, and dsFv; and
   the antigen binding fragment is optionally comprised within an $(scFv)_2$, a di-scFv, a bi-scFv, a diabody, a bivalent single chain variable fragment, a trivalent single chain variable fragment, a tetravalent single chain variable fragment, a kappa-lambda body, a chimeric antigen receptor (CAR), a bi-specific T-cell engager, a dual affinity retargeting reagent, or other fusion protein.

2. A recombinant cell engineered to express the MICA binding molecule according to claim 1, wherein the cell is selected from a natural killer (NK) cell, a T cell, a cytotoxic T cell, a CD4+ cell, a B cell, a cell of myeloid lineage, a memory cell, a cell progenitor, a monocyte, a macrophage, a dendritic and a neutrophilic granulocyte.

3. The MICA binding molecule according to claim 1, or a cell which expresses the MICA binding molecule according to claim 1, which:
   (i) comprises or is attached to a label;
   (ii) is directly or indirectly attached or fused to a cytotoxic agent or a therapeutic radioisotope;
   (iii) is comprised in a pharmaceutical composition comprising a therapeutically or diagnostically effective amount of said MICA binding molecule or said cell and a pharmaceutically acceptable carrier; and/or
   (iv) is comprised in a kit, wherein optionally the antigen binding fragment is conjugated to a label.

4. The MICA binding molecule according to claim 1, wherein the chimeric antigen receptor further comprises
   a transmembrane region, and
   an intracellular T-cell receptor signaling domain or FcRy signaling domain.

5. The chimeric antigen receptor of claim 4, wherein the transmembrane region and intracellular T-cell receptor signaling domain are from CD3 zeta;
   and wherein the CAR further comprises a hinge region or spacer region.

6. A recombinant T cell or other immune cell comprising the chimeric antigen receptor of claim 4.

7. The recombinant T cell or other immune cell of claim 6, which expresses another CAR, and/or is modified to reduce or eliminate endogenous TCR expression or function and/or to reduce or eliminate the expression or function of an HLA gene or HLA regulator gene products.

8. The MICA binding molecule according to claim 1, wherein the bi-specific T-cell engager further comprises
   a second antigen binding domain which binds to an immune effector cell antigen.

9. The bi-specific T-cell engager of claim 8, wherein the immune effector cell antigen is CD3 and the second antigen binding domain comprises
   (a) a heavy chain variable region comprising,
      (i) a CDR1 of SEQ ID NO:45,
      (ii) a CDR2 of SEQ ID NO:46, and
      (iii) a CDR3 of SEQ ID NO:47; and
   (b) a light chain variable region comprising,
      (i) a CDR1 of SEQ ID NO:48,
      (ii) a CDR2 of SEQ ID NO:49, and
      (iii) a CDR3 of SEQ ID NO:50.

10. The MICA binding molecule according to claim 1, further comprising a second antigen binding domain with affinity for an effector cell antigen.

11. The MICA binding molecule of claim 10, wherein: the effector cell antigen comprises one or more of CD3, CD16, CD25, CD28, CD64, CD89, NKG2D, and NKp46.

12. The CAR of claim 4, wherein
    the intracellular signaling domain is selected from any one or more of CD3, FcRy, Syk-PTK, CD28, 41BB, CD134, ICOS, OX40, and CD19, in any order from carboxy terminus to amino terminus.

13. The MICA binding molecule of claim 11, wherein the effector cell antigen is CD3 and the second antigen binding domain comprises $V_H$ CDR1, 2 and 3 polypeptides of SEQ ID NO: 45, 46 and 47 respectively, and $V_L$ CDR1, 2 and 3 polypeptides of SEQ ID NO: 48, 49 and 50 respectively.

14. The recombinant cell of claim 2, wherein the cell is a primary cell obtained from a human donor or donors.

15. The MICA binding molecule of claim 11, wherein the effector cell antigen is CD3.

* * * * *

UNITED STATES PATENT AND TRADEMARK OFFICE
CERTIFICATE OF CORRECTION

PATENT NO. : 10,744,157 B2
APPLICATION NO. : 15/561748
DATED : August 18, 2020
INVENTOR(S) : Sentman et al.

It is certified that error appears in the above-identified patent and that said Letters Patent is hereby corrected as shown below:

In the Specification

At Column 21, "TABLE 3" at approximately Line 13, the sequence identified as "SEQ ID NO: 22" should be corrected from EGAHEWADSFDI to EGAHEWADAFDI.

Signed and Sealed this
Fourteenth Day of March, 2023

Katherine Kelly Vidal
*Director of the United States Patent and Trademark Office*